US009757339B2

(12) United States Patent
Little

(10) Patent No.: US 9,757,339 B2
(45) Date of Patent: Sep. 12, 2017

(54) ARTIFICIAL CELL CONSTRUCTS FOR CELLULAR MANIPULATION

(71) Applicants: University of Pittsburgh—Of the Commonwealth System of Higher Education, Pittsburgh, PA (US); Massachusetts Institute of Technology, Cambridge, MA (US)

(72) Inventor: Steven R. Little, Allison Park, PA (US)

(73) Assignees: University Of Pittsburgh—Of The Commonwealth System Of Higher Education, Pittsburgh, PA (US); Massachusetts Institute Of Technology, Cambridge, MA (US)

( * ) Notice: Subject to any disclaimer, the term of this patent is extended or adjusted under 35 U.S.C. 154(b) by 53 days.

(21) Appl. No.: 14/333,000

(22) Filed: Jul. 16, 2014

(65) Prior Publication Data

US 2014/0356445 A1    Dec. 4, 2014

Related U.S. Application Data

(63) Continuation of application No. 13/383,122, filed as application No. PCT/US2010/041463 on Jul. 9, 2010, now Pat. No. 8,846,098.

(Continued)

(51) Int. Cl.
*A61K 9/00* (2006.01)
*A61K 9/16* (2006.01)
(Continued)

(52) U.S. Cl.
CPC .......... *A61K 9/1635* (2013.01); *A61K 9/0019* (2013.01); *A61K 9/1682* (2013.01);
(Continued)

(58) Field of Classification Search
CPC .......... A61K 39/395; A61K 9/00; A61K 9/14; A61K 45/00; A61K 38/00; A61K 38/18
See application file for complete search history.

(56) References Cited

U.S. PATENT DOCUMENTS

| 4,685,883 A | 8/1987 | Jernberg | 433/215 |
|---|---|---|---|
| 5,059,123 A | 10/1991 | Jernberg | 433/215 |

(Continued)

FOREIGN PATENT DOCUMENTS

| EP | 2288372 B1 | 2/2012 |
|---|---|---|
| WO | WO/2004/006951 | 1/2004 |

(Continued)

OTHER PUBLICATIONS

Rothstein et al., (J Mater Chem. 2008. 18:1873-1880).*

(Continued)

*Primary Examiner* — Cherie M Stanfield
(74) *Attorney, Agent, or Firm* — Medlen & Carroll, LLP

(57) ABSTRACT

The present invention contemplates induction of immunological tolerance thereby providing permanent allograft acceptance. This method obviates the need for a lifelong regimen of immunosuppressive agents which can increase the risk of infection, autoimmunity, and cancer. Immunological tolerance is thought to be mediated by regulatory T lymphocytes ($T_{reg}$ cells) with immunosuppressive capabilities. A therapeutically relevant platform comprising artificial constructs are contemplated comprising numerous soluble and surface bound $T_{reg}$ cell stimulating factors that may induce tolerance following allograft transplantation. Such artificial constructs, being the size of a cell, have surface bound monoclonal antibodies specific to regulatory T-cell surface moieties and encapsulated soluble regulatory T-cell modulating factors.

17 Claims, 26 Drawing Sheets
(8 of 26 Drawing Sheet(s) Filed in Color)

Related U.S. Application Data

(60) Provisional application No. 61/224,571, filed on Jul. 10, 2009.

(51) Int. Cl.
| | |
|---|---|
| *A61K 38/18* | (2006.01) |
| *A61K 38/20* | (2006.01) |
| *A61K 47/48* | (2006.01) |
| *B01J 13/00* | (2006.01) |

(52) U.S. Cl.
CPC ...... *A61K 38/1841* (2013.01); *A61K 38/2013* (2013.01); *A61K 47/48853* (2013.01); *B01J 13/0065* (2013.01); *B01J 2208/00823* (2013.01)

(56) References Cited

U.S. PATENT DOCUMENTS

| | | | | |
|---|---|---|---|---|
| 5,197,882 | A | 3/1993 | Jernberg | 433/215 |
| 5,290,271 | A | 3/1994 | Jernberg | 604/891.1 |
| 5,885,829 | A | 3/1999 | Mooney et al. | 435/325 |
| 5,939,047 | A | 8/1999 | Jernberg | 424/49 |
| 6,123,957 | A | 9/2000 | Jernberg | 424/435 |
| 6,576,226 | B1 | 6/2003 | Jernberg | 424/49 |
| 6,703,037 | B1* | 3/2004 | Hubbell | A61K 9/1635 424/422 |
| 6,726,898 | B2 | 4/2004 | Jernberg | 424/49 |
| 8,053,235 | B2 | 11/2011 | Buckner et al. | 435/372.3 |
| 8,128,934 | B2 | 3/2012 | Suzumura et al. | 435/158.1 |
| 2008/0063652 | A1 | 3/2008 | Pykett et al. | 424/184.1 |
| 2009/0028876 | A1 | 1/2009 | Teng | 424/172.1 |
| 2009/0208471 | A1 | 8/2009 | Yun | 424/93.71 |
| 2010/0247562 | A1* | 9/2010 | Gong | C07K 16/18 424/193.1 |
| 2011/0059125 | A1 | 3/2011 | Tzianabos et al. | 424/197.11 |
| 2011/0123502 | A1 | 5/2011 | Barry et al. | 424/93.71 |
| 2011/0123590 | A1 | 5/2011 | Iwashima et al. | 424/422 |
| 2011/0178502 | A1 | 7/2011 | Poznansky et al. | 604/506 |
| 2011/0229448 | A1 | 9/2011 | Kelleher et al. | 424/93.71 |

FOREIGN PATENT DOCUMENTS

| | | |
|---|---|---|
| WO | WO/2008/150868 | 12/2008 |
| WO | WO/2010/017220 | 2/2010 |
| WO | WO/2011/004264 | 1/2011 |
| WO | WO/2011/006029 | 1/2011 |
| WO | WO/2011/014871 | 2/2011 |
| WO | WO/2011/017303 | 2/2011 |
| WO | WO/2011/085343 | 7/2011 |

OTHER PUBLICATIONS

Sigma-Aldrich Catalog for Resomer Polymers (dating back to 1977). (www.sigmaaldrich.com/materials-science/polymer-science/resomer.html) (last accessed Jul. 8, 2016).*
Frietas, Nanomedicine, vol. I: Basic capabilities. 1999. 8.5.1. Cytometrics, pp. 1-2 (www.nanomedicine.com/NMI/8.5.1.htm last accessed Mar. 10, 2017).*
Machalek, Inside the Cell. Chapter 1. National Institute of General Medical Sciences, p. 4 of 8 from publications.nigms.nih.go/insidethecell/chapter1.htmlat (last accessed Mar. 10, 2017).*
Steenblock et al., (Molecular Therapy. Apr. 2008;16(4):765-772).*
Abe, T. et al. (2006) "Osteoblast differentiation is impaired in SOCS-1-deficient mice," *Journal of Bone and Mineral Metabolism* 24(4), 283-290.
Baatar, D. et al. (2007) "Human Peripheral Blood T Regulatory Cells (Tregs), Functionally Primed CCR4+ Tregs and Unprimed CCR4—Tregs, Regulate Effector T Cells Using FasL," *The Journal of Immunology* 178(8), 489-4900.
Backes, J.M. et al. (2004) "Role of C-Reactive Protein in Cardiovascular Disease", *The Annals of Pharmacotherpay* 38(1), 110-118.

Baker, P. J. (2000) "The role of immune responses in bone loss during periodontal disease," *Microbes and Infection* 2(10), 1181-1192.
Barrat, F. J. et al. (2002) "In Vitro Generation of Interleukin 10—producing Regulatory CD4+ T Cells is Induced by Immunosuppressive Drugs and Inhibited by T Helper Type 1 (Th1)- and Th2-inducing Cytokines", *The Journal of Experimental Medicine* 195(5), 603-616.
Belghith, M. et al. (2003) "TGF-[beta]-dependent mechanisms mediate restoration of self-tolerance induced by antibodies to CD3 in overt autoimmune diabetes," *Nature Medicine* 9(9), 1202-1208.
Boggess, K. A. et al. (2006) "Maternal periodontal disease in early pregnancy and risk for a small-for-gestational-age infant," *American Journal of Obstetrics and Gynecology* 194(5), 1316-1322.
Brocker, T. et al. (1997) "Targeted Expression of Major Histocompatibility Complex (MHC) Class II Molecules Demonstrates that Dendritic Cells Can Induce Negative but Not Positive Selection of Thymocytes In Vivo," *The Journal of Experimental Medicine* 185(3), 541-550.
Bromley, S. K. et al. (2008) "Orchestrating the orchestrators: chemokines in control of T cell traffic," *Nature Immunology* 9(9), 970-980.
Brusko, T. M. et al. (2008) "Human regulatory T cells: role in autoimmune disease and therapeutic opportunities," *Immunological Reviews* 223(1), 371-390.
Burns, E. et al. (2006) "Cutting Edge: TLR2 is Required for the Innate Response to Porphyromonas gingivalis: Activation Leads to Bacterial Persistence and TLR Deficiency Attenuates Induced Alveolar Bone Resorption," *The Journal of Immunology* 177(12), 8296-8300.
Campanelli, A. P. et al. (2006) "CD4+CD+ T Cells in Skin Lesions of Patients with Cutaneous Leishmaniasis Exhibit Phenotypic and Functional Characteristics of Nature Regulatory T Cells," *Journal of Infectious Diseases* 193(9), 1313-1322.
Cannizzarom S. M. et al. (1998) "A novel biotinylated degradable polymer for cell-interactive applications," *Biotechbnology and Bioengineering* 58(5), 529-535.
Cardoso, C. T. et al. (2008) "Characterization of CD4+CD25+ natural regulatory T cells in the inflammatory infiltrate of human chronic periodontitis," *Journal of Leukocyte Biology* 84(1), 311-318.
Chen, D. et al. (2006) "T Regulatory Cells and Migration," *American Journal of Transplantation* 6(7), 1518-1523.
Chen, H.-Y. et al. (2007) "Colloids with high-definition surface structures," *Proceedings of the National Academy of Sciences* 104(27), 11173-11178.
Chen, M.-L. et al. (2005) "Regulatory T cells suppress tumor-specific CD8 T cell cytoxcityt through TGF-β signals in vivo,"*Proceedings of the National Academy of Sciences of the United States of America* 102(2), 419-424.
Chorny, A. et al. (2006) "Vasoactive intestinal peptide induces regulatory dendritic cells that prevent acute graft-versus-host disease while maintainging the graft-versus-tumor response," *Blood* 107(9), 3787-3794.
Claudino, M. et al. (2008) "The broad effects of the functional IL-10 promoter-592 polymorphism: modulation of IL-10, TIMP-3, and OPG expression and their association with periodontal disease outcome," *Journal of Leukocyte Biology* 84(6), 1563-1573.
Curiel, T. J. et al. (2004) "Specific recruitment of regulatory T cells in ovarian carcinoma fosters immune privilege and predicts reduced survival," *Nature Medicine* 10(9), 942-949.
Curtsinger, J. et al. (1997) "Artificial cell surface sonstructs for studying receptor-ligand contributions to lymphocyte activation," *Journal of Immunological Methods* 209(1), 47-57.
De Smedt, T. et al. (1997) "Effect on interleukin-10 on dendritic cell maturation and function," *European Journal of Immunology* 27(5), 1229-1235.
Delgado, M. et al. (2005) "Vasoactive intestinal peptide generated CD+CD25+ regulatory T cells in vivo," *Journal of Leukocyte Biology* 78(6), 1327-1338.
Delgado, M. et al. (2004) "VIP/PACAP preferentially attract Th2 effectors through differential regulation of chemokine production by dendritic cells," *The FASEB Journal*.

(56) References Cited

OTHER PUBLICATIONS

Doh, J. et al. (2006) "Immunological synapse arrays: Patterned protein surfaces that modulate immunological synapse structure formation in T cells," *Proceedings of the National Academy of Sciences* 103(15), 5700-5705.

Dutzan, N. et al. (2009) "Over-expression of forkhead box P3 and its association with receptor activator of nuclear factor-κ B ligand, interleukin (IL)-17, IL-10 and transforming growth factor-β during the progression of chronic periodontitis," *Journal of Clinical Periodontology* 36(5), 396-403.

Eke, P. I. et al. (2007) "CDC Periodontal Disease Surveillance Project: Background, Objectives, and Progress Report," *Journal of Periodontology* 78(7s), 1366-1371.

Ernst, C. W. O. et al. (2007) "Diminished forkhead box P3/CD25 double-positive T regulatory cells are associated with the increased nuclear factor-kB ligand (RANKL+) T cells in bone resorption lesion of periodontal disease," *Clinical & Experimental Immunology* 148(2), 271-280.

Falany, M. L. et al. (2001) "Osteoclasts Secrete the Chemotactic Cytokine Mim-1," *Biochemical and Biophysical Research Communications* 281(1), 180-185.

Fan, X. et al. (2004) "Donor-specific B-cell tolerance after ABO-incompatible infant heart transplantation," *Nature Medicine* 10(11), 1227-1233.

First, M. R. (2002) "Immunosupressive agents and their actions," *Transplantation Proceedings* 34(5), 1369-1371.

Fisher, M. A. et al. (2008) "Periodontal Disease and Other Nontraditional Risk Factors for CKD," *American Journal of Kidney Diseases* 51(1), 45-52.

Fontenot, J. D. et al. (2003) "Foxp3 programs the development and function of CD4+CD25+ regulatory T cells," *Nature Immunology* 4(4), 330-336.

Frasca, L. et al. (2002) "Human Anergic CD4+ T Cells Can Act as Suppressor Cells by Affecting Autologous Dendritic Cell Conditioning and Survival," *The Journal of Immunology* 168(3), 1060-1068.

Fu, S. et al. (2004) "TGF-β Induces Foxp3+ T-Regulatory Cells from CD4+ CD25—Precursors," *American Journal of Transplantation* 4(10), 1614-1627.

Garlet, G. P. et al. (2005) "Actinobacillus actinomycetemcomitans-induced periodontal disease in mice: patterns of cytokine, chemokine, and chemokine receptor expression and leukocyte migration," *Microbes and Infection* 7(4), 738-747.

Garlet, G. P. et al. (2006) "Expression of suppressors of cytokine signaling in diseased periodontal tissues: a stop signal for disease progression?," *Journal of Periodontal Research* 41(6), 580-584.

Garlet, G. P. et al. (2010) "Regulatory T cells attenuate experimental periodontitis progression in mice," *Journal of Clinical Periodontology* 37(7), 591-600.

Garlet, G. P. et al. (2006) "Cytokine pattern determines the progression of experimental periodontal disease induced by Actinobacillus actinomycetemcomitans through the modulation of MMPs, RANKL, and their physiological inhibitors," *Oral Microbiology and Immunology* 21(1), 12-20.

Garlet, G. P. et al. (2007) "The dual role of p55 tumour necrosis factor-α receptor in Actinobacillus actinomycetemcomitans-induced experimental periodontitis: host protection and tissue destruction," *Clinical & Experimental Immunology* 147(1), 128-138.

Garlet, G. P. et al. (2008) "The essential role of IFN-γ in the control of lethal Aggregatibacter actinomycetemcomitans infection in mice," *Microbes and Infection* 10(5), 489-496.

Garlet, G. P. et al. (2003) "Patterns of chemokines and chemokine receptors expression in different forms of human periodontal disease," *Journal of Periodontal Research* 38(2), 210-217.

Geis Smann, F. et al. (1999) "TGF-β1 Prevents the Noncognate Maturation of Human Dendritic Langerhans Cells," *The Journal of Immunology* 162(8), 4567-4575.

Gershon, R. K. et al. (1971) "Infectious immunological tolerance," *Immunology* 21(6), 903-914.

Graca, L. et al. (2004) "Donor-specific transplantation tolerance: The paradoxical behavior of CD4+CD25+ T cells," *Proceedings of the National Academy of Sciences of the United States of America* 101(27), 10122-10126.

Graca, L. et al. (2002) "Both CD4+CD25+ and CD4+CD25— Regulatory Cells Mediate Dominant Transplantation Tolerance," *The Journal of Immunology* 168(11), 5558-5565.

Grakoui, A. et al. (1999) "The Immunological Synapse: A Molecular Machine Controlling T Cell Activation," *Science* 285(5425), 221.

Graves, D. T. et al. (2003) "The contribution of interleukin-1 and tumor necrosis factor to periodontal tissue destruction," *Journal of Periodontology* 74(3), 391-401.

Graves, D. T. et al. (2008) "The use of rodent models to investigate host—bacteria interactions related to periodontal diseases," *Journal of Clinical Periodontology* 35(2), 89-105.

Green, E. A. et al. (2003) "CD4+CD25+ T regulatory cells control anti-islet CD8+ T cells through TGF-62 —TGF-β receptor interactions in type 1 diabetes," *Proceedings of the National Academy of Sciences* 100(19), 10878-10883.

Gregori, S. et al. (2001) "Regulatory T Cells Induced by 1α,25-Dihydroxyvitamin D3 and Mycophenolate Mofetil Treatment Mediate Transplantation Tolerance," *The Journal of Immunology* 167(4), 1945-1953.

Gurgel, B. C. d. V. et al. (2005) "Selective COX-2 inhibitor reduces bone healing in bone defects," *Brazilian Oral Research* 19(4), 312-316.

Haining, W. N. et al. (2004) "pH-Triggered Microparticles for Peptide Vaccination," *The Journal of Immunology* 173(4), 2578-2585.

Hanes, J. et al. (1995) "Polymer microspheres for vaccine delivery," *Pharmaceutical Biotechnology* 6, 389-412.

Hariharan, S. et al. (2000) "Improved Graft Survival after Renal Transplantation in the United States, 1988 to 1996," *New England Journal of Medicine* 342(9), 605-612.

Hasturk, H. et al. (2007) "Resolvin E1 Regulates Inflammation at the Cellular and Tissue Level and Restores Tissue Homeostasis In Vivo," *The Journal of Immunology* 179(10), 7021-7029.

Herold, K. C. et al. (2002) "Anti-CD3 Monoclonal Antibody in New-Onset Type 1 Diabetes Mellitus," *New England Journal of Medicine* 346(22), 1692-1698.

Hoffmann, P. et al. (2004) "Large-scale in vitro expansion of polyclonal human CD4+CD25high regulatory T cells," *Blood* 104(3), 895-903.

Hori, S. T. S. (2003) "Control of Regulatory T Cell Development by the Transcription Factor Foxp3," *Science* 299(5609), 1057.

Iellem, A. et al. (2001) "Unique Chemotactic Response Profile and Specific Expression of Chemokine Receptors Ccr4 and Ccr8 by Cd4+Cd25+ Regulatory T Cells," *The Journal of Experimental Medicine* 194(6), 847-854.

Inaba, K. et al. (1992) "Generation of large Numbers of dendritic cells from mouse bone marrow cultures supplemented with granulocyte/macrophage colony-stimulating factor," *The Journal of Experimental Medicine* 176(6), 1693-1702.

Itoh, K. et al. (2001) "Bone Morphogenetic Protein 2 Stimulates Osteoclast Differentiation and Survival Supported by Receptor Activator of Nuclear Factor-κB Ligand," *Endocrinology* 142(8), 3656-3662.

Jenkins, M. K. et al. (1990) "Inhibition of antigen-specific proliferation of type 1 murine T cell clones after stimulation with immobilized anti-CD3 monoclonal antibody," *The Journal of Immunology* 144(1), 16-22.

Jhunjhunwala, S. et al. (2012) "Controlled release formulations of IL-2, TGF-β1 and rapamycin for the induction of regulatory T cells," *Journal of Controlled Release* 159(1), 78-84.

Kajita, K. et al. (2007) "Quantitative messenger RNA expression of Toll-like receptors and interferon-αl in gingivitis and periodontitis," *Oral Microbiology and Immunology* 22(6), 398-402.

Karim, M. et al. (2005) "CD25+CD4+ regulatory T cells generated by exposure to a model protein antigen prevent allograft rejection: antigen-specific reactivation in vivo is critical for bystander regulation," *Blood* 105(12), 4871-4877.

(56) References Cited

OTHER PUBLICATIONS

Keegan, M. E. et al. (2004) "Biodegradable Microspheres with Enhanced Capacity for Covalently Bound Surface Ligands," *Macromolecules* 37(26), 9779-9784.
Kempen, D. H. R. et al. (2004) "Development of biodegradable poly(propylene fumarate)/poly(lactic-co-glycolic acid) blend microspheres. II. Controlled drug release and microsphere degradation," *Journal of Biomedical Materials Research Part A* 70A(2), 293-302.
Kingsley, C. I. et al. (2002) "CD25+CD4+ Regulatory T Cells Prevent Graft Rejection: CTLA-4- and IL-10-Dependent Immunoregulation of Alloresponses," *The Journal of Immunology* 168(3), 1080-1086.
Köhler, G. et al. (1975) "Continuous cultures of fused cells secreting antibody of predefined specificity," *Nature* 256(5517), 495-497.
Lee, I. et al. (2005) "Recruitment of Foxp3+ T regulatory cells mediating allograft tolerance depends on the CCR4 chemokine receptor," *The Journal of Experimental Medicine* 201(7), 1037-1044.
Levings, M. K. et al. (2001) "Human Cd25+Cd4+ T Regulatory Cells Suppress Naive and Memory T Cell Proliferation and Can Be Expanded in Vitro without Loss of Function," *The Journal of Experimental Medicine* 193(11), 1295-1302.
Li, Y. et al. (1999) "Blocking both signal 1 and signal 2 of T-cell activation prevents apoptosis of alloreactive T cells and induction of peripheral allograft tolerance," *Nature Medicine* 5(11), 1298-1302.
Lim, H. W. et al. (2006) "Regulation of Trafficking Receptor Expression in Human Forkhead Box P3+ Regulatory T Cells," *The Journal of Immunology* 177(2), 840-851.
Little, S. R. et al. (2004) "Poly-β amino ester-containing microparticles enhance the activity of nonviral genetic vaccines," *Proceedings of the National Academy of Sciences of the United States of America* 101(26), 9534-9539.
Lorentzon, M. et al. (2005) "Reduced Bone Mineral Density in SOCS-2-Deficient Mice," *Pediatric Research* 57(2), 223-226.
Lu, L. et al.(2000) "Controlled release of transforming growth factor β1 from biodegradable polymer microparticles," *Journal of Biomedical Materials Research* 50(3), 440-451.
Mahnke, K. et al. (2003) "Induction of CD4+/CD25+ regulatory T cells by targeting of antigens to immature dendritic cells," *Blood* 101(12), 4862-4869.
Martin, T. J. et al. (2005) "Osteoclast-derived activity in the coupling of bone formation to resorption," *Trends in Molecular Medicine* 11(2), 76-81.
Matzinger, P. (2002) "The Danger Model: A Renewed Sense of Self," *Science* 296(5566), 301.
Matzinger, P. et al. (1989) "Does T-cell tolerance require a dedicated antigen-presenting cell?," *Nature* 338(6210), 74-76.
Merck, E. et al. (2006) "Ligation of the FcRγ Chain-Associated Human Osteoclast-Associated Receptor Enhances the Proinflammatory Responses of Human Monocytes and Neutrophils," *The Journal of Immunology* 176(5), 3149-3156.
Mescher, M. F. (1992) "Surface contact requirements for activation of cytotoxic T lymphocytes," *The Journal of Immunology* 149(7), 2402-2405.
Monks, C. R. F. et al. (1998) "Three-dimensional segregation of supramolecular activation clusters in T cells," *Nature* 395(6697), 82-86.
Mundy, G. R. (1999) "Cellular and molecular regulation of bone turnover," *Bone* 24(5, Supplement 1), 35S-38S.
Nakamura, H. et al. (2008) "Lack of Toll-like receptor 4 decreases lipopolysaccharide-induced bone resorption in C3H/HeJ mice in vivo," *Oral Microbiology and Immunology* 23(3), 190-195.
Nonnenmacher, C. et al. (2003) "DNA from Periodontopathogenic Bacteria Is Immunostimulatory for Mouse and Human Immune Cells," *Infection and Immunity* 71(2), 850-856.
O'Donnell, P. B. et al. (1997) "Preparation of microspheres by the solvent evaporation technique," *Advanced Drug Delivery Reviews* 28(1), 25-42.
Offenbacher, S. et al. (2005) "A perspective on the potential cardioprotective benefits of periodontal therapy," *American Heart Journal* 149(6), 950-954.
Ouyang, X. et al. (2006) "SOCS-2 interferes with myotube formation and potentiates osteoblast differentiation through upregulation of JunB in C2C12 cells," *Journal of Cellular Physiology* 207(2), 428-436.
Pardoll, D. (2003) "Does the Immune System See Tumors as Foreign or Self?," *Annual Review of Immunology* 21(1), 807-839.
Pennsylvania Department of Health. (2002) Status of Oral Health in Pennsylvania, (Pennsylvania Department of Health, Ed.).
Perez, V. L. et al. (1997) "Induction of Peripheral T Cell Tolerance In Vivo Requires CTLA-4 Engagement," *Immunity* 6(4), 411-417.
Pfeilschifter, J. et al. (1987) "Modulation of type beta transforming growth factor activity in bone cultures by osteotropic hormones," *Proceedings of the National Academy of Sciences* 84(7), 2024-2028.
Piccirillo, C. A. et al. (2002) "CD4+CD25+ Regulatory T Cells Can Mediate Suppressor Function in the Absence of Transforming Growth Factor β1 Production and Responsiveness," *The Journal of Experimental Medicine* 196(2), 237-246.
Pietra, B. A. et al. (2000) "Immunosuppression for pediatric cardiac transplantation in the modern era," *Progress in Pediatric Cardiology* 11(2), 115-129.
Pischon, N. et al. (2008) "Association among rheumatoid arthritis, oral hygiene, and periodontitis.," *Journal of Periodontology* 79(6), 979-986.
Ragazzo, J. L. et al. (2001) "Costimulation via lymphocyte function-associated antigen 1 in the absence of CD28 ligation promotes anergy of näive CD4+ T cells," *Proceedings of the National Academy of Sciences* 98(1), 241-246.
Raimondi, G. et al. (2006) "Regulated Compartmentalization of Programmed Cell Death-1 Discriminates CD4+CD25+ Resting Regulatory T Cells from Activated T Cells," *The Journal of Immunology* 176(5), 2808-2816.
Ribeiro, F. V. et al. (2006) "Selective Cyclooxygenase-2 Inhibitor May Impair Bone Healing Around Titanium Implants in Rats," *Journal of Periodontology* 77(10), 1731-1735.
Riley, J. L. et al. (2009) "Human T Regulatory Cell Therapy: Take a Billion or So and Call Me in the Morning," *Immunity* 30(5), 656-665.
Rosenberg, a. S. (1991) in *Current Protocols in Immunology* (Coligan, J. E., et al., Eds.), pp. 4.4.01—04.04.12, John Wiley and Sons, New York.
Rothstein, S. N. et al. (2008) "A simple model framework for the prediction of controlled release from bulk eroding polymer matrices," *Journal of Materials Chemistry* 18(16), 1873-1880.
Rothstein, S. N. et al. (2009) "A unified mathematical model for the prediction of controlled release from surface and bulk eroding polymer matrices," *Biomaterials* 30(8), 1657-1664.
Sakaguchi, S. et al. (1995) "Immunologic self-tolerance maintained by activated T cells expressing IL-2 receptor alpha-chains (CD25). Breakdown of a single mechanism of self-tolerance causes various autoimmune diseases," *The Journal of Immunology* 155(3), 1151-1164.
Sakhalkar, H. S. et al. (2003) "Leukocyte-inspired biodegradable particles that selectively and avidly adhere to inflamed endothelium in vitro and in vivo," *Proceedings of the National Academy of Sciences* 100(26), 15895-15900.
Salomon, B. et al. (2000) "B7/CD28 Costimulation Is Essential for the Homeostasis of the CD4+CD25+ Immunoregulatory T Cells that Control Autoimmune Diabetes," *Immunity* 12(4), 431-440.
Sather, B. D. et al. (2007) "Altering the distribution of Foxp3+ regulatory T cells results in tissue-specific inflammatory disease," *The Journal of Experimental Medicine* 204(6), 1335-1347.
Schor, H. et al. (2000) "Modulation of leukocyte behavior by an inflamed extracellular matrix," *Developmental Immunology* 7(2-4), 227-238.
Seymour, G. J. et al. (2007) "Relationship between periodontal infections and systemic disease," *Clinical Microbiology & Infection* 13(S4), 3-10.
Simon, A. M. et al. (2002) "Cyclo-Oxygenase 2 Function Is Essential for Bone Fracture Healing," *Journal of Bone and Mineral Research* 17(6), 963-976.

(56) References Cited

OTHER PUBLICATIONS

Steenblock, E. R. et al. (2008) "A Comprehensive Platform for Ex Vivo T-cell Expansion Based on Biodegradable Polymeric Artificial Antigen-presenting Cells," *Molecular Therapy* 16(4), 765-772.
Steinman, R. M. et al. (2003) "Tolerogenic Dendritic Cells," *Annual Review of Immunology* 21(1), 685-711.
Steinman, R. M. et al. (2002) "Avoiding horror autotoxicus: The importance of dendritic cells in peripheral T cell tolerance," *Proceedings of the National Academy of Sciences* 99(1), 351-358.
Suda, T. et al. (1992) "Modulation of Osteoclast Differentiation," *Endocrine Reviews* 13(1), 66-80.
Taams, L. S. et al. (2002) "Antigen-specific T cell suppression by human CD4+CD25+ regulatory T cells," *European Journal of Immunology* 32(6), 1621-1630.
Takahashi, N. et al. (1988) "Osteoblastic Cells Are Involved in Osteoclast Formation," *Endocrinology* 123(5), 2600-2602.
Takahashi, N. et al. (1991) "Deficiency of Osteoclasts in Osteopetrotic Mice Is Due to a Defect in the Local Microenvironment Provided by Osteoblastic Cells," Endocrinology 128(4), 1792-1796.
Tang, Q. et al. (2008) "The Foxp3+ regulatory T cell: a jack of all trades, master of regulation," *Nature Immunology* 9(3), 239-244.
Taubman, M. A. et al. (2005) "Immune Response: The Key to Bone Resorption in Periodontal Disease," *Journal of Periodontology* 76(11-s), 2033-2041.
Taylor, P. A. et al. (2002) "Tolerance induction of alloreactive T cells via ex vivo blockade of the CD40:CD40L costimulatory pathway results in the generation of a potent immune regulatory cell," *Blood* 99(12), 4601-4609.
Taylor, P. A. et al. (2002) "The infusion of ex vivo activated and expanded CD4+CD25+ immune regulatory cells inhibits graft-versus-host disease lethality," *Blood* 99(10), 3493-3499.
Teitelbaum, S. L. (2000) "Bone Resorption by Osteoclasts," *Science* 289(5484), 1504.
Thomas, T. T. et al. (2004) "Microparticulate formulations for the controlled release of interleukin-2," *Journal of Pharmaceutical Sciences* 93(5), 1100-1109.
Udagawa, N. et al. (2000) "Osteoprotegerin Produced by Osteoblasts Is an Important Regulator in Osteoclast Development and Function," *Endocrinology* 141(9), 3478-3484.
Van Maurik, A. et al. (2002) "Cutting Edge: CD4+CD25+ Alloantigen-Specific Immunoregulatory Cells That Can Prevent CD8+ T Cell-Mediated Graft Rejection: Implications for Anti-CD154 Immunotherapy," *The Journal of Immunology* 169(10), 5401-5404.
Vignali, D. A. A. et al. (2008) "How regulatory T cells work," *Nature Reviews Immunology* 8(7), 523-532.
Volkmann, A. et al. (1997) "Antigen-presenting cells in the thymus that can negatively select MHC class II-restricted T cells recognizing a circulating self antigen," *The Journal of Immunology* 158(2), 693-706.
Vuolteenaho, K. et al. (2008) "Non-Steroidal Anti-Inflammatory Drugs, Cyclooxygenase-2 and the Bone Healing Process," *Basic & Clinical Pharmacology & Toxicology* 102(1), 10-14.
Walker, M. R. et al. (2003) "Induction of FoxP3 and acquisition of T regulatory activity by stimulated human CD4+CD25—T cells," *The Journal of Clinical Investigation* 112(9), 1437-1443.
Wang, Z. et al. (2006) "Use of the Inhibitory Effect of Apoptotic Cells on Dendritic Cells for Graft Survival Via T-Cell Deletion and Regulatory T Cells," *American Journal of Transplantation* 6(6), 1297-1311.
Wilkinson, P. C. et al. (1994) "Chemoattractant activity of IL-2 for human lymphocytes: a requirement for the IL-2 receptor beta-chain," *Immunology* 82(1), 134-139.
Williams, R. C. et al. (2001) "Treatment of Periodontitis by Local Administration of Minocycline Microspheres: A Controlled Trial," *Journal of Periodontology* 72(11), 1535-1544.
Yamagiwa, S. et al. (2001) "A Role for TGF-β in the Generation and Expansion of CD4+CD25+ Regulatory T Cells from Human Peripheral Blood," *The Journal of Immunology* 166(12), 7282-7289.
Yu, J. J. et al. (2007) "An essential role for IL-17 in preventing pathogen-initiated bone destruction: recruitment of neutrophils to inflamed bone requires IL-17 receptor-dependent signals," *Blood* 109(9), 3794-3802.
Zhang, N. et al. (2009) "Regulatory T Cells Sequentially Migrate from Inflamed Tissues to Draining Lymph Nodes to Suppress the Alloimmune Response," *Immunity* 30(3), 458-469.
Zhang, X. et al. (2004) "Short- and Long-Term Effects of IL-1 and TNF Antagonists on Periodontal Wound Healing," *The Journal of Immunology* 173(5), 3514-3523.
Zhang, Z. et al. (1996) "Pattern of liver, kidney, heart, and intestine allograft rejection in different mouse strain combinations," *Transplantation* 62(9), 1267-1272.
Zhao, C. et al. (2006) "Bidirectional ephrinB2-EphB4 signaling controls bone homeostasis," *Cell Metabolism* 4(2), 111-121.
Zhao, X. et al. (2005) "Directed cell migration via chemoattractants released from degradable microspheres," *Biomaterials* 26(24), 5048-5063.
Zorn, E. et al. (2006) "IL-2 regulates FOXP3 expression in human CD4+CD25+ regulatory T cells through a STAT-dependent mechanism and induces the expansion of these cells in vivo," *Blood* 108(5), 1571-1579.
PCT International Search Report of International Application No. PCT/US2010/041463 dated Oct. 12, 2010.

\* cited by examiner

A.

B.

ARTIFICIAL CELL CONSTRUCTS FOR CELLULAR MANIPULATION

FIELD OF THE INVENTION

The present invention is related to the field of inducing immunological tolerance by specifically manipulating immune-related cells. Such immunological tolerance may be induced by providing biomimetic artificial cells that bypass native immunological cells. For example, biomimetic artificial cell compositions are contemplated which comprise soluble factors that activate specific immune-related blood cells, including, but not limited to, macrophages and/or monocytes. Such factors may comprise chemoattractant factors. These biomimetic artificial particles may further present a specific biomimetic surface pattern that results in a targeted cell response such that the particles represent artificial presenting cells.

BACKGROUND

The science of transplantation, now half of a century old, has dramatically increased and improved the life of many individuals, including many children, with end stage diseases. Recent advancements in immunosuppressive agents have substantially decreased rejection of allografts over the past decade and a half in the United States. Hariharan et al., *N Engl J Med* 342, 605-612 (2000); and First, M. R., *Transplant Proc* 34:1369-1371 (2002). However, to avoid both episodes of acute rejection and the initiation of chronic rejection following transplantation, immunosuppressive drugs must be administered over the entire life of the organ recipient. Consequences of this long-term administration are profound, including undesirable side effects, increasing the risk of infection, autoimmunity, heart disease, diabetes, and cancer. The chronic administration of these immunosuppressive drugs (especially when give systemically) lead to toxicity and significant side effects, thereby leaving the patient vulnerable to a variety of diseases and systemic organ failure.

The most desirable alternative to this extended state of vulnerability would be to render the patient's immune system to effectively suppress immune activation without systemic immunosuppression. In this case, no further immunosuppressant drug treatment would be necessary. Furthermore, the recipient's immune system would otherwise function normally, being capable of combating pathogens and malignant tumor cells. What is needed in the art are compositions and methods to induce permanent immunological tolerance by stimulating immunosuppressive regulatory cells.

SUMMARY OF THE INVENTION

The present invention is related to the field of inducing immunological tolerance by specifically manipulating immune-related cells. Such immunological tolerance may be induced by providing biomimetic artificial cells that bypass native immunological cells. For example, biomimetic artificial cell compositions are contemplated which comprise soluble factors that activate specific immune-related blood cells, including, but not limited to, macrophages and/or monocytes. Such factors may comprise chemoattractant factors. These biomimetic artificial particles may further present a specific biomimetic surface pattern that results in a targeted cell response such that the particles represent artificial presenting cells.

In one embodiment, the present invention contemplates an artificial particle comprising a plurality of soluble and surface bound regulatory T-cell factors. In one embodiment, the artificial particle comprises an artificial presenting cell. In one embodiment, the factors comprise regulatory T cell stimulatory factors. In one embodiment, the factors comprise regulatory T cell inducing factors. In one embodiment, the factors comprise regulatory T cell chemoattractant factors. In one embodiment, the soluble factors undergo controlled released. In one embodiment, the controlled release is a short term release. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the controlled release is a long term release. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year. In one embodiment, the surface bound factors comprises a biomimetic surface pattern. In one embodiment, the biomimetic surface pattern comprises an immunological synapse. In one embodiment, the artificial presenting cell take a shape selected from the group consisting of a sphere, a square, a rectangle, a triangle, a trapezoid, a hexagon, an octagon, or a tetrahedron.

In one embodiment, the present invention contemplates an artificial particle comprising at least one soluble $T_{reg}$ cell factor and at least one surface bound $T_{reg}$ cell factor, wherein said surface bound factor is displayed in a non-random pattern. In one embodiment, the artificial particle comprises an artificial presenting cell. In one embodiment, the at least one soluble or surface bound Treg cell factor comprises a regulatory T cell stimulatory factor. In one embodiment, the at least one soluble or surface bound Treg cell factor comprises a regulatory T cell inducing factor. In one embodiment, the at least one soluble or surface bound Treg cell factor comprises a regulatory T cell chemoattractant factor. In one embodiment, the artificial presenting cell further comprises a functionalized polymer, wherein said polymer encapsulates the soluble factor. In one embodiment, the artificial presenting cell further comprises compartments, wherein said compartments comprise the at least one soluble factor. In one embodiment, the artificial presenting cell is biodegradable such that the soluble factor undergoes controlled release. In one embodiment, the soluble factor comprises CCL22. In one embodiment, the soluble factor comprises IL2. In one embodiment, the soluble factor comprises TGF-β. In one embodiment, the polymer comprises poly-lactic acid-co-glycolic acid (PLGA). In one embodiment, the functionalized polymer non-covalently bonds the soluble factor. In one embodiment, the at least one surface bound $T_{reg}$ stimulating factor forms a biomimetic surface pattern. In one embodiment, the biomimetic surface pattern comprises an immunological synapse. In one embodiment, the synapse comprises a cSMAC region, displayed on an apical portion of the artificial presenting cell. In one embodiment, the synapse comprises a pSMAC region displayed on a tropical region of the artificial presenting cell. In one embodiment, the synapse comprises a dSMAC region displayed on an equatorial portion of the artificial presenting cell. In one embodiment, the cSMAC region comprises CD3 antibodies and/or CD28 antibodies. In one embodiment, the pSMAC region comprises at least one adhesion molecule. In one embodiment, the dSMAC region comprises a CD45 monoclonal antibody. In one embodiment, the functionalized polymer covalently bonds the surface bound regulatory T cell stimulatory factor.

In one embodiment, the present invention contemplates a method, comprising: a) providing, i) an emulsified microparticle comprising at least one soluble $T_{reg}$ cell factor and a functionalized polymer; and ii) at least one surface bound $T_{reg}$ cell factor, wherein the surface bound factor is capable of attaching to the polymer; b) attaching a first surface bound factor to said polymer, wherein an apical region is created; c) attaching a second surface bound factor to said polymer, wherein a tropical region is created; and d) attaching a third surface bound factor to said polymer, wherein an equatorial region is created. In one embodiment, the microparticle comprises an artificial presenting cell. In one embodiment, the at least one soluble or surface bound Treg cell factor comprises a regulatory T cell stimulatory factor. In one embodiment, the at least one soluble or surface bound Treg cell factor comprises a regulatory T cell inducing factor. In one embodiment, the at least one soluble or surface bound Treg cell factor comprises a regulatory T cell chemoattractant factor. In one embodiment, the microparticle is biodegradable such that the soluble factor undergoes controlled release. In one embodiment, the soluble factor comprises CCL22. In one embodiment, the soluble factor comprises IL2. In one embodiment, the soluble factor comprises TGF-β. In one embodiment, the apical, tropical, and equatorial regions comprise a biomimetic pattern. In one embodiment, the biomimetic pattern comprises an immunological synapse. In one embodiment, the first surface bound factor is selected from the group consisting of a CD3 antibody and a CD28 antibody. In one embodiment, the second surface bound factor comprises an adhesion protein. In one embodiment, the third surface bound factor comprises a CD45 antibody. Alternatively, the microparticle may further comprise a CD3 ligand (i.e., MHC) and/or a CD28 ligand.

In one embodiment, the present invention contemplates a method, comprising: a) providing, i) a polymer capable of undergoing emulsification, ii) at least one soluble $T_{reg}$ cell factor, and iii) at least one surface bound $T_{reg}$ cell factor; and b) emulsifying the polymer and the soluble factor such that a biodegradable microparticle is created, such that the soluble factor undergoes controlled release. In one embodiment, the microparticle comprises an artificial presenting cell. In one embodiment, the at least one soluble or surface bound Treg cell factor comprises a regulatory T cell stimulatory factor. In one embodiment, the at least one soluble or surface bound Treg cell factor comprises a regulatory T cell inducing factor. In one embodiment, the at least one soluble or surface bound Treg cell factor comprises a regulatory T cell chemoattractant factor. In one embodiment, the emulsifying may be selected from the group including, but not limited to, precipitation, emulsions, melt casting, spray drying, crystallization, shearing, or milling. In one embodiment, the microparticle is porous. In one embodiment, the microparticle comprises compartment. In one embodiment, the method further comprises step (c) immobilizing a first surface bound stimulatory factor in an apical region of the microparticle. In one embodiment, the method further comprises step (d) immobilizing a second surface bound stimulatory factor in a tropical region of the microparticle. In one embodiment, the method further comprises step (e) immobilizing a third surface stimulatory factor in an equatorial region of the microparticle. In one embodiment, the polymer comprises poly-lactic acid-co-glycolic acid (PLGA). In one embodiment, the soluble stimulatory factor is selected from the group consisting of CCL22, IL2, and TGF-β. In one embodiment, the first surface bound factor is selected from the group consisting of CD3 antibody and CD28 antibody. In one embodiment, the second surface bound factor comprises an adhesion molecule. In one embodiment, the third surface bound factor comprises a CD45 antibody. In one embodiment, the at least one surface bound signaling factor is randomly displayed on the microparticle.

In one embodiment, the present invention contemplates a method, comprising: a) providing, i) a patient having received a tissue transplant, wherein said tissue is capable of immunolgical tolerance; ii) a artificial antigen presenting cell comprising at least one soluble $T_{reg}$ cell factor and at least one surface bound $T_{reg}$ cell factor; and b) administering the artificial antigen presenting cell to the patient under conditions such that an immunological tolerant state is induced in the tissue. In one embodiment, the at least one soluble or surface bound Treg cell factor comprises a regulatory T cell stimulatory factor. In one embodiment, the at least one soluble or surface bound Treg cell factor comprises a regulatory T cell inducing factor. In one embodiment, the at least one soluble or surface bound Treg cell factor comprises a regulatory T cell chemoattractant factor. In one embodiment, the artificial antigen presenting cell is porous. In one embodiment, the immunosuppression is not antigen-specific. In one embodiment, the artificial antigen presenting cell comprises compartments. In one embodiment, the compartments comprise the soluble factor. In one embodiment, the artificial antigen presenting cell is biodegradable, wherein the soluble factor undergoes controlled release. In one embodiment, the controlled release is a short term release. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the controlled release is a long term release. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year. In one embodiment, the method further comprises step (c) inducing a tissue tolerance by the immunosuppressive state. In one embodiment, the tissue tolerance is permanent. In one embodiment, the soluble stimulatory factor is selected from the group consisting of CCL22, IL2, and TGF-β. In one embodiment, the surface bound factors are selected from the group consisting of CD3 antibody, CD28 antibody, an adhesion molecule, and a CD45 antibody. Alternatively, the microparticle may further comprise a CD3 ligand (i.e., MHC) and/or a CD28 ligand.

In one embodiment, the present invention contemplates a kit comprising a container comprising at least one artificial particle suspended in a pharmaceutically acceptable vehicle. In one embodiment, the artificial particle comprises an artificial presenting cell. In one embodiment, the kit further comprises instructions for using the artificial particle to induce immunosuppression in a patient. In one embodiment, the artificial particle comprises at least one encapsulated soluble $T_{reg}$ factor. In one embodiment, the at least one soluble or surface bound Treg cell factor comprises a regulatory T cell stimulatory factor. In one embodiment, the at least one soluble or surface bound Treg cell factor comprises a regulatory T cell inducing factor. In one embodiment, the at least one soluble or surface bound Treg cell factor comprises a regulatory T cell chemoattractant factor. In one embodiment, the soluble factor is selected from the group consisting of CCL22, IL2 or TGF-β.

In one embodiment, the present invention contemplates an artificial osteoblast cell comprising a plurality of soluble and surface bound osteoclast signaling factors. In one embodiment, the soluble signaling factors are controlled released. In one embodiment, the soluble signaling factor comprises MCSF. In one embodiment, the surface bound signaling factor comprises RANK-L, OSCAR-L, and/or ODF. In one embodiment, the controlled release is a short term release. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the controlled release is a long term release. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year. In one embodiment, the surface bound signaling factors comprises a biomimetic surface pattern. In one embodiment, the biomimetic surface pattern comprises an osteological synapse. In one embodiment, the artificial osteoblast cell take a shape selected from the group consisting of a sphere, a square, a rectangle, a triangle, a trapezoid, a hexagon, an octagon, or a tetrahedron.

In one embodiment, the present invention contemplates an artificial osteoblast cell comprising at least one soluble osteoclast cell signaling factor and at least one surface bound osteoclast cell signaling factor. In one embodiment, the artificial osteoblast cell further comprises a functionalized polymer, wherein said polymer encapsulates the soluble factor. In one embodiment, the artificial osteoblast cell further comprises compartments, wherein said compartments comprise the soluble signaling factor. In one embodiment, the artificial osteoblast cell is biodegradable such that the soluble factor undergoes controlled release. In one embodiment, the soluble factor comprises MCSF. In one embodiment, the polymer comprises poly-lactic acid-co-glycolic acid (PLGA). In one embodiment, the functionalized polymer non-covalently bonds the soluble factor. In one embodiment, the at least one surface bound osteoclast signaling factor forms a biomimetic surface pattern. In one embodiment, the biomimetic surface pattern comprises an osteological synapse. In one embodiment, the surface bound osteoclast signaling factor comprises RANK-L, OSCAR-L, and/or ODF. In one embodiment, the functionalized polymer covalently bonds the surface bound osteoclast cell stimulatory factor.

In one embodiment, the present invention contemplates a method, comprising: a) providing, i) an emulsified microparticle comprising at least one soluble osteoclast cell signaling factor and a functionalized polymer; and ii) at least one surface bound osteoclast cell signaling factor, wherein the surface bound signaling factor is capable of attaching (i.e., for example, by conjugating and/or adsorbing) to the polymer; b) attaching a first surface bound factor to said polymer, wherein a first region is created; c) attaching a second surface bound factor to said polymer, wherein a second region is created; and d) attaching a third surface bound factor to said polymer, wherein a third region is created. In one embodiment, the microparticle is biodegradable such that the soluble factor undergoes controlled release. In one embodiment, the at least one soluble signaling factor comprises MSCF. In one embodiment, the first, second, and third regions comprise a biomimetic pattern. In one embodiment, the biomimetic pattern comprises an osteological synapse. In one embodiment, the first surface bound signaling factor comprises RANK-L, OSCAR-L, and/or ODF.

In one embodiment, the present invention contemplates a method, comprising: a) providing, i) a polymer capable of undergoing emulsification, ii) at least one soluble osteoclast cell signaling factor, and iii) at least one surface bound osteoclast cell signaling factor; and b) emulsifying the polymer and the soluble signaling factor such that a biodegradable microparticle is created, such that the soluble factor undergoes controlled release. In one embodiment, the microparticle is porous. In one embodiment, the microparticle comprises compartments. In one embodiment, the emulsifying may be selected from the group including, but not limited to, precipitation, emulsions, melt casting, spray drying, crystallization, shearing, or milling. In one embodiment, the method further comprises step (c) immobilizing a first surface bound signaling factor in an apical region of the microparticle. In one embodiment, the method further comprises step (d) immobilizing a second surface bound signaling factor in a tropical region of the microparticle. In one embodiment, the method further comprises step (e) immobilizing a third surface signaling factor in an equatorial region of the microparticle. In one embodiment, the polymer comprises poly-lactic acid-co-glycolic acid (PLGA). In one embodiment, the soluble signaling factor comprises MCSF. In one embodiment, the at least one surface bound signaling factor comprises RANK-L, OSCAR-L, and/or ODF. In one embodiment, the at least one surface bound signaling factor is randomly displayed on the microparticle.

In one embodiment, the present invention contemplates a method, comprising: a) providing, i) a patient, wherein said patient is in need of bone healing; ii) an artificial osteoblast cell comprising at least one soluble osteoclast cell signaling factor and at least one surface bound osteoclast cell signaling factor; and b) administering the artificial osteoblast cell to the patient under conditions such that the bone healing is induced in the patient. In one embodiment, the patient has under gone bone surgery. In one embodiment, the patient comprises a bone injury. In one embodiment, the patient comprises a bone disease. In one embodiment, the artificial osteoblast cell is porous. In one embodiment, the artificial osteoblast cell comprises compartments. In one embodiment, the compartments comprise the soluble signaling factor. In one embodiment, the artificial osteoblast cell is biodegradable, wherein the soluble factor undergoes controlled release. In one embodiment, the controlled release is a short term release. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the controlled release is a long term release. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year. In one embodiment, the bone surgery comprises bone replacement including, but not limited to, hip replacement or knee replacement. In one embodiment, the bone surgery comprises bone reconstruction. In one embodiment, the bone surgery comprises bone fracture repair. In one embodiment, the soluble signaling factor comprises MCSF. In one embodiment, the surface bound signaling factor comprises RANK-L, OSCAR-L, and/or ODF.

In one embodiment, the present invention contemplates a kit comprising a container comprising at least one artificial osteoblast cell suspended in a pharmaceutically acceptable vehicle. In one embodiment, the kit further comprises instructions for using the artificial osteoblast cell to induce bone healing in a patient. In one embodiment, the artificial osteoblast cell comprises at least one encapsulated soluble osteoclast signaling factor. In one embodiment, the soluble signaling factor comprises MCSF.

In one embodiment, the present invention contemplates an artificial osteoclast cell comprising a plurality of soluble and surface bound osteoblast signaling factors. In one embodiment, the soluble signaling factors are controllably released. In one embodiment, the soluble signaling factor comprises MIM1. In one embodiment, the surface bound signaling factor comprises EphrinB2 and/or TGF-β. In one embodiment, the controlled release is a short term release. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the controlled release is a long term release. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year. In one embodiment, the surface bound signaling factors comprises a biomimetic surface pattern. In one embodiment, the biomimetic surface pattern comprises an osteological synapse. In one embodiment, the artificial osteoblast cell take a shape selected from the group consisting of a sphere, a square, a rectangle, a triangle, a trapezoid, a hexagon, an octagon, or a tetrahedron.

In one embodiment, the present invention contemplates an artificial osteoclast cell comprising at least one soluble osteoblast cell signaling factor and at least one surface bound osteoblast cell signaling factor. In one embodiment, the artificial osteoclast cell further comprises a functionalized polymer, wherein said polymer encapsulates the soluble factor. In one embodiment, the functionalized polymer comprises a surface polymer. In one embodiment, the artificial osteoclast cell further comprises compartments, wherein said compartments comprise the soluble signaling factor. In one embodiment, the artificial osteoclast cell is biodegradable such that the soluble factor undergoes controlled release. In one embodiment, the soluble factor comprises MIM1. In one embodiment, the polymer comprises poly-lactic acid-co-glycolic acid (PLGA). In one embodiment, the functionalized polymer non-covalently bonds the soluble factor. In one embodiment, the at least one surface bound osteoblast signaling factor forms a biomimetic surface pattern. In one embodiment, the biomimetic surface pattern comprises an osteological synapse. In one embodiment, the surface bound osteoblast signaling factor comprises EphrinB2 and/or TGF-β. In one embodiment, the functionalized polymer covalently bonds the surface bound osteoclast cell stimulatory factor.

In one embodiment, the present invention contemplates a method, comprising: a) providing, i) an emulsified microparticle comprising at least one soluble osteoblast cell signaling factor and a functionalized polymer; and ii) at least one surface bound osteoblast cell signaling factor, wherein the surface bound signaling factor is capable of attaching to the polymer; b) attaching a first surface bound factor to said polymer, wherein an apical region is created; c) attaching a second surface bound factor to said polymer, wherein a tropical region is created; and d) attaching a third surface bound factor to said polymer, wherein an equatorial region is created. In one embodiment, the microparticle is biodegradable such that the soluble factor undergoes controlled release. In one embodiment, the at least one soluble signaling factor comprises MIM1. In one embodiment, the apical, tropical, and equatorial regions comprise a biomimetic pattern. In one embodiment, the biomimetic pattern comprises an osteological synapse. In one embodiment, the first surface bound signaling factor comprises EphrinB2 and/or TGF-β.

In one embodiment, the present invention contemplates a method, comprising: a) providing, i) a polymer capable of undergoing emulsification, ii) at least one soluble osteoblast cell signaling factor, and iii) at least one surface bound osteoblast cell signaling factor; and b) emulsifying the polymer and the soluble signaling factor such that a porous biodegradable microparticle is created, such that the soluble factor undergoes controlled release. In one embodiment, the emulsifying may be selected from the group including, but not limited to, precipitation, emulsions, melt casting, spray drying, crystallization, shearing, or milling. In one embodiment, the method further comprises step (c) immobilizing a first surface bound signaling factor in an apical region of the microparticle. In one embodiment, the method further comprises step (d) immobilizing a second surface bound signaling factor in a tropical region of the microparticle. In one embodiment, the method further comprises step (e) immobilizing a third surface signaling factor in an equatorial region of the microparticle. In one embodiment, the polymer comprises poly-lactic acid-co-glycolic acid (PLGA). In one embodiment, the soluble signaling factor comprises MIM1. In one embodiment, the at least one surface bound signaling factor comprises EphrinB2 and/or TGF-β.

In one embodiment, the present invention contemplates a method, comprising: a) providing, i) a patient having undergone bone surgery, wherein said patient is in need of bone healing; ii) a porous artificial osteoclast cell comprising at least one soluble osteoblast cell signaling factor and at least one surface bound osteoblast cell signaling factor; and b) administering the artificial osteoclast cell to the patient under conditions such that a bone healing is induced in the patient. In one embodiment, the porous artificial osteoclast cell comprises compartments. In one embodiment, the compartments comprise the soluble signaling factor. In one embodiment, the artificial osteoclast cell is biodegradable, wherein the soluble factor undergoes controlled release. In one embodiment, the controlled release is a short term release. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the controlled release is a long term release. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year. In one embodiment, the bone surgery comprises bone replacement including, but not limited to, hip replacement or knee replacement. In one embodiment, the bone surgery comprises bone reconstruction. In one embodiment, the bone surgery comprises bone fracture repair. In one embodiment, the soluble signaling factor comprises MIM1. In one embodiment, the surface bound signaling factor comprises EphrinB2 and/or TGF-β.

In one embodiment, the present invention contemplates a kit comprising a container comprising at least one artificial osteoclast cell suspended in a pharmaceutically acceptable vehicle. In one embodiment, the kit further comprises instructions for using the artificial osteoclast cell to induce bone healing in a patient. In one embodiment, the artificial osteoclast cell comprises at least one encapsulated soluble osteoblast signaling factor. In one embodiment, the soluble signaling factor comprises MIM1.

In one embodiment, the present invention contemplates a method, comprising: a) providing, i) a patient, wherein said patient comprises at least one inflammatory symptom; ii) a microparticle comprising at least one soluble Treg factor; and b) administering the microparticle to the patient under conditions such that the at least one inflammatory symptom is reduced. In one embodiment, the at least one soluble or surface bound Treg factor comprises a regulatory T cell stimulatory factor. In one embodiment, the at least one soluble or surface bound Treg cell factor comprises a regulatory T cell inducing factor. In one embodiment, the at least one soluble or surface bound Treg cell factor comprises a regulatory T cell chemoattractant factor. In one embodiment, the patient has under gone periodontal surgery. In one embodiment, the patient further comprises a tissue injury. In one embodiment, the patient further comprises a periodontal disease. In one embodiment, the patient comprises a cancer disease. In one embodiment, the microparticle is porous. In one embodiment, the microparticle is biodegradable, wherein the Treg chemoattractant factor undergoes controlled release. In one embodiment, the controlled release is a short term release. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the controlled release is a long term release. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year. In one embodiment, the Treg chemoattractant factor comprises CCL22 and/or vasoactive intestinal peptide.

DEFINITIONS

The term "artificial particle" or "artificial construct" as used herein, refers to any fabricated degradable polymer construct that is capable of emulsification to encapsulate soluble factors, wherein the polymer may be functionalized to attached surface bound factors. The constructs may then manipulate native regulatory cells to induce immunological tolerance.

The term "artificial presenting cell" as used herein, refers to any artificial particle or artificial construct that further comprises an immunological synapse.

The term "immunological synapse' as used herein, refers to any specific, non-random, arrangement of biological compounds (i.e., for example, antibodies or soluble proteins) on a biological antigen presenting cell that is complementary to a contacting region on a target cell (i.e., for example, a lymphocyte). For example, an antigen presenting cell may comprise an immunological synapse that resembles a "bull's eye" and has a complementary contact region on a regulatory T cell ($T_{reg}$ cell).

The term, "artificial dendritic cell" or "artificial APC" as used herein, refers to any fabricated degradable, artificial presenting cell using microparticle-based controlled release technology capable of interacting with a regulatory T cell. For example, cell-sized PLGA microparticles may be used to encapsulate soluble factors that are capable of inducing regulatory T cells to induce immunosuppression. For investigational studies, the soluble factors may be labeled with monoclonal antibodies (i.e., for example, fluorescent labels).

The term "artificial osteoblast cell", as used herein, refers to any fabricated degradable microparticle having controlled release technology capable of interacting with an osteoclast cell. For example, cell-sized PLGA microparticles may be used to encapsulate soluble factors that are capable of inducing osteoclasts to initiate bone healing. For investigational studies, the soluble factors may be labeled with monoclonal antibodies (i.e., for example, fluorescent labels).

The term "artificial osteoclast cell", as used herein, refers to any fabricated degradable microparticle having controlled release technology capable of interacting with an osteoblast cell. For example, cell-sized PLGA microparticles may be used to encapsulate soluble factors that are capable of inducing osteoblasts to modulate bone healing. For investigational studies, the soluble factors may be labeled with monoclonal antibodies (i.e., for example, fluorescent labels).

The term "soluble regulatory T cell stimulating factors" as used herein, refers to any biological agent (i.e., for example, a protein, hormone, drug etc.) capable of interacting with $T_{reg}$ cells that may become encapsulated within a polymer-based microparticle (i.e., for example, an artificial antigen presenting cell) and undergo controlled release during the degradation of the microparticle. Such soluble factors may be, for example, CCL22, IL2, or TGFβ.

The term "soluble osteoclast signaling factor" as used herein, refers to any biological agent (i.e., for example, a protein, hormone, drug etc) capable of interacting with osteoclast cells that may become encapsulated within a polymer-based microparticle (i.e., for example, an artificial osteoblast cell) an undergo controlled release during the degradation of the microparticle. Such soluble factors may be for example, MIM-1.

The term, "surface bound regulatory T cell stimulating factors" as used herein, refers to any biological agent (i.e., for example, a protein, hormone, drug etc.) capable of interacting with $T_{reg}$ cells, that are attached to the surface of a polymer-based microparticle (i.e., for example, an artificial antigen presenting cell) and are not released during the degradation of the microparticle. Such surface factors may be, for example, CD3 antibody, CD28 antibody, or adhesion molecules.

The term, "surface bound osteoclast signaling factors" as used herein, refers to any biological agent (i.e., for example, a protein, hormone, drug etc.) capable of interacting with osteoclast cells that are attached to the surface of a polymer-based microparticle (i.e., for example, an artificial antigen presenting cell) and are not released during the degradation of the microparticle. Such surface factors may be, for example, RANK-L.

The term "biomimetic" as used herein, refers to any artificial or synthetic construct that has a similar biological effect as a native biological compound. Such similar effects may be due to similarities is size, shape, or specific (i.e., non-random) display of receptors, antibodies, or other active biological compounds. Such shapes include, but are not limited to, a circle, a square, a rectangle, a triangle, a trapezoid, a hexagon, an octagon, or a tetrahedron.

The term, "microparticle" as used herein, refers to any microscopic carrier to which a compound or drug may be attached. Preferably, microparticles contemplated by this invention are capable of formulations having controlled release properties.

The term "PLGA" as used herein, refers to mixtures of polymers or copolymers of lactic acid and glycolic acid. As used herein, lactide polymers are chemically equivalent to lactic acid polymer and glycolide polymers are chemically equivalent to glycolic acid polymers. In one embodiment, PLGA contemplates an alternating mixture of lactide and glycolide polymers, and is referred to as a poly(lactide-co-glycolide) polymer.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The term "biodegradable" as used herein, refers to any material that can be acted upon biochemically by living cells or organisms, or processes thereof, including water, and broken down into lower molecular weight products such that the molecular structure has been altered.

The term "controlled release" as used herein, refers to the escape of any attached or encapsulated factor at a predetermined rate. For example, a controlled release of a factor may occur resulting from the predicable biodegradation of a polymer particle (i.e., for example, an artificial antigen presenting cell). The rate of biodegradation may be predetermined by altering the polymer composition and/or ratio's comprising the particle. Consequently, the controlled release may be short term or the controlled release may be long term. In one embodiment, the short term release is between 30 minutes-1 hour. In one embodiment, the short term release is between 1 hour-3 hours. In one embodiment, the short term release is between 3 hours-10 hours. In one embodiment, the short term release is between 10 hours-24 hours. In one embodiment, the long term release is between 24 hours-36 hours. In one embodiment, the long term release is between 3 days-7 days. In one embodiment, the long term release is between 7 days-1 month. In one embodiment, the long term release is between 1 month-6 months. In one embodiment, the long term release is between 6 months-1 year. In one embodiment, the long term release is at least one year.

The term "emulsification" as used herein, refers to any process that mixes together at least two compounds that are not naturally miscible together. For example, an emulsification process may utilize agents (i.e., emulsifiers) that facilitate the co-solubility of immiscible compounds. For example, emulsification may include methods that use techniques including, but not limited to, precipitation, emulsions, melt casting, spray drying, crystallization, shearing, or milling.

The term "polymer" as used herein, refers to any compound of high molecular weight derived either by the addition of many smaller molecules, such as PLGA, or by the condensation of many smaller molecules with the elimination of water, alcohol, or the like.

The term "functionalized polymer" as used herein, refers to any polymer were the terminal moiety has been chemically altered to facilitate the attachment of other chemicals and or compounds (i.e., for example, proteins, antibodies, hormones, drugs, etc.). For example, the terminal moiety may include, but is not limited to, a carboxylic acid, an amine, a sulfide, a hydroxyl etc.

The term "immobilization" as used herein, refers a state where a biological compound is fixed in position as a complex and is unable to move without the movement of the complex.

The term "attached" as used herein, refers to any interaction between a medium or carrier and a compound. Attachment may be reversible or irreversible. Such attachment may be, but is not limited to, covalent bonding, ionic bonding, Van de Waal forces or friction, and the like. A compound is attached to a medium or carrier if it is impregnated, incorporated, coated, in suspension with, emulsified with, in solution with, mixed with, etc.

The term "covalent bond" as used herein, refers to a close association between at least two atoms, wherein the atoms share electrons in specific atomic orbital paths.

The term "non-covalent bond" as used herein, refers to a close association between at least two atoms, wherein the atoms do not share electrons.

The term "patient" as used herein, is a human or animal and need not be hospitalized. For example, out-patients, persons in nursing homes are "patients."

The term "tissue transplant" as used herein, refers to any replacement of a tissue and/or organ within an individual with a similar tissue and/or organ from a different individual. In some cases, the individuals are from the same species. In other cases, the individual are from different species.

The term "immunological tolerance" as used herein, refers to any modification of the immune system wherein specific antibodies may not be produced, but the immune system remains responsive to other antigens. For example, specific immune related cells including, but not limited to, $T_{reg}$ cells, osteoclasts, and/or osteoblasts may be stimulated to induce immunosuppression. Such "immunological tolerance" may also be capable of controlling autoimmune diseases including, but not limited to, arthritis, Type I diabetes. Such "immunological tolerance" may also be capable of controlling inflammatory diseases including, but not limited to, periodontal disease.

The term "administered" or "administering" a compound or drug, as used herein, refers to any method of providing a compound or drug to a patient such that the compound or drug has its intended effect on the patient. For example, one method of administering is by an indirect mechanism using a medical device such as, but not limited to a catheter, spray gun, syringe etc. A second exemplary method of administering is by a direct mechanism such as, oral ingestion, transdermal patch, topical, inhalation, suppository etc.

The term, "supramolecular activation clusters (SMACs)" as used herein, refer to a topologically complex, and discretely organized, arrangement of antigen presenting cell surface proteins and/or soluble proteins. SMACs may be comprised of a plurality of regions having localized density of specific surface proteins and/or soluble proteins (i.e., for example, central SMAC (cSMAC), peripheral SMAC (pSMAC), or distal SMAC (dSMAC). In general, the surface proteins comprise cell surface antibodies and/or receptors, while the soluble proteins comprise ligands directed to activating certain lymphocytes (i.e., for example, a regulatory T cell).

The term "apical region" as used herein, refers to the top of a sphere and spreading circumferentially from between approximately 1 degree to 30 degrees from a polar axis. In one embodiment, the apical region may spread circumferentially from between approximately 5 degrees to 20 degrees from a polar axis. In one embodiment, the apical region may spread circumferentially from between approximately 10 degrees to 15 degrees from a polar axis.

The term "tropical region" as used herein, refers to a circumferential region of a sphere located between approximately 30-70 degrees from a polar axis. In one embodiment, the tropical region may spread circumferentially from between approximately 35 degrees to 60 degrees from a polar axis. In one embodiment, the tropical region may spread circumferentially from between approximately 40 degrees to 50 degrees from a polar axis.

The term "equatorial region" as used herein, refers to a circumferential region of a sphere located between approximately 70-90 degrees from a polar axis. In one embodiment, the equatorial region may spread circumferentially from between approximately 75 degrees to 85 degrees from a polar axis. In one embodiment, the equatorial region may spread circumferentially from between approximately 87 degrees to 93 degrees from a polar axis.

The term "random" as used herein, refers to a stochastic arrangement of objects formed without definite aim, purpose, method, or adherence to a prior arrangement; or in a haphazard way.

The term "non-random" as used herein, refers to a non-stochastic arrangement of objects with a definite aim, purpose, method and adheres to a prior conceived pattern.

The term "chemoattractant factor" as used herein, refers to any compound and/or molecule that induces movement of chemotactic cells in the direction of its highest concentration. For example, a chemoattractant factor may include, but is not limited to, CCL22 and/or vasoactive intestinal peptide (VIP).

The term "chemotactic cells" as used herein, refers to any biological cell exhibiting chemotaxis, wherein the chemotactic cells direct their movements according to certain chemicals in their environment.

BRIEF DESCRIPTION OF THE FIGURES

The patent application file contains at least one drawing executed in color. Copies of this patent or patent application publication with color drawing (s) will be provided by the office upon request and payment of the necessary fee.

FIG. 15A shows the external porous structure of a microparticle.

FIG. 15B shows the internal structure of the microparticle displaying the inner pockets created by a water-in-oil emulsion.

FIG. 18A: Histograms depicting the absence of CCR4 expression on naïve CD4+ T cells but its presence on activated CD4+ T cells, as determined by flow cytometry.

FIG. 18B: Transwell migration assays show significantly greater migration of activated regulatory and effector CD4+ T cells when compared to respective populations of naïve cells at different concentrations of CCL22. (*p<0.05, one-tailed Students 't' test)

FIG. 18C: Expression of CCL22 is enhanced in CD4+ cells in the presence FoxP3 in comparison to the absence of FoxP3.

FIG. 19A shows a representative schematic describing one experimental design for live animal imaging. Luc+ Treg indicates a Treg population isolated from transgenic mice constitutively expressing the luciferase gene.

FIG. 19B presents exemplary data showing representative fluorescence and luminescence images obtained at day 7 post injection, fluorescence images were used to outline areas of particle localization (i.e., for example, with Pro Living Image® 2.60.1) and these outlines were superimposed onto luminescence images taken with the mouse in the exact same position to demonstrate co-localization of Tregs and CCL22 microparticles.

FIG. 19C presents exemplary data showing kinetics of Treg migration towards the injection sites; average radiance measurements obtained from the luminescence images are displayed as a ratio of CCL2 microparticles to Blank microparticles (BlankMP). Error Bars=Standard Deviation; n=3.

DETAILED DESCRIPTION OF THE INVENTION

Figure 1:
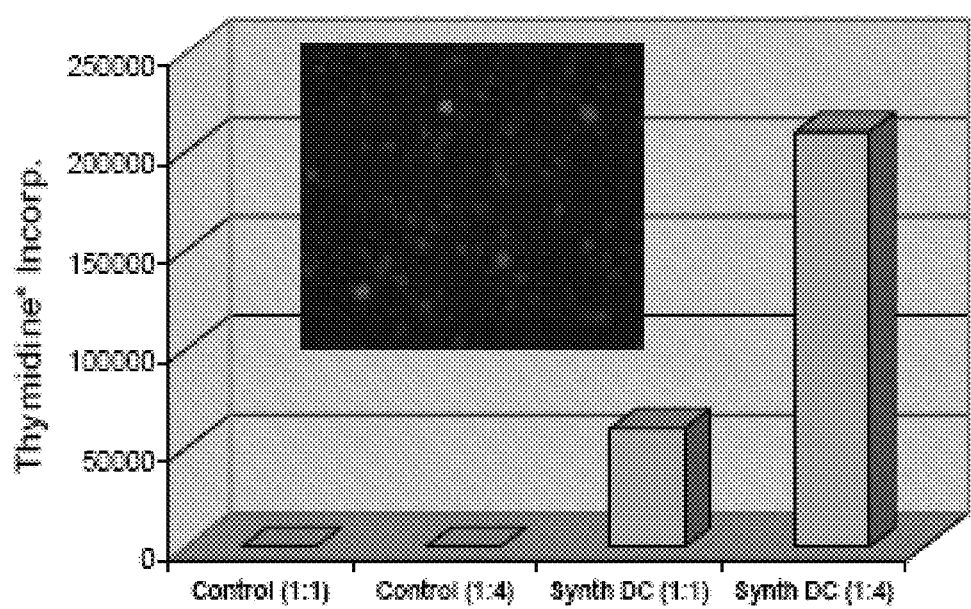
FIG. 1 provides exemplary data showing a $T_{reg}$ proliferative dose response induced by degradable particles with randomly attached CD3 antibodies and CD28 antibodies (ratio=1:1 or 1:4 cells/particle). Proliferation was measured by tritiated thymidine incorporation. Controls are equivalent amounts of soluble antibody (control). Inset: FITC labeled CD3 and CD28 antibodies for visualization)

The present invention is related to the field of inducing immunological tolerance by specifically manipulating immune-related cells. Such immunological tolerance may be induced by providing biomimetic artificial particles that bypass native immunological cells. For example, biomimetic artificial particle compositions are contemplated which comprise soluble factors that activate specific immune-related blood cells, including, but not limited to, macrophages and/or monocytes. Such factors may comprise chemoattractant factors. These biomimetic artificial particles may further present a specific biomimetic surface pattern that results in a targeted cell response such that the particles represent artificial presenting cells.

The present invention contemplates artificial particles such that a synthetic construct may be capable of presenting the same released/secreted and/or chemically-bound/plasma membrane-bound compounds (i.e., for example, soluble proteins, antibodies, receptors, hormones etc.) as actual living cells, and is not limited to modulating the immune system (i.e., for example, modulation of bone healing, tissue inflammation and/or tumor regression). The present invention contemplates various embodiments wherein these artificial constructs replace biological cell-cell interactions within the processes of many biological functions including, but not limited to, wound healing, restoration from a diseased state, or enhancement in normal function of cellular processes.

In one embodiment, the present invention contemplates an investigational platform capable of testing the in vivo roles and efficiencies of both soluble secreted and surface bound $T_{reg}$ cell factors. Such Treg cell factors may including but not limited to stimulatory factor, inducing factor, or chemoattractant factors. In one embodiment, the platform comprises an in vivo testing platform (i.e., for example, an in vivo mouse model). In one embodiment, the platform comprises an in vitro testing platform (i.e., for example, a primary cell culture). These models are capable of evaluating various combinations of membrane surface factors and/or soluble releasable factors that are attached to and/or encapsulated within, a biodegradable, microparticle construct that stimulates $T_{reg}$ cells and induces allograft tolerance. Although it is not necessary to understand the mechanism of an invention, it is believed that these biodegradable microparticle constructs may act as "artificial antigen presenting cells" that comprise a biomimetic immunological synapse and encapsulate and controllably release soluble factors that stimulate $T_{reg}$ cell stimulation, proliferation, and chemotaxis. Hoffmann et al., *Blood* 104, 895-903 (2004); Green et al., *Proc Natl Acad Sci USA* 100: 10878-10883 (2003); Curiel et al., *Nat Med* 10:942-949 (2004); and Belghith et al., *Nat Med* 9:1202-1208 (2003). Further, the constructs are capable of presenting surface-bound monoclonal antibodies (mAb) specific for $T_{reg}$ cell surface activation factors.

I. Immunological Tolerance

In developing a strategy to replace and/or decrease post-transplant immunosuppressant therapy, "reprogramming" the immune system to selectively accept a foreign antigen without an systemic immune down-regulation is seen as a desirable option. This state may be referred to as a permanent immunological tolerance. One modulator of immunological tolerance is suspected to be regulatory T-cells ($T_{reg}$). $T_{reg}$ cells have been shown to be capable of antigen-independent immune suppression and can be activated by immature or tumor-manipulated dendritic cells, thereby inducing immunosuppression. In vitro, $T_{reg}$ cells respond to several known soluble factors and even latex beads coated with monoclonal antibodies specific for several $T_{reg}$ cell surface receptors. Tumors actively secrete compounds to modulate regulatory T-cells so as to evade immune recognition. Although not intuitively obvious, it is believed that the induction of permanent allograft tolerance may be achieved by mimicking tumor-induced immunosuppression.

CD4+CD25+ regulatory T-cells are believed to express the CCR4 receptor which binds to the chemokine CCL22. CCL22 was reported to be involved in the migration of regulatory T-cells to tumor sites because tumors also actively secrete CCL22. Curiel et al., *Nat Med* 10:942-949 (2004). This represents just one of the methods that tumors have for evading immune recognition. Evasion of an immune response provides for tumor survival given that many of its basic biological features such as genetic instability, invasive growth, and tissue disruption are inherently pro-inflammatory. Besides attracting regulatory T-cells to its vicinity, tumors are believed to also have the ability to influence biological antigen presenting cells (i.e., for example, biological dendritic cells) to down-regulate processing and presentation of tumor associated antigens, inhibit co-stimulatory expression (i.e. retain immature phenotype), and alter their cytokine secretion profile towards immune tolerance. Pardoll, D., *Annual Review of Immunology* 21:807-839 (2003). It has been reported that tumors also secrete TGF-β, which may influence regulatory T-cell mediated tolerance. Chen et al., *Proc Natl Acad Sci USA* 102: 419-424 (2005). Although it is not necessary to understand the mechanism of an invention, it is believed that these other mechanisms similar to those of tumor immune evasion and survival may also be useful in inducing allograft tolerance.

Control over the induction of immunological tolerance would afford permanent allograft acceptance, bypassing a lifelong regimen of immunosuppressive agents. Although it is not necessary to understand the mechanism of an invention, it is believed that this tolerance can be mediated by activating suppressive regulatory lymphocytes (i.e., for example, regulatory T cells).

In one embodiment, the present invention contemplates a therapeutically-relevant, modular platform to deliver multiple soluble factors and membrane surface-bound factors. In one embodiment, these factors are delivered in vivo by artificial particles into the vicinity of regulatory T cells ($T_{reg}$ cells). In one embodiment, the delivered factors modulate $T_{reg}$ cell proliferation. In one embodiment, the delivered factors modulate $T_{reg}$ cell immunosuppressive capacity. In one embodiment, the delivered factors induce Treg cell chemotaxis. In one embodiment, the platform is delivered in vivo. In one embodiment, the platform comprises a biocompatible and/or biodegradable synthetic construct, such as an artificial antigen presenting cell (aAPC). In one embodiment, the aAPC is approximately the size of a biological cell. In one embodiment, the aAPC comprises covalently-bound monoclonal antibodies and/or encapsulated soluble cytokines/chemokines. In one embodiment, the antibodies and cytokine/chemokines stimulate lymphocyte proliferation. In one embodiment, the lymphocyte stimulation is performed in vitro. In one embodiment, the lymphocyte stimulation is performed in vivo.

In one embodiment, the present invention contemplates a construct comprising a pattern of membrane surface factors such that the pattern mimics a biological dendritic cell/regulatory T-cell immunological synapse (IS). In one embodiment, the pattern increases the stimulatory capacity of the construct. In one embodiment, the synapse comprises a "bull's-eye" pattern. In one embodiment, the "bull's-eye" pattern comprises an apical region and an equatorial region. In one embodiment, the pattern further comprises a region between the apical and equatorial regions.

In one embodiment, the present invention contemplates a method for creating an artificial biomimetic immunological synapse. In one embodiment, the synapse is discrete and topologically complex. In one embodiment, the synapse comprises at least two immunosuppressive factors. In one embodiment, the synapse is located on the surface of an artificial presenting cell. In one embodiment, the synapse comprises a "bull's-eye" pattern. In one embodiment, the "bull's-eye" pattern comprises an apical region and an equatorial region. In one embodiment, the pattern further comprises a region between the apical and equatorial regions.

A. Tolerogenic Cells

The biological processes whereby tolerance is induced involve the suppression or deletion of alloreactive T-cells which would otherwise destroy an allograft. This process is thought to be mediated by a subset of regulatory T-cells which represent 5-10% of all peripheral CD4+ lymphocytes. Mahnke et al., *Blood* 101:4862-4869 (2003).

Suppressive lymphocyte involvement in immune response was first suggested in the early 1970s. Gershon et al., *Immunology* 21:903-914 (1971). Recently, however, a suppressive regulatory T-cell ($T_{reg}$) has been implicated in the development of immune tolerance. For example, a population of these lymphocytes that express high levels of CD25, the α subunit of the IL2 receptor, have been reported as an immune suppressor. Sakaguchi et al., *J Immunol* 155:1151-1164 (1995).

$T_{reg}$ cells also express a unique transcription factor called FoxP3, which is thought to be required for the development of $T_{reg}$ suppressive capacity and is a recognized marker for $T_{reg}$ cells. Hori et al., *Science* 299:1057-1061 (2003); and Fontenot et al., *Nat Immunol* 4:330-336 (2003). Furthermore, it is believed that the extent of expression of this transcription factor can correlate with the suppressive capacity and activation state of a $T_{reg}$ cell. It has been shown that transfer of the gene for FoxP3 into cells which are CD4+ CD25− confers regulatory capacity which is otherwise absent. Fontenot et al., *Nat Immunol* 4:330-336 (2003). $T_{reg}$ cells may also express high levels of CTLA-4 (i.e., for example, CD152) which may also be involved in their regulatory capacity as this molecule can bind to the B7 class of co-stimulatory molecules in place of CD28 thereby resulting in the production of transforming growth factor-β, or TGF-β. Perez et al., *Immunity* 6:411-417 (1997). TGF-β, along with engagement of the T-cell receptor, has been demonstrated to differentiate naïve, peripheral CD4+CD25− T-cells into CD4+CD25+ cells with suppressive capacity, suggesting that this factor may be important for the in vivo generation and maintenance of $T_{reg}$ cells. Walker et al., *J Clin Invest* 112:1437-1443 (2003). Regulatory T-cells are also believed to express chemokine receptors including, but not limited to, CCR4 and CCR8, rendering them fully capable of migration (i.e., for example, by chemotaxis) to a site of inflammation or to the lymph nodes upon appropriate signaling. Iellem et al., *J Exp Med* 194:847-853 (2001).

Mechanisms of action used by regulatory T-cells in promoting tolerance in vivo has been a topic of dispute. Some believe that cell-to-cell contact between $T_{reg}$ cells and the alloreactive lymphocytes provide the activation stimulus that results in immunosuppression. Others believe that specific stimulatory factors (i.e., for example, soluble factors and/or membrane surface bound factors) which have been shown to be secreted from regulatory T-cells may be responsible for contact-independent suppression (i.e., for example, TGF-β, IL-10, CTLA-4, and IL-4). For example, studies which support the latter hypothesis demonstrate that: i) $T_{reg}$ activation by TNF-β may be blocked by monoclonal antibodies (Belghith et al., *Nat Med* 9:1202-1208 (2003); and ii) $T_{reg}$ activation is diminished in TGF-β receptor knock-out mice (Green et al., *Proc Natl Acad Sci USA* 100:10878-10883 (2003)). However, it has been reported that suppression by $T_{reg}$ cells in vitro is not inhibited by blocking TGF-β and suggest a cellular contact dependant mechanism. Piccirillo et al., *J Exp Med* 196:237-246 (2002).

Nevertheless, one interesting notion regarding the method of $T_{reg}$ cell suppression which is gaining popular acceptance is an antigen independent suppression mechanism, known as "bystander regulation". Several new reports are providing evidence for "bystander regulation" which opposes a previous hypothesis that regulatory T-cells preferentially mediate immunosuppression in an antigen specific manner. Graca et al., *Proc Natl Acad Sci USA* 101:10122-10126 (2004); and Karim et al., *Blood* 105:4871-4877 (2005). In particular, Karim et al. reported that CD25+CD4+ $T_{reg}$ cells generated by nominal antigens under cover of anti-CD4 monoclonal antibody treatments were fully capable of tolerizing mice to cardiac allografts comprised of completely different antigens. Therefore, although most studies show that T-cell receptor stimulation seems to be involved in tolerization, antigen specificity may or may not be limiting in the overall effects of immunosuppression induced by regulatory T-cells. The data presented herein suggest that $T_{reg}$ cell immunosuppression may be meditated through a combination of contact dependant and independent mechanisms.

1. Antigen Presenting Cells

In one embodiment, the present invention contemplates methods that would reconcile the apparently conflicting in vitro and in vivo data regarding cytokine-dependent suppressive capacity. In one embodiment, the method comprises using cell types that are not present in the in vitro experimental models (i.e., for example, a co-mediator cell). Although it is not necessary to understand the mechanism of an invention, it is believed that these co-mediator cells may secrete their own immunomodulating cytokines or act in other suppressive capacities at the same time as regulatory T-cells. For example, a co-mediator cell may comprise an antigen presenting cells (APCs). Antigen presenting cells are also referred to as dendritic cells and have been shown to have a tolerogenic capacity. Matzinger et al., *Nature* 338: 74-76 (1989); Steinman et al., *Proc Natl Acad Sci USA* 99:351-358 (2002); Brocker et al., *J Exp Med* 185:541-550 (1997); and Volkmann et al., *J Immunol* 158:693-706 (1997).

APCs and lymphocytes may interact at a contact point in accordance with a "two signal" model of stimulation. For example, the presence of T-cell receptor (TCR)/Major Histocompatibility Complex (MHC) engagement (i.e., for example, Signal 1) without the presence of a proper co-stimulatory molecule engagement (i.e., for example, Signal 2) may lead to lymphocyte progression toward a state of anergy or deletion through apoptosis. In support of this hypothesis, it has been demonstrated that engagement of the T-cell receptor using monoclonal antibodies specific for CD3 (i.e., for example, T-cell receptor subunit believed responsible for signal transduction), in the absence of co-stimulation, led to long lasting proliferative unresponsiveness in murine T-cell clones. Jenkins et al., *J Immunol* 144: 16-22 (1990).

Dendritic cells (i.e., for example, APCs) in an immature state (i.e. that have not been stimulated by inflammatory factors) have been observed to possess a low level expression of co-stimulatory molecules while still maintaining expression of MHC Class I and II. These immature dendritic cells have a high capacity to take up material by receptor-mediated endocytosis, pinocytosis, and phagocytosis and are thought to survey the periphery and constantly process and present self-antigen. These observations suggest that an immunological tolerant state is maintained in the absence of co-stimulatory molecules even when self-antigen is persistently presented. Consequently, it would be reasonable to believe that the presence of co-stimulatory molecules represent danger signals. Matzinger, P. *Science* 296:301-305 (2002). Although it is not necessary to understand the mechanism of an invention, it is believed that this would explain why autoimmunity develops when the normal, perpetual tolerant state is somehow disrupted.

In light of the above, it is most likely not a coincidence that persistent expression of antigen in the periphery is also thought to be sufficient for generation of regulatory T-cells. Taams et al., *Eur J Immunol* 32:1621-1630 (2002). Furthermore, soluble factors are secreted by $T_{reg}$ cells that generate and maintain APCs in an immature state including, but not limited to: i) IL10 (De Smedt et al., *Eur J Immunol* 27:1229-1235 (1997)); ii) TGF-β (Geissmann et al., *J Immunol* 162:4567-4575 (1999)); and IL4 (Inaba et al., Journal of Experimental Medicine 176:1693-1702 (1992)). On the other hand, others have shown that immature/tolerogenic dendritic cells also have the ability to mediate contact-dependent stimulation of $T_{reg}$ cells. These secreted soluble factors are also suggested to generate and maintain $T_{reg}$ cells thereby creating the possibility for feedback regulation. Steinman et al., *Annu Rev Immunol* 21:685-711 (2003). This feedback mechanism might even extend to the apoptosis of dendritic cells which are already activated or mature by regulatory T-cells. Frasca et al., *J Immunol* 168:1060-1068 (2002). These data suggest that APCs and $T_{reg}$ cells interact to modulate immunotolerance.

The current understanding of biological processes whereby regulatory T-cells ($T_{reg}$) promote tolerance is presented in Table 1.

Although it is not necessary to understand the mechanism of an invention, it is believed that the stimulation, and behavior of, $T_{reg}$ cells can generate immune tolerance. Professional antigen presenting cells (APCs) (i.e., for example, dendritic cells: DCs) have also been shown to have tolerogenic capacity, although the precise mechanism of their suppressive function is unclear. Matzinger et al., *Nature* 338:74 (1989); and Steinman et al., *Proc Natl Acad Sci USA*, 99:351 (2002). A relationship between DCs and $T_{reg}$ cells has been observed where a persistent presentation of antigen by tolerogenic DCs generates $T_{reg}$ cells through both contact-mediated and secreted soluble signal-mediated stimulation. Steinman et al., *Annu Rev Immunol* 21:685 (2003). Thus, APCs might mediate immunosuppression by stimulating $T_{reg}$ cells through a dual pronged mechanism.

Although it is not necessary to understand the mechanism of an invention, it is believed that an artificial particles comprising Treg cell factors should modulate $T_{reg}$ cells in a manner similar to biological antigen presenting cells. For example, a membrane surface presentation (i.e., for example, an immunological synapse) of stimulating protein factors on a biological dendritic cell is not displayed in a random pattern. In one embodiment, the present invention contemplates an artificial antigen presenting cell comprising soluble and/or membrane bound stimulating factors displayed in non-random patterns.

In particular, biological antigen presenting cells have been reported to develop a mature immunological synapse (IS) and are composed of discretely defined spatial regions of receptors. Monks et al., *Nature* 395:82 (1998). Some in the art have termed these regions as supramolecular activation clusters, or SMACs. Grakoui et al., *Science* 285:221 (1999). A central SMAC (cSMAC) region may comprise areas providing factors for TCR stimulation and/or soluble factors for co-stimulation. The cSMAC may be surrounded by at least one peripheral SMAC (pSMAC) region that are usually

TABLE 1

Summary Of $T_{reg}$ Observations

Figure 3:
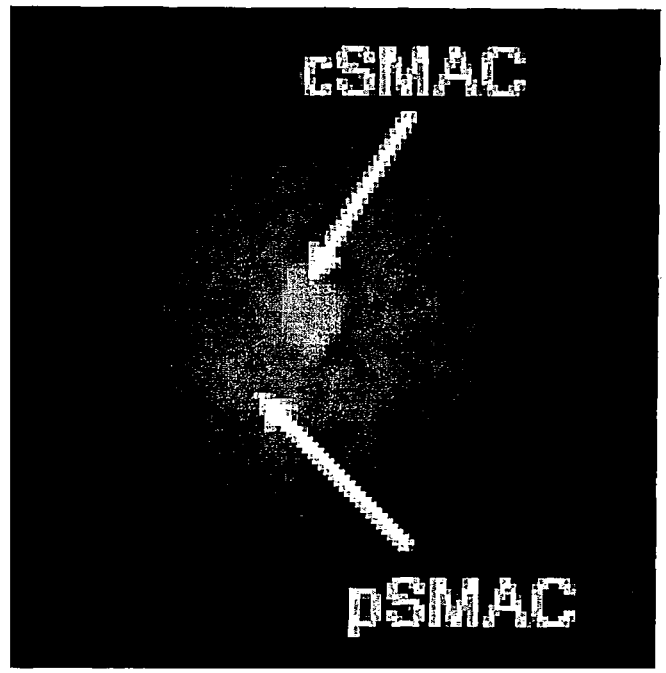
FIG. 3 shows a fluorescent image of a representative "bull's eye" immunological synapse orientation from a biological dendritic cell. Grakoui et al., Science 285:221 (1999).

| Observation | Significance | Reference |
|---|---|---|
| Tolerogenic $T_{reg}$ cells express high surface levels of CD4 & CD25. | These markers can aid in the isolation of $T_{reg}$ cells | Sakaguchi et al., *J Immunol* 155: 1151 (1995). |
| The transcription factor Foxp3 is highly expressed in activated $T_{reg}$. | Activation state of $T_{reg}$ can be determined by measuring Foxp3. | Fontenot et al., *Nat Immunol* 4: 330 (2003). |
| TGF-β1 can generate $T_{reg}$ while inhibiting other T-cells. | TGF-β1 is important to preferential development of $T_{reg}$. | Belghith et al., *Nat Med* 9: 1202 (2003); and Green et al., *PNAS* 100: 10878 (2003). |
| $T_{reg}$ express the chemokine receptors CCR4 and CCR8 and are attracted by their ligands. | Chemokines such as CCL22 may be used to preferentially recruit $T_{reg}$. | Chen et al., *American Journal of Transplantation* 6: 1518 (2006); and Curiel et al., Nat Med 10: 942 (2004). |
| Tolerogenic dendritic cells have been associated with, and have the capacity to stimulate, $T_{reg}$. | Contact-mediated and soluble factor stimulation provided by these APCs can generate $T_{reg}$ | Steinman et al., *Annu Rev Immunol* 21: 685 (2003). |
| $T_{reg}$ stimulated by a particular antigen can mediate immune suppression in the presence of an allograft without this antigen. | $T_{reg}$ are capable of promoting allograft tolerance regardless of the antigen/TCR-stimulus used to generate them. | Karim et al., *Blood* 105: 4871 (2005). |
| Beads coated with mAb specific to CD3 and CD28 in the presence of IL2 were capable of stimulating and proliferating $T_{reg}$ in vitro. | A similar strategy could be utilized in vivo by including soluble factor(s) in a biodegradable format. | Hoffmann et al., *Blood* 104: 895 (2004). | rich in adhesion molecules (i.e., for example, ICAM). Further, pSMACs may be surrounded by a distal SMAC (dSMAC) region that may have, for example, a high CD45 density. Using a dual probe fluorescence imaging technique, the SMAC spatial organization resembles a "bulls-eye". See, FIG. 3.

2. In vitro $T_{reg}$ Stimulation

In vitro testing with primary, regulatory T-cells provides a way to determine if the soluble factors encapsulated within an artificial particle are biologically active. Preferred assays are directly related to the biological activity of the encapsulated factors with respect to their modulatory effects on $T_{reg}$ cells. In vitro primary $T_{reg}$ cells also provide a testing platform for the optimization of artificial particles in preparation for therapeutic in vivo administration.

A method for large scale in vitro expansion of $T_{reg}$ cells has been reported. Hoffmann et al., Blood 104:895 (2004). In this study, the proliferation and suppressive capacity of cultured $T_{reg}$ cells was increased using latex beads randomly coated with soluble IL2 and CD3/CD289 monoclonal antibodies. It was unreported if the $T_{reg}$ cell populations produced by Hoffmann et al. are functionally the same as those produced in vivo by biological antigen presenting cells. Sufficient discrepancies are observed between in vitro and in vivo suppressive mechanisms to indicate that they are not functionally the same. Belghith et al., Nat Med 9:1202 (2003); and Green et al., PNAS 100:10878 (2003). Such a problem in the art identifies a need to study in vivo $T_{reg}$ cell activation. A significant disadvantage of the Hoffmann et al. technique, is that the random distribution stimulatory factors on the latex beads did not present the $T_{reg}$ cells with an SMAC IS complex.

Nonetheless, in vitro data is provided herein demonstrating the stimulatory capacity of synthetic dendritic cells by several subsets of T-cells. For example, primary lymphocytes were harvested and incubated with synthetic dendritic cells and the resulting level of activation were measured.

Commercially available cell isolation kits (i.e., for example, MACS) may be used to harvest CD4+CD25+ $T_{reg}$ and CD4+CD25- helper T-cells from lymph nodes of B6 mice. Once incubated with artificial antigen presenting cells, regulatory T-cells can be examined for proliferative capacity using techniques including, but not limited to, tritiated thymidine incorporation, CSFE dilution, or Flow Cytometry. Cytokine secretion profiles (i.e., for example, IL-2 or IFN-gamma) may be determined using ELISPOT. To assess regulatory T-cell activation the presence of the intracellular transcription factor, FoxP3, may also be measured in permeabilized cells using Flow Cytometry.

To verify the exclusivity of $T_{reg}$ cell stimulation, artificial antigen presenting cells can also be incubated with other lymphocyte populations (CD4+CD25-, and CD8+) which are then tested for known activation markers. Although it is not necessary to understand the mechanism of an invention, it is believed that because of the release of TGF-β1 by aAPCs these non-suppressor cells will not be stimulated and may actually even gain suppressive capacity. Fu et al., Am J Transplant 4:1614 (2004). It is further believed that the removal of CD28 co-stimulation may result in anergy of helper T-cells. Ragazzo et al., PNAS 98:241 (2001). Thus, it is not presumed that a cSMAC region must contain both membrane bound TCR stimulation factors and soluble co-stimulation factors simultaneously to achieve preferential regulatory T-cell activation.

Nonetheless, $T_{reg}$ cells may be studied in vitro using artificial APCs comprising multiple membrane surface-bound stimulatory factors and soluble secretable stimulatory factors. For example, the activity of encapsulated soluble stimulatory factors may be tested using primary $T_{reg}$ cells in vitro by assays measuring effects on cell differentiation, cell proliferation, and/or chemotaxis. In some embodiments, a plurality of aAPC formulations may be used wherein each aAPC formulation comprises a different amount of both surface bound factors and soluble releasable factors. In one embodiment, the present invention contemplates a method comprising identifying an optimized formulation.

3. In Vivo Effects of Artificial Particles on Regulatory T Cells ($T_{regs}$)

In one embodiment, the present invention contemplates a method comprising implanting artificial particles in vivo wherein $T_{reg}$ cells are recruited and/or activated. In one embodiment, the $T_{reg}$ cell recruitment and/or activation induces biological graft tolerance. Although it is not necessary to understand the mechanism of an invention, it is believed that the biological graft tolerance is a result of $T_{reg}$ cell induced immunosuppression.

Before $T_{reg}$ cells can be directly manipulated by an artificial particle, however, they need to be attracted to an artificial particle. In one embodiment, the present invention contemplates an artificial particle comprising an encapsulated chemotactic factor (i.e., for example, CCL22). Alternatively, the $T_{reg}$ cell population may be increased by performing a $T_{reg}$ cell adoptive transfer. This procedure is especially useful during investigational and/or technique verification studies wherein the transferred $T_{reg}$ cells are labeled with green fluorescent protein (i.e., for example, collected from transgenic GFP+ B6 mice). The resulting enriched $T_{reg}$ population in vivo facilitates histological and flow cytometry analyses. Further, an optimization of the chemotactic factor is most likely necessary because of inherent differences between in vivo and in vitro techniques, as discussed above.

The embodiments of the present invention contemplate many transplantation models for use as testing models. In some embodiment, testing models include, but are not limited to, skin allograft or heterotopic heart transplants, and are used to compare high and low amounts of donor derived antigen presenting cells. These donor biological particles may interfere or enhance the function of the artificial particles. However, it should be theoretically feasible to drastically outnumber the biological antigen presenting cells through administration of multiple depot injections near the transplantation site and/or coating the allograft with artificial particles. In one embodiment, a skin allograft testing model is chosen due to the simplicity of the procedure and the ability to use a control syngenic graft on the same animal. In one embodiment, a heterotopic heart transplant testing model is chosen, not only due to its relatively simple procedure and method of data collection, but also because of the consistency in the rejection profile as opposed to liver and kidney transplants.

In one embodiment, the present invention contemplates a method comprising measuring regulatory T cell migration and activation following exposure to synthetic, biodegradable constructs. In one embodiment, the method comprises an in vivo murine model. This model provides unexpected and unpredictable advantages over traditional in vitro models, because, as discussed elsewhere, the behavior of $T_{reg}$ cells in vitro is not believed to be equivalent to that observed in vivo. M. Belghith et al., Nat Med 9:1202 (September, 2003); Green et al., PNAS 100:10878 (2003).

In one embodiment, the present invention contemplates a testing method comprising co-implanting a tissue transplant graft and a plurality of artificial particles in vivo, wherein the artificial particles recruit and activate the $T_{reg}$ cells to induce a permanent graft tolerance. For example, artificial particles may be tested for the ability to recruit and stimulate regulatory T-cells by injecting artificial particles into mice which have been adoptively transferred with GFP+ $T_{reg}$ cells. Imaging studies can then easily identify in vivo localizations of the GFP+ $T_{reg}$ cell following artificial particle injection. Further, various artificial particle formulations may be co-administered at the time of tissue transplantation (i.e., for example, skin allograft or heterotopic heart transplantation) to examine their therapeutic ability to induce allograft tolerance.

In one embodiment, the present invention contemplates an in vivo method comprising manipulating $T_{reg}$ cells using synthetic dendritic cells. In one embodiment, the synthetic dendritic cells stimulate $T_{reg}$, thereby resulting in immunosuppression. Although it is not necessary to understand the mechanism of an invention, it is believed that that synthetic dendritic cells which are approximately 10 μm do not move from the site of implantation given that they are too large to cross the endothelial barrier or redistribute via the reticuloendothelial system. In one embodiment, the method further comprises administering synthetic dendritic cells with encapsulated soluble factors and/or surface factors into a first leg flank of a B6 mouse. In one embodiment, the administering comprises injection. In one embodiment, the injection comprises a subcutaneous injection. In one embodiment, the injection comprises an intramuscular injection. In one embodiment, a second leg flank is injected with a synthetic dendritic cell without encapsulated soluble and/or surface factors (i.e., for example, as a negative control). At 1 Day or 3 Days after the injection(s), mice will be euthanized and skin or muscle will be resected for histological analysis (i.e., for example, staining for $T_{reg}$ cells and Foxp3). Wang et al., *Am J Transplant* 6:1297 (June, 2006). The sensitivity of this protocol can be enhanced by adoptively transferring fluorescent $T_{reg}$ isolated from GFP+ B6 mice into normal B6 mice to increase the number of detectable cells available for chemotaxis.

In one embodiment, the present invention contemplates a method comprising prolonging the survival of a skin allograft using a biomimetic immunosuppressive synthetic dendritic cell.

4. $T_{reg}$ Cells And Transplant Tolerance

The generation of $T_{reg}$ suppressor cells has been attempted in vivo prior to transplantation with the goal of inhibiting allograft rejection. Most of these methods involve the administration of an alloantigen, with the final result being an increase in the number and activation state of regulatory T-cells. In mice, it has been shown that naïve regulatory T-cells still have suppressive capacity, but 10 fold greater quantities are required to promote graft acceptance when compared to populations that have been stimulated prior to transplantation with alloantigen. Graca et al., *J Immunol* 168:5558-5565 (2002). Furthermore, administration of this alloantigen is usually accompanied by CD4 monoclonal antibodies to avoid eliciting a hostile immune response. Kingsley et al., *J Immunol* 168:1080-1086 (2002).

Other monoclonal antibodies which block co-stimulation pathways may also be used to generate regulatory T-cells including, but not limited to, monoclonal antibodies that block CD154-CD40 engagement. van Maurik, A., Herber, M., Wood, K. J. & Jones, N. D. (2002) *J Immunol* 169, 5401-4; Taylor et al., *Blood* 99:4601-4609 (2002). Also, CD-3 monoclonal antibodies were used to generate regulatory T-cells via stimulation through the T-cell receptor (TCR) and was reported to control the progression of diabetes. Herold et al., *N Engl J Med* 346:1692-1698 (2002). Native, immature dendritic cells may be capable of generating CD4+CD25+ $T_{reg}$ cells in vivo if alloantigen is specifically targeted to them by an antibody which binds to DEC205; a receptor involved in the recycling of antigen through late endosomal compartments. Mahnke et al., *Blood* 101:4862-4869 (2003).

Ex vivo expansion and manipulation of tolerogenic cells holds much promise for therapeutic application given their relatively low frequency in peripheral tissues. For this potential to be realized, this expansion would have to maintain an appropriate regulatory phenotype, including the ability to migrate to the correct sites of inflammation and the lymphoid compartments. Attempts at generating regulatory T-cells in vitro have involved stimulation with alloantigen with co-stimulants, such as: i) vitamin D3 and dexamethasone (Barrat et al., *J Exp Med* 195:603-616 (2002)); ii) IL10 (Levings et al., *J Exp Med* 193:1295-302 (2001)); iii) TGF-β (Yamagiwa et al., *J Immunol* 166:7282-7289 (2001)); and iv) IL2 (Taylor et al. *Blood* 99:3493-3499 (2002)). Transfection of T-cell subsets with the gene for FoxP3 in vitro has also endowed regulatory capacity. Fontenot et al., *Nat Immunol* 4:330-336 (2003).

II. Biomimetic Artificial Antigen Presenting Cells

In one embodiment, the present invention contemplates a method comprising fabricating cell-sized, degradable particles (i.e., for example, a synthetic dendritic cell or artificial antigen presenting cell). In one embodiment, the particles release soluble factors. In one embodiment, the particles display surface bound factors in a non-random pattern. In one embodiment, the particles display surface bound factors in a random pattern. In one embodiment, the non-random pattern simulates an immunological synapse. In one embodiment, the synapse comprises a supramolecular activation complex.

In one embodiment, the artificial particle comprises a biodegradable construct thereby providing a controlled release of incorporated and/or attached compounds (i.e., for example, therapeutic agents, antibodies, cytokines, or chemokines). In one embodiment, the particle comprises a degradable polyester including, but not limited to, poly (lactic-co-glycolic) acid (PLGA). PLGA has been used in FDA-approved grafts, sutures, and/or drug delivery microparticulates such as Lupron Depot®. Degradable PLGA polymer microparticles are superior to conventional latex or polystyrene "artificial APCs" because PLGA confers biodegradability. Further, unlike latex and polystyrene polymer particles that only allow surface attachment of proteins, PLGA polymer particles. allow encapsulation of protein cell factors (i.e., for example, IL2, TGF-β, and CCL22) through a double emulsion/solvent evaporation procedure. Odonnell et al., *Advanced Drug Delivery Reviews* 28:25-42 (1997). Further, a controlled release of soluble cell factors from PLGA polymers can be engineered to create an appropriate local concentration of these cell factors, which would be accompanied by cell-to-cell contact with immobilized molecules on the particle surface. Such immobilized molecules (i.e., for example, a monoclonal antibody) can be easily bound to the particle through a streptavidin-biotin linkage using several established chemical techniques. Further, the controlled release of encapsulated one such soluble protein factor for twenty days from microparticles has been demonstrated (i.e., for example, CCL22). See, FIG. 9A. Scanning electron microscopy confirmed the porous nature of the microparticles responsible for the controlled release characteristics. See, FIG. 9B.

Artificial stimulation using randomly coated micron-sized spherical constructs to promote cytotoxic T-cell receptor engagement along with co-stimulation has been used to gain insight into the role of IL2 as a soluble stimulation factor. Mescher et al., *J Immunol* 149:2402-2405 (1992); and Curtsinger et al., *J Immunol Methods* 209:47-57 (1997). When applied to regulatory T-cells, stimulation by randomly coated constructs provided substantial increases in total cell count, but also enhanced suppressive capabilities over non-stimulated naïve CD4+CD25+ cells. Others have shown that randomly coated particles produce expanded and activated regulatory T-cells were polyclonal, and maintained expression of appropriate chemokine receptors. Hoffmann et al., *Blood* 104:895-903 (2004).

Nevertheless, these references using randomly coated particles do not contemplate the specific advantages of creating and using non-randomly patterned artificial presenting cells that specifically mimic biological cell surface protein patterns (i.e., for example, a supramolecular activation complex). In one embodiment, the present invention contemplates fabricating an artificial tolerogenic dendritic cell designed to stimulate a regulatory T-cell. In one embodiment, these cell sized constructs present protein factors capable of both cooperating in TCR engagement and releasing $T_{reg}$ cell co-stimulatory moieties. For example, the constructs are able to contain and controllably release soluble chemokines and proliferation promoting factors. These constructs highly flexible, being capable of modification for both the type, and level, of surface bound and/or soluble releasable stimulating factors. In some embodiments, the use of biodegradable materials will provide uses of these "artificial dendritic cells" for in vivo diagnostics to identify the role of individual $T_{reg}$ cell stimulating factors, and therapeutically to promote allograft tolerance.

A. The Particle Core

In one embodiment, the present invention contemplates a particle comprising CD3 antibodies and CD28 antibodies non-randomly attached to the surface of a poly-lactic-co-glycolic acid (PLGA) particle. In one embodiment, the antibodies are attached by absorption. In one embodiment, the antibodies are attached covalently. In one embodiment, the particles are covalently surface modified with streptavidin. In one embodiment, the particles comprise biotinylated mAb, wherein the mAbs stimulate $T_{reg}$ cells. In one embodiment, the attached antibodies are in a biologically active state. See, FIG. 1.

These biodegradable particles have numerous advantages over $T_{reg}$ cell modulators known in the art, for example: a) particle biodegradability and biocompatibility allow for in vivo investigational and therapeutic use for controlling $T_{reg}$ cells in immune suppression; or 2) such particles are capable of controllably releasing soluble proteins such as cytokines and chemokines from the particle interior while also presenting immobilized protein factors on their surface; and 3) surface-mediated stimulation and release of soluble factors from the same artificial construct closely mimics $T_{reg}$ cell stimulation by biological dendritic cells.

In one embodiment, the particles comprise releaseable soluble factors that preferentially activate different T-cell subsets. In one embodiment, the releasable factors are encapsulated within the particles. Although it is not necessary to understand the mechanism of an invention, it is believed that the releasable factors are controllably released subsequent to particle degradation. In one embodiment, the factor comprises a suppressive cytokine (i.e., for example, TGF-β12). In one embodiment, the factor comprises a $T_{reg}$-preferential cytokine (i.e., for example, CCL-226).

Figure 2:
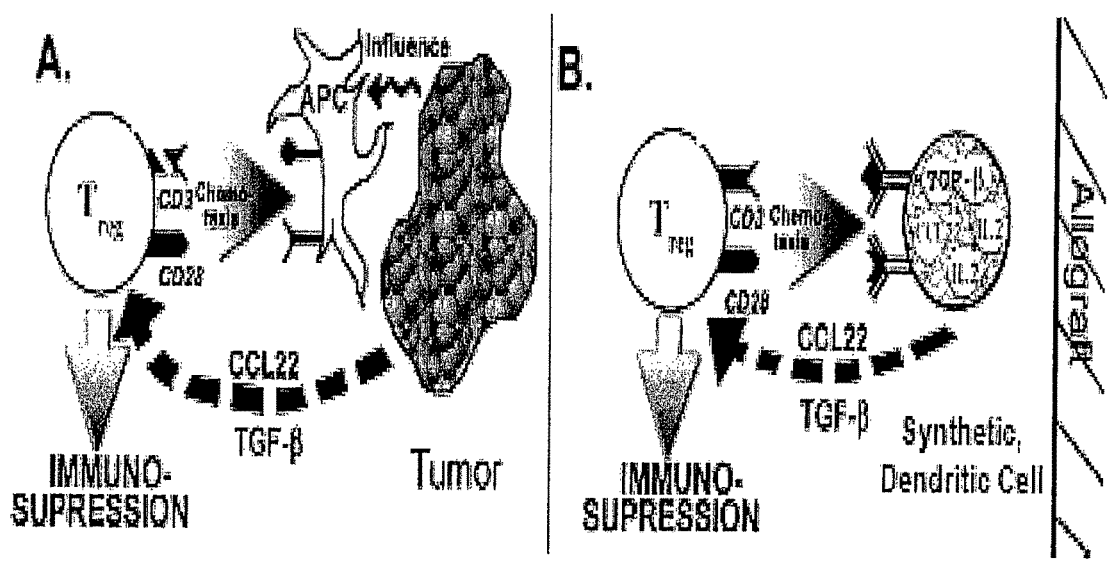
FIG. 2 presents an illustrative embodiment showing how regulatory T cells ($T_{regs}$) are attracted to: (A) a tumor; or (B) an artificial presenting cell (i.e., for example, a synthetic dendritic cell) near the surface of an allograft.

These particles behave similarly to tumor tissues that are believed to actively suppress immune responses by selectively secreting TGF-β12 and/or CCL-226 to attract $T_{reg}$s to their vicinity. Otherwise, a body's normal immune response might otherwise destroy the malignancy. Curiel et al., *Nat Med* 10:942 (2004); and Chen et al., *Proc Natl Acad Sci USA* 102:419 (2005). Although it is not necessary to understand the mechanism of an invention, it is believed that the particles contemplated by the present invention are capable of both delivering the immobilize surface stimulation factors and the secreted soluble stimulation factors to act in a similar manner as tolerogenic biological dendritic cells (i.e., for example, APCs) to influence $T_{reg}$ mediated immunoresponsivity. See, FIG. 2.

B. Artificial Antigen Presenting Cell Surface Protein Patterns

Recent studies have attempted to study IS orientations in vitro using microfabricated, patterned "dots" of CD3 antibody (i.e., providing TCR stimulation) in a field of ICAM adhesion molecules. Doh et al., *Proc Natl Acad Sci USA* 103:5700 (2006). In vitro models have distinct disadvantages, however, because $T_{reg}$ cell stimulation is more pronounced when using a spherical structure as opposed to a flat surface, such as a cell culture dish. Curtsinger et al., *J Immunol Methods* 209: 47 (1997). Further, the in vitro approach provided in Curtsinger et al. does not allow simulation for the study of all three (3) SMAC regions in a mature IS. Especially lacking in Curtsinger et al. is the ability to study biomimetic SMAC regions. Although recent data demonstrate patterns having protein orientations using two (2) factors on a particle surface, a method of precisely orienting a pattern of >2 factors on a particle has yet to be discovered. Chen et al., *Proc Natl Acad Sci USA* 104:11173 (2007).

In one embodiment, the present invention contemplates a method comprising creating a synthetic dendritic cell surface comprising a biomimetic IS pattern. See, FIG. 4. In one embodiment, the IS pattern comprises a cSMAC region. In one embodiment, the IS pattern comprises a pSMAC region. In one embodiment, the IS pattern comprises a dSMAC region. Although it is not necessary to understand the mechanism of an invention, it is believed that this method is analogous to draining water out of a tub filled with bowling balls. After only a fraction of the liquid has drained, the top portion of the ball (having a circular shape, if viewed from above) will have been exposed (thereby making the surface available for a first modification) while the remaining portion is still covered by the water (not available for a first modification). After further draining, an annular ring comprising the first modification and the remaining portion is exposed, thereby making the remaining portion available for labeling with a second factor, thereby creating a second annular ring. This process may be repeated as many times as desired limited only by the size of the ball and the width of the multiple annular rings.

Figure 4A:
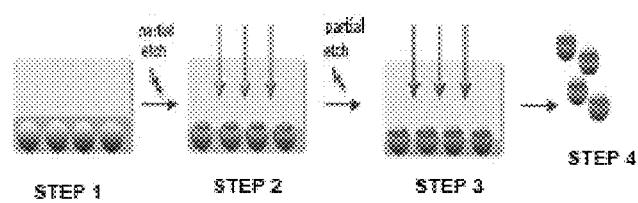
FIG. 4A illustrates one embodiment of a method for fabricating artificial presenting cell construct patterns that mimic a cellular immunological synapse (IS). Step 1: Particles are immersed in PDMS or Resin; Step 2: Etch so that only the top of the particles are exposed and chemically attach ligand (see arrows); Step 3: Etch remainder away and label remainder of particle by chemically attaching $2^{nd}$ ligand (see arrows); and Step 4: Repeat-or-wash and collect.
Figure 4B:
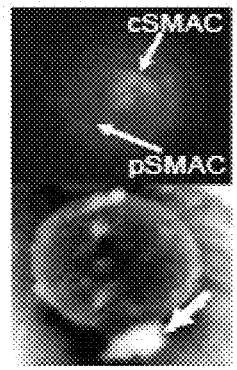
FIG. 4B presents an exemplary fluorescent photomicrograph image of a synthetic dendritic cell comprising a central supramolecular activation complex (cSMAC) region (green/yellow) and a peripheral supramolecular activation complex (pSMAC) region. See, Top Image arrows, respectively. Scanning Electron Microscopic backscatter imaging shows a bright, and intentionally over-labeled, cSMAC region (See, Bottom Image, white arrow=gold-bead labeled protein).

A method for patterning a prototype particle with multiple factor layers was demonstrated using poly-dimethylsiloxane (PDMS). As is known from photolithography techniques, PDMS can be etched by the application of a solvent. This is analogous to partial draining of water from a bathtub full of bowling balls. Using PDMS, a prototype synthetic dendritic cell comprising a "bull's eye" IS was made by surface etching an artificial cSMAC region surrounded by artificial pSMAC region. See. FIG. 4. In one embodiment, the present invention contemplates a method for stimulating $T_{reg}$ cells using "bull's eye" patterned IS-mimetic particles, wherein the stimulation is qualitatively and quantitatively superior to randomly-labeled synthetic dendritic cells.

The above construction of prototype synthetic dendritic cells using dual labels definitively shows preferential labeling in different particle regions. Nonetheless, some factor overlap is present indicated by overlapping fluorescent signals (i.e., a yellow central region indicating the presence of both labels) and some gold-bead labeling in the SEM images outside of the intended central region. These observations may be a result of uneven PDMS etching which may be improved by using techniques that are more easily controllable with respects to speed, distance, and residual matter. For example, a sodium silicate ("liquid-glass") system can provide a more easily controlled etching process by using<5% hydrofluoric acid (HF) evenly applied at a controllable rate of approximately 100 nm per minute resolution (data not shown).

C. Functional Protein Patterns on Synthetic Dendritic Cell Prototypes

The present invention contemplates compositions comprising a fabricated cell-sized, biodegradable particle exhibiting secretable soluble factors and immobilized surface factors displayed in a biomimetic pattern.

In one embodiment, the present invention contemplates a synthetic dendritic cell comprising PLGA microparticles. In one embodiment, the present invention contemplates a method of producing a synthetic dendritic cell comprising encapsulating soluble and/or surface factors into the PLGA microparticles using one of many emulsification and/or encapsulation procedures (i.e., for example, double emulsion). In one embodiment, the synthetic dendritic cells comprise microparticle diameters of approximately 1-1000 µm. In one embodiment, the microparticle diameters are approximately 5-500 µm. In one embodiment, the synthetic dendritic cells comprise microparticle diameters of approximately 10-50 µm. Lu et al., *J Biomed Mater Res* 50:440 (2000). Encapsulation methods are commonly used to load agents into polymer matrices that are capable of releasing factors by modifying parameters including, but not limited to, copolymer ratios and/or molecular weight. Odonnell et al., *Advanced Drug Delivery Reviews* 28:25 (1997).

Encapsulation loading of synthetic dendritic cells can be easily verified by dissolution techniques using sodium hydroxide and/or dimethylsulfoxide followed by protein detection assays such as bicinchoninic acid (BCA) or enzyme linked immunosorbent assay (ELISA) to detect total protein. Fluorescent surface factor labeling determines which construction method (PDMS vs. "liquid glass") produces the most consistent results. For example, three separate labels can be applied using a bioconjugate strategy, for example: i) a first exposed region may be protected with small-molecule biotinylation; ii) a second exposed region may be protected with an asymmetric disulfide (for subsequent thiol exchange) 20; and iii) a third exposed region may be protected with standard N-(3-dimethylaminopropyl)-N'-ethylcarbodiimide hydrochloride (EDC) chemistry.

In one embodiment, the present invention contemplates a method for evaluating three (3) exposed particle regions by fabricating the particles using different formulations. In one embodiment, a formulation comprises cSMAC (CD3 mAb)+pSMAC (ICAM) (2 labels/2 regions) for comparison to formulations created on a flat surface (i.e., for example, an in vitro cell culture dish). In one embodiment, a formulation comprises cSMAC (CD3+CD28 mAbs)+pSMAC (ICAM) (3 labels/2 regions) for comparison with randomly displayed CD3 mAbs and CD28 mAbs particles. In one embodiment, a formulation comprises cSMAC (CD3/CD28)+pSMAC (ICAM)+dSMAC (CD45 mAb) for comparison with a complete synthetic immunological synapse comprising at least three (3) SMACs.

III. Controlled Release of Compounds from Artificial Particles

Controlled release of compounds from microparticles (i.e., for example, PLGA microparticles) fabricated from the double emulsion procedure provide many advantages as an artificial construct for releasing encapsulated compounds as opposed to more traditional compounds such as latex or styrene based particles. PLGA microparticle advantages include, but are not limited to: i) the double emulsion procedure allows for encapsulation of any number of water soluble activation factors; ii) particle size can be easily adjusted based on known fabrication parameters; iii) PLGA is non-toxic, biodegradable, and has properties which allow it to be tuned to adjust release of the encapsulated agents; and 4) the surface of PLGA particles can be easily labeled using EDC (carbodiimide) chemistry.

In one embodiment, the present invention contemplates a method comprising encapsulating and controllably releasing soluble factors while maintaining relatively stable surface presentation of monoclonal antibody. Although it is not necessary to understand the mechanism of an invention, it is believed that $T_{reg}$ cells are attracted towards an artificial particle, engage surface protein stimulation factors, and receive the proper proliferation and maturation signals from secreted soluble proteins at the same time. In one embodiment, the encapsulating comprises at least one soluble secretable factors, including but not limited to, IL2, TGF-β, and CCL22. These factors may be encapsulated individually or in any combination. In one embodiment, the releasing is controlled by using different molecular weight PLGA or through other fabrication parameters including, but not limited to, drug distribution, occlusion radius, amorphicity/crytallinity of the polymer, excipients etc. Rothstein et al., *J Materials Chem* 18:1873-1880 (2008). An empirical process determines the final amounts of factors to be encapsulated given that the appropriate quantity of these factors for optimal stimulation of regulatory T-cells in vivo is yet still unknown.

In one embodiment, the particle surface is covalently labeled to determine the number of functionalized sites capable of attaching the immobilized protein factors. In one embodiment, the labeling comprises 2-pyridyldithioethylamine. In covalent labeling of the particle, it would be desirable to allow for positioning of the surface mediated regulatory T-cell factor(s) (i.e., for example, monoclonal antibodies for CD3 or CD28) in a way which does not covalently link the active site. To achieve this, some embodiments conjugate streptavidin to the particle surface. Although it is not necessary to understand the mechanism of an invention, it is believed that at least one of streptavidin's four active binding sites for biotin will be exposed. Consequently, an artificial particle may be labeled using commercially available biotinylated antibodies specific for many commercially available surface molecules. Alternatively, streptavidin may be thiolated (i.e., for example, by using readily available products such as NHS esters of S-acetyl-thioacetic acid or Trauts reagent) and integrated into the 2-pyridyldithioethylamine labeling embodiment described herein.

In some embodiments, biodegradable polymers pre-labeled with biotin may be used in fabrication of artificial particles. For example, poly(lactic acid) (PLA) copolymers with poly(ethylene glycol) (PEG) are reported to be conjugated with biotin. Cannizzaro et al., *Biotechnol Bioeng*

58:529-535 (1998). Microparticles have been made from these polymers have been reported to produce microparticles having surface binding sites using emulsion/solvent-evaporation techniques. Further, the microparticle surface was successfully labeled using an excess of neutravidin followed by biotinylated monoclonal antibodies and proteins. Sakhalkar et al., *Proc Natl Acad Sci USA* 100:15895-15900 (2003).

IV. Release Characteristics of CCL22

The data presented herein demonstrates that a sustained release of CCL22 was achieved by loading the chemokine into degradable poly(lactic-co-glyoclic) acid (PLGA)—based microparticles (CCL22MP) using a water-oil-water double emulsion-evaporation technique. Zhao et al., *Biomaterials* 26:5048-5063 (2005). Scanning electron micrographs (SEM) of intact microparticles indicates that these microparticles are spherical and slightly porous. FIG. 15A. SEM particle cross-sections also show a plurality of internal structures formed during creation in a water-in-oil primary emulsion. FIG. 15B. The surface of a microparticle comprising CCL22 (CCL22MP) was specifically formulated to be porous, to allow continuous release of chemokine (i.e., for example, release occurring without intermittent periods of lag). Rothstein et al., *J. Mater. Chem.* 18:1873-1880 (2008); Rothstein et al., *Biomaterials* 30:1657-1664 (2009). For example, release experiments performed in phosphate-buffered saline demonstrate a constant release of CCL22 for over 3 weeks. See, FIG. 16. Further, the microparticles were designed to be large enough (i.e., for example, >10 μm) to avoid their uptake by phagocytic cells and to prohibit their movement through capillaries, with consequent immobilization at the site of injection. FIG. 17.

Simultaneously, the ability of CCL22 to attract murine T cells was examined. Expression of chemokine receptors for CCL22 (i.e., for example, the CCR4 receptor) are known to control the ability of cells to respond to CCL22 gradients. Moreover, there is evidence that only activated T cells express the CCR4 receptor. Baatar et al., *Journal of Immunology* 178: 4891-4900 (2007); Lim et al., *Journal of Immunology* 177:840-851 (2006); and Lee et al., *Journal of Experimental Medicine* 201:1037-1044 (2005); and FIG. 18A. The data presented herein show that activated T cells (both regulatory and effector cell populations), but not naïve T cells, migrated towards a CCL22 gradient in vitro using a transwell chamber-based assay, a response that is consistent with their surface receptor expression patterns. FIG. 18B.

Having confirmed that activated Tregs migrate toward a CCL22 gradient and that controlled release formulations could be used to sustain the release of CCL22, the capability of CCL22MPs to attract Tregs in vivo was tested. For example, CCL22-releasing polymeric particles were injected into the triceps surae of FVB mice followed by i.v. infusion of ex vivo activated, alloantigen-specific Tregs (AATregs) that constitutively expressed the luciferase gene. Following an activation stimulus (i.e., for example, an allogeneic-dendritic cell injection) the migration pattern of AATregs could be monitored by non-invasive live animal imaging. FIG. 19A. The data demonstrate that immediately after allogeneic-dendritic cell stimulation (i.e., for example, approximately 4-7 days after injection) a significantly greater number of AATregs were recruited to the site of the CCL22MP injection when compared to an internal control of microparticles lacking CCL22 (BlankMP). FIG. 19B and FIG. 20. Further, upon analyzing the kinetics of migration, it was determined that cellular localization was transient and that within 7 days of the stimulation event, no significant numbers of AATreg persisted at the site of particle injections. See, FIG. 19C.

One explanation of the data is that the decline in AATreg numbers may be due to the absence of stimulatory/inflammatory signals at the site of CCL22MP injection at that time. Presumably, the presence of Treg can be extended in a stimulatory microenvironment, in combination with other survival factors. The potential therapeutic implications of a degradable controlled release formulation capable of recruiting Tregs are manifold. For example, CCL22MP may be used in combination with an infusion of cells expanded ex-vivo. Current pre-clinical data suggest that infusion of freshly-isolated or ex vivo-expanded Tregs can be used to prevent rejection of organ transplants and to suppress autoimmune diseases, but challenges such as obtaining adequate numbers and highly purified populations of Tregs have hindered progress into clinical trials. Brusko et al., *Immunological Reviews* 223:371-390 (2008); and Riley et al., *Immunity* 30:656-665 (2009). Given that the present data suggest that Tregs can be attracted to a local site using CCL22, it may be possible to lower the numbers of injected cells, or potentially, to use populations with lower purity. In one embodiment, the present invention contemplates a method comprising a microparticle population encapsulating CCL22, wherein a controlled release of CCL22 from the microparticle improves tissue transplantation success (i.e., for example, murine pancreatic islet cell transplantation). In one embodiment, the released CCL22 attracts Tregs to the pancreatic islet cells. Zhang et al., *Immunity* 30:458-469 (2009).

Another use of CCL22-containing polymeric microparticles would be to attract naturally occurring Treg populations. If the numbers of recruited Tregs prove sufficient to control adverse immune responses at the site of particle injection, then therapeutic effects could be realized without infusion of ex vivo-expanded Tregs. This hypothesis has been reported within the context of a murine model of periodontitis, a disease that is associated with dissipation of Tregs from the gingival tissues and loss of immune homeostasis. Garlet et al., *Microbes and Infection* 7:738-747 (2005). The data presented herein indicates that administration of CCL22MP leads to local recruitment of FoxP3+ cells to the gingival tissues and corresponding reversal of adverse outcomes associated with periodontitis (infra). Conventional methods of CCL22-based sustained release have disadvantages in that this particular chemokine is known to attract both activated Tregs and activated effector T cells. FIG. 18; and Bromley et al., *Nature Immunology* 9:970-980 (2008); Thus, in some cases it is quite possible that the numbers of recruited Tregs may be insufficient to control the immune response.

However, CCL22-based release formulations can easily be modified to simultaneously release immunosuppressive agents that can suppress the functions of activated effector T cells in situ, thereby assisting the Tregs in controlling adverse immune responses. Additionally, although CCL22 can attract both activated Tregs and effector T cells in vitro, studies in vivo suggest that CCL22 production and release associated with tumors or long-surviving allografts results in local immunosuppression. Curiel et al., *Nature Medicine* 10:942-949 (2004); and Lee et al., *Journal of Experimental Medicine* 201:1037-1044 (2005), respectively. Although it is not necessary to understand the mechanism of an invention, it is believed that this CCL22-associated effect may be due to an enriched population of recruitable Tregs in the periphery when compared to activated effector Tcells, or where equivalent numbers of both populations are recruited and the suppressive effect of Tregs is dominant.

In conclusion, the local attraction of Tregs in vivo using chemokine-loaded sustained delivery vehicles has been demonstrated. Controlled release microparticle formulations as contemplated herein are particularly useful as a modular platform for therapeutic development as well as a tool to study Treg-dependent modulation of immune responses in situ.

V. CCL22 Microparticle Therapy

Figure 17:
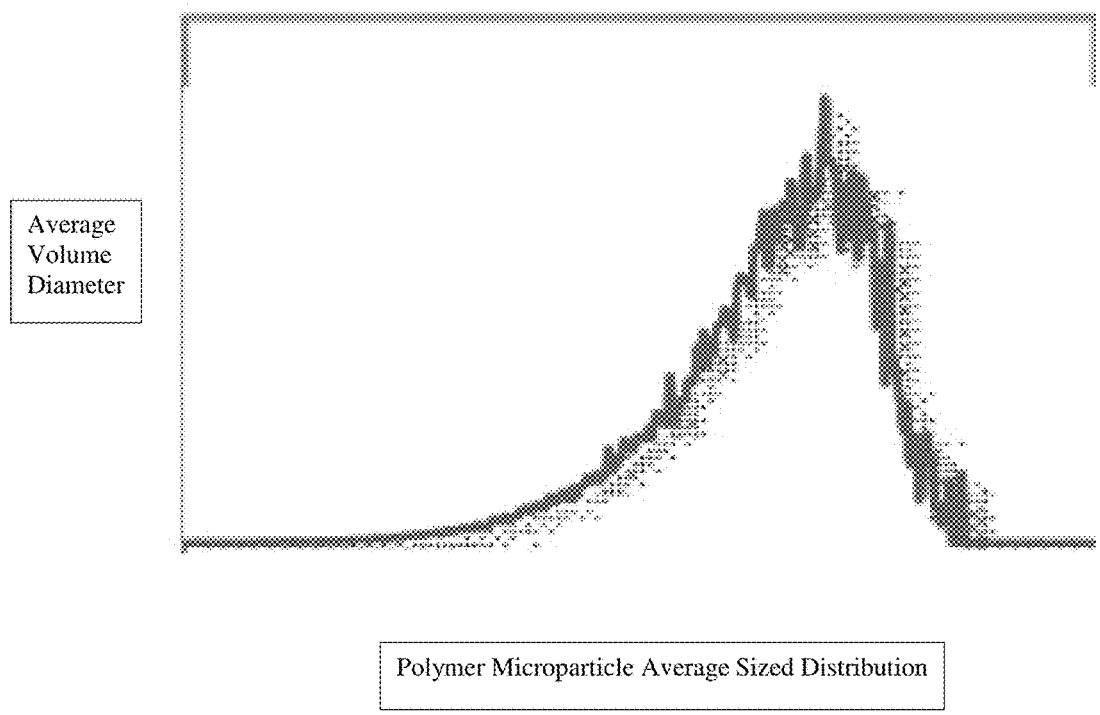
FIG. 17 presents exemplary data showing a representative volume of an averaged sized distribution of microparticles comprising CCL22 determined by average volume diameter measurements. Error Bars=Standard Error of the Mean; n=6.
Figure 18:
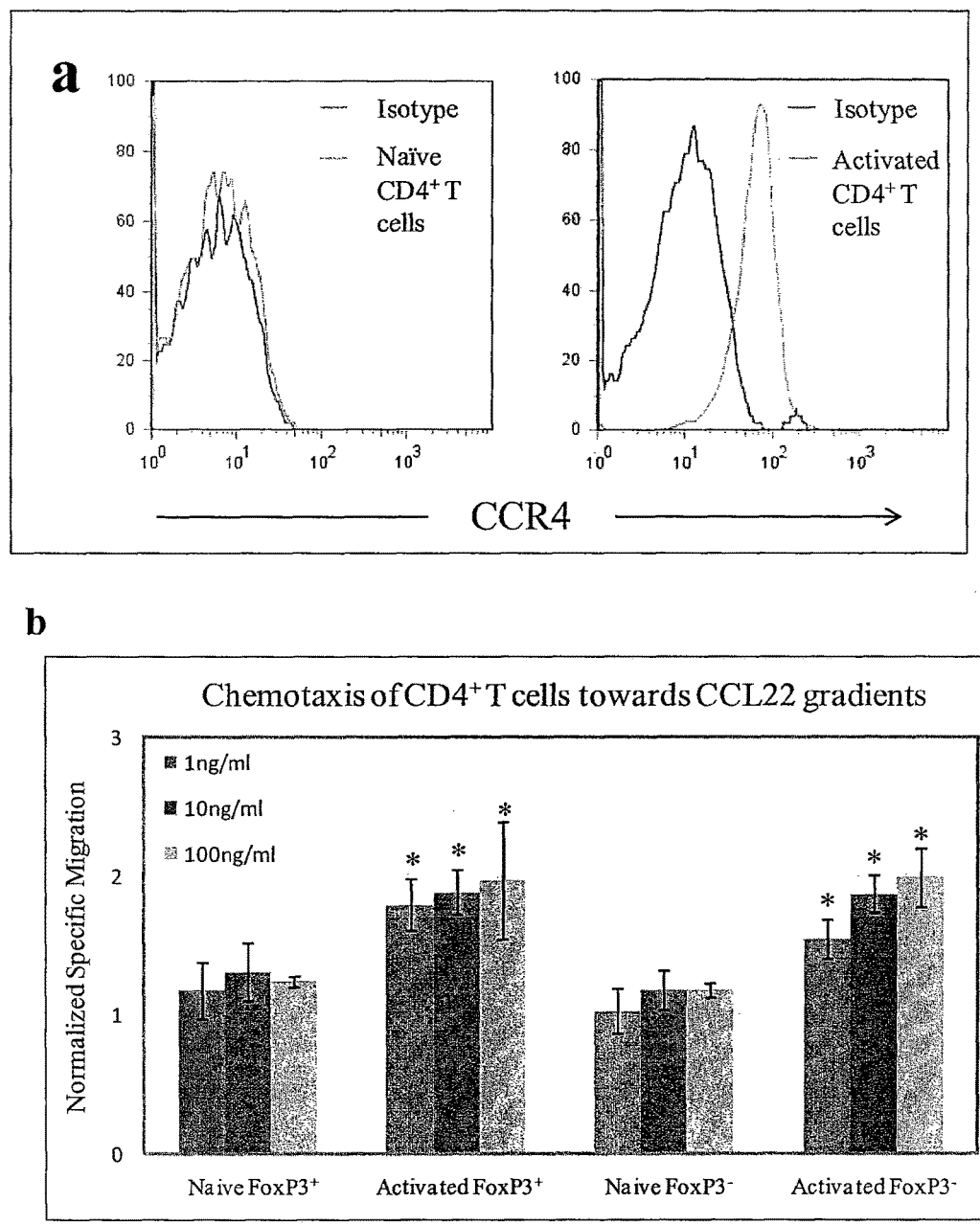
FIG. 18 presents exemplary data showing CCR4 expression and in vitro transwell migration assay.
Figure 18:
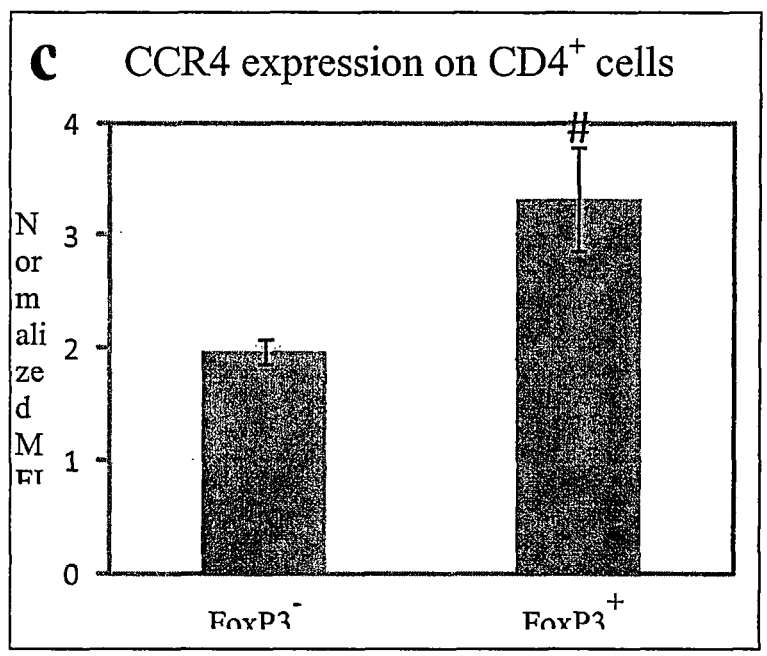
Figure 19:
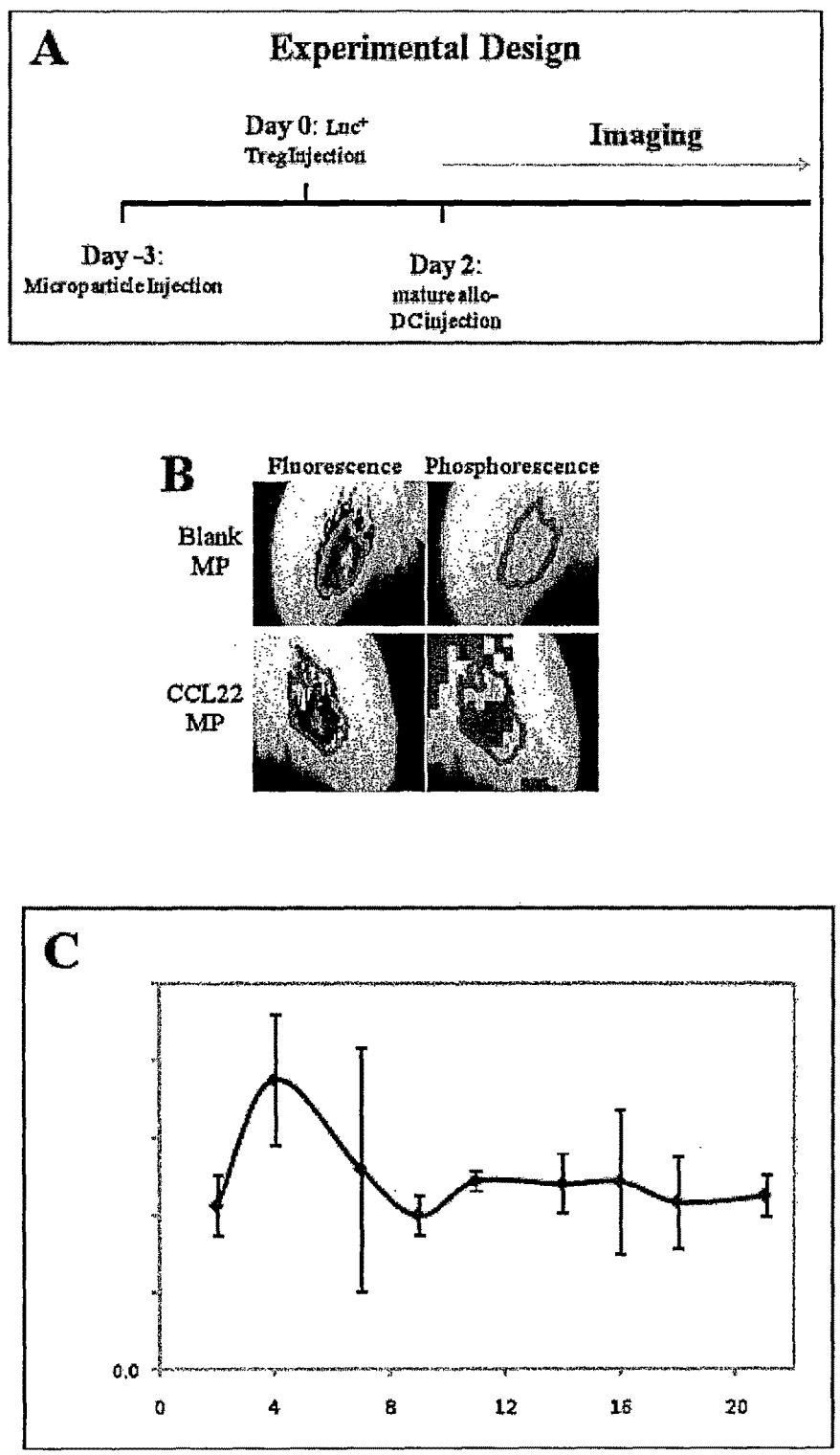
FIG. 19 presents exemplary data showing an in vivo migration of Tregs towards microparticles comprising CCL22.
Figure 20:
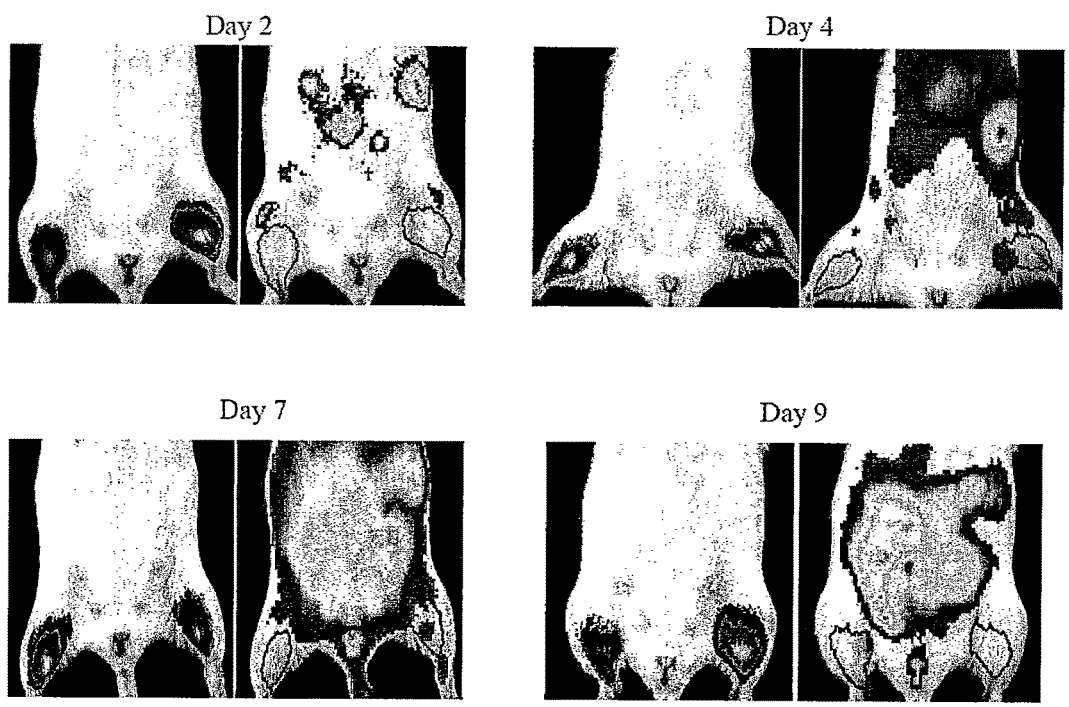
FIG. 20 presents exemplary data of non-invasive live animal imaging. The left limb was injected with BlankMP-680 and the right limb was injected with CCL22MP-680. Representative fluorescence (left) and luminescence (right) images taken from a single mouse at different time points following injection. Days 4 & 7: Significant co-localization of Treg with CCL22 microparticles. Days 2 and 9: Very little or no co-localization of Treg with CCL22 microparticles. Values represent the total flux (photons/sec) of fluorescence or luminescence intensities. ROI (regions of interest) were drawn automatically using Igor Pro Living Image® 2.60.1. Influx of Treg only towards CCL22MP was observed over multiple experimental cycles (n=6). Over time it was observed that Treg localized in mucosal tissues such as the gut and the lung, which secrete CCL22 endogenously. Endogenous Treg migration to the hind limbs was negligible and the cells that migrated to these sites were specifically towards CCL22MP.
Figure 22:
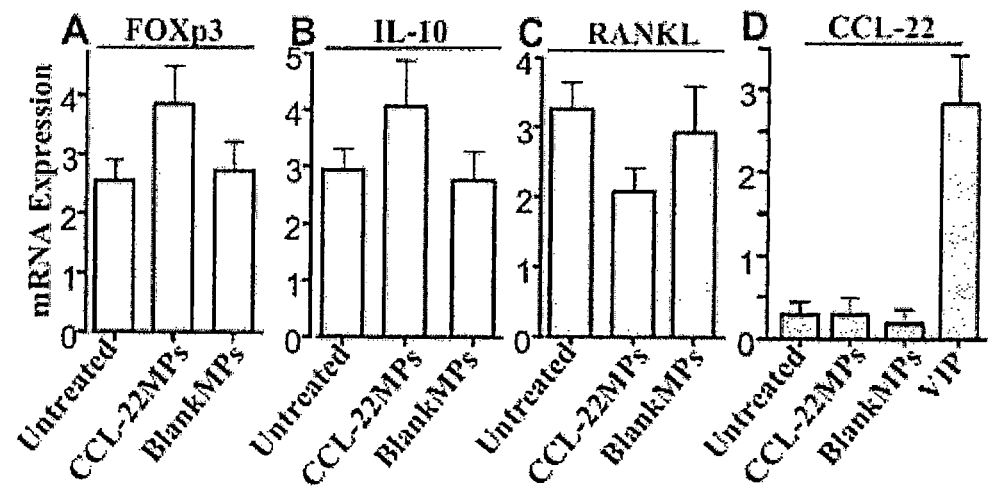
FIG. 22 presents exemplary data showing mRNA expression of markers in periodontal tissues resected from diseased mice (A) FoxP3 a marker for Tregs. (B) Antiinflammatory, pro-regenerative cytokine IL-10. (C) Bone resorbing cell (ostecoclast) activation factor RANKL. (D) Endogenous CCL-22 (Treg recruiting) chemokine.

To verify that Tregs are recruited toward microparticles that sustain release of CCL-22, formulations were administered into the periodontium of diseased mice. Briefly, mice were orally exposed to the periodontal pathogen *A. actinomycetemcomitans* (Aa) on day 0, and also received CCL-22 microparticles (CCL-22 MPs) or blank (empty) microparticles (BlankMPs) in their periodontal pockets. Specifically, mice received microparticle injections at day −1, 10 and 20, mice treated with VIP injections received systemic injections at days −1, 7, 14, 21, 28. Untreated mice served as negative controls. At day 30, all mice were sacrificed and maxilla's were resected. Real-time polymerase chain reaction (QPCR) analysis provided strong evidence that our formulations recruit Tregs to a greater extent than other groups as detected by greater expression of FoxP3. FIG. 22A. This same treatment group also showed statistically greater expression of the pro-regenerative cytokine IL-10. FIG. 17B. Further, a decreased expression of bone resorbing cell activator RANKL was observed. FIG. 22C. Interestingly, systemic VIP injections induced endogenous production of CCL-22 presumably leading to Treg recruitment, and the disease symptom attenuation as demonstrated below.

Figures 23A, 23B, 23C:
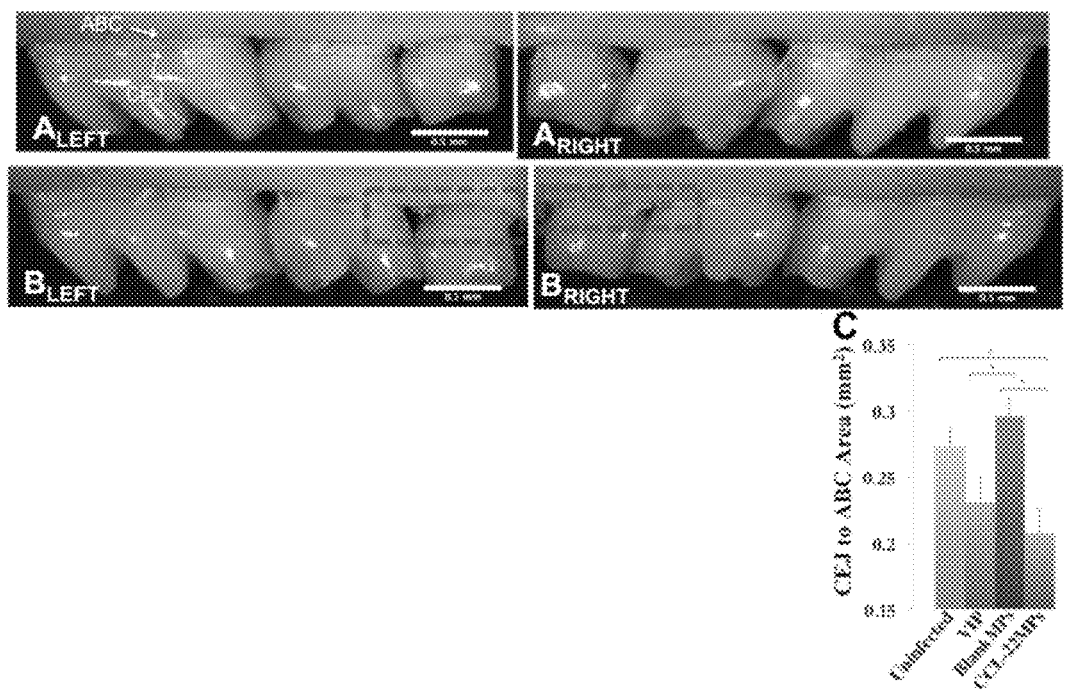
FIG. 23 presents exemplary data showing abrogation of alveolar bone resorption in a mouse model of periodontitis. (A-B) dissecting microscope images of resected maxilla mechanically de-fleshed and soaked in dispase overnight. Dotted-red boxes outline large differences in alveolar bone levels (between the internal control B LEFT, and CCL-22 MP treated B RIGHT). (A) Representative image from mice that received BlankMPs A RIGHT in the right maxilla and no treatment (internal control) A LEFT in the left maxilla. (B) Representative image from a mouse that received CCL-22 MPs B RIGHT in the right maxilla and no treatment (internal control) B LEFT in the left maxilla (C, right) Area measurements (CEJ-ABC) for the right maxilla of mice from each treatment and control group. *p-value<0.05
Figure 24:
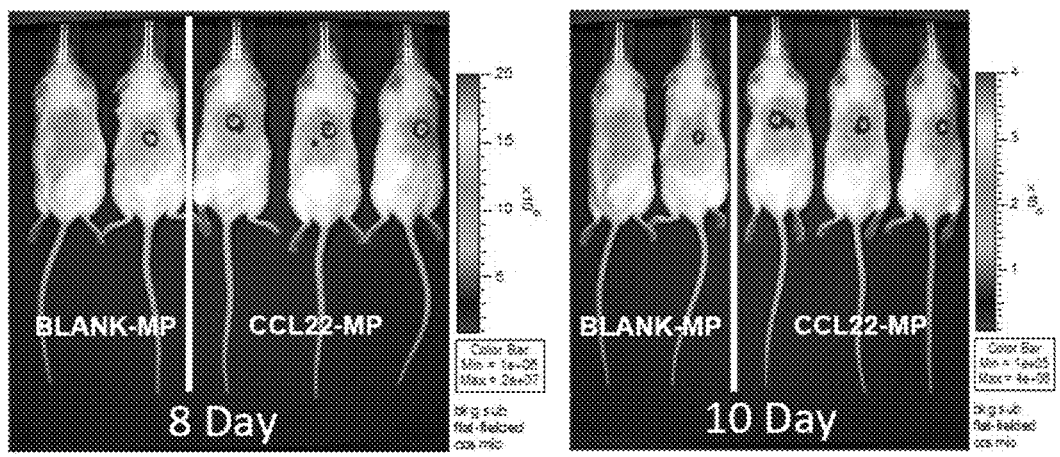
FIG. 24 presents exemplary data showing tumor regression after induction of Treg cells. Transgenic luciferase expressing lewis lung carcinoma cells (derived from C57Bl/6 mice) were injected into FVB mice 4 days post particle injections. Quantitative live animal imaging was performed subsequently at regular time intervals. Above images show qualitative data obtained at 2 different time points, suggesting that the CCL22 microparticles are able to slow down rejection of cellular allo-transplants.
Figure 25:
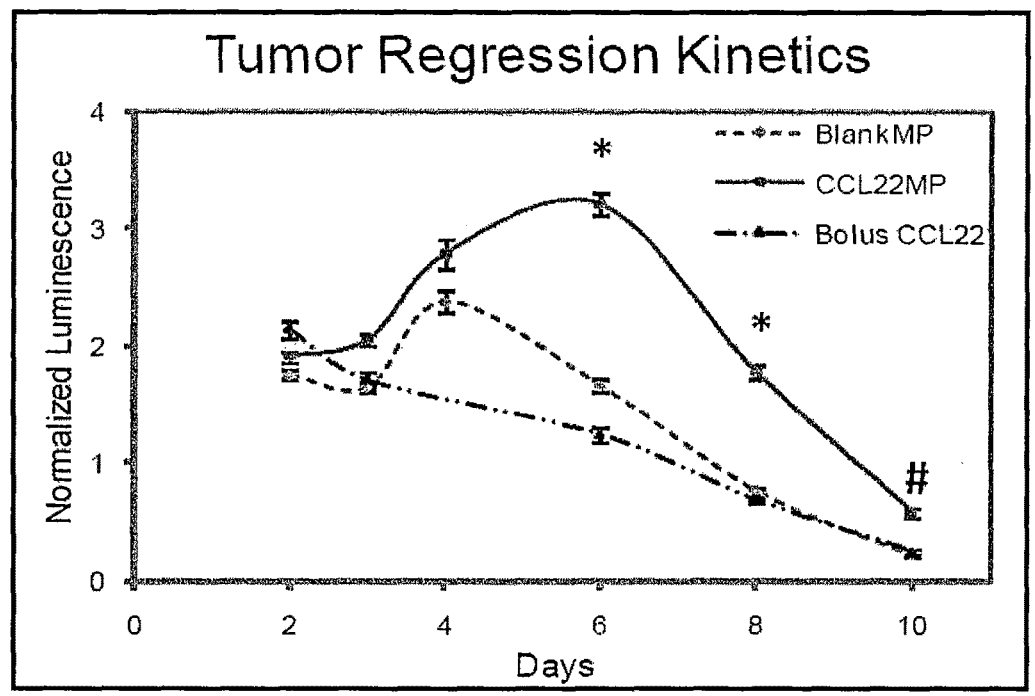
FIG. 25 presents tumor regression kinetic data from the experiment demonstrated in FIG. 24. * Indicates p<0.05; Wilcoxon rank-sum test for null hypothesis that normalized luminescence for CCL22MP is same as that of BlankMP or bolus CCL22. # p≤0.05 (comparison between CCL22MP and BlankMP only). n=11 BlankMP and CCL22MP (n=5 for bolus CCL22)

To confirm that Treg recruiting formulations attenuate periodontal disease symptoms, levels of alveolar bone resorption was examined in experimental mouse periodontitis. G. P. Garlet et al., Clin Exp Immunol 147, 128 (January, 2007); D. T. Graves, D. Fine, Y. T. Teng, T. E. Van Dyke, G. Hajishengallis, J Clin Periodontol 35, 89 (February, 2008); and J. J. Yu et al., Blood 109, 3794 (2007). To this end, B6 mice (n=6) were infected orally with the periodontal pathogen *A. actinomycetemcomitans* (Aa) and treated with microparticles containing CCL-22 (CCL-22 MPs) or empty microparticles (BlankMPs) according to the schedule outlined above. Additionally vasoactive intestinal peptide (VIP) was administered intraperitoneally. Mice receiving only PBS and the thickener carboxymethyl cellulose served as controls (Untreated). Experimental treatments were administered in the periodontal pocket of the right maxilla while left maxillae were used as internal negative controls in each mouse. Alveolar bone loss was quantified as the area between the cementoenamel junction (CEJ) and the alveolar bone crest (ABC) FIG. 23, CEJ and FIG. 23A, ABC). Alveolar bone levels are shown on the left (internal control, FIG. 23A LEFT) and right (BlankMP treated, FIG. 23A RIGHT) maxilla. Both the internal control and BlankMP treated maxilla (FIG. 23A, both) exhibited significant alveolar bone loss. However, FIG. 23 RIGHT depicts a maxilla treated with CCL-22 MPs, revealing significantly reduced alveolar bone loss, both compared to the internal control maxilla (FIG. 28 LEFT) and the BlankMP treated maxilla (FIG. 23A RIGHT). Quantification of total bone loss (area in mm2) reveals that CCL-22 MP as well as VIP (systemic IP injections) treatments led to significantly less alveolar bone resorption than BlankMPs. FIG. 23C.

VI. Clinical Applications

A. Immunosuppressant Therapy Substitution for Tissue/Graft Transplants

The development of new immunosuppressive agents has been the general direction in efforts to improve the transplantation success rate. For example, the use of agents which inhibit the production of lymphocyte proliferation factors have extended the half life of pediatric heart transplants. Pietra et al., *Prog Pediatr Cardiol* 11:115-129 (2000). Presently, research is underway in efforts to further increase pediatric heart half-lives using agents which inhibit the de novo synthesis of nucleotides and block co-stimulation of T-cells.

Presently available immunosuppressant drugs act to abrogate acute rejection of tissue transplants. Tissue transplant rejections are usually characterized by recognition of the foreign donor antigen by the adaptive immune system and the subsequent expansion of lymphocytes which attack the transplanted tissue. Symptoms which accompany acute rejection (including, but not limited to, pain at the transplantation site or fever-like symptoms) are more frequent and severe immediately following transplantation, but commonly recur 6-12 months subsequent to the procedure. Persistent episodes of acute rejection are thought to lead to a state of chronic rejection coupled with a failure of many immunosuppressant drugs. The most viable option following the onset of chronic tissue rejection is re-transplantation, which is undesirable from both the standpoint of allograft availability and the increased difficulty of the repeated operation.

A major disadvantage of immunosuppressant therapy is that in order to avoid both episodes of acute rejection and the initiation of chronic rejection, immunosuppressant drugs must be administered over the entire life of the transplant recipient. A further disadvantage of immunosuppressant therapy is the frequent incidence of side effects. For example, in the case of cyclosporine treatment (a commonly used agent which decreases the production of interleukin 2, or IL2), patients have been known to experience tremors, headaches, blurry vision, high blood pressure, and inhibited kidney function. Other commonly used immunosuppressants also cause frequent side effects, which range from growth retardation to behavioral instability to neurotoxicity. Besides these drug specific side effects, the consequences of long term immunosuppression in general can be profound including, but not limited to, increases in the risk of infection, heart disease, diabetes, and cancer.

While a combined administration of the immunosuppressant mycophenolate mofetil along with Vitamin D3 has been reported to generate dendritic cells with a tolerogenic phenotype resulting in increased numbers of regulatory T-cells in mice, mycophenolate mofetil suffers from the same adverse side effects as the immunosuppressants mentioned above and has also been implicated in causing birth defects in animals. Gregori et al., *J Immunol* 167:1945-1953 (2001). Furthermore, immunosuppressants can cause inhibition of regulatory T-cells as well as the T-cells these therapies intend to impede. Li et al., *Nat Med* 5:1298-1302 (1999). Due to the potential of these tolerogenic cells, it is important that a greater understanding of the factors involved in the expansion and employment of $T_{reg}$ cells in vivo is developed.

The present invention contemplates alternatives to extended immune system down-regulation provided by immunosuppressant therapy. Such alternatives are expected to provide a dramatic improvement over the state-of-the-art in the clinic. For example, the most desirable of these alternatives would render the patient's immune system in a state of complete, permanent tolerance to a specific foreign body (i.e., for example, a single antigen and/or antigen complex). Once this complete and permanent tolerance is attained, no further treatment is necessary to prevent transplant-related adverse reactions. Furthermore, the recipient's immune system would otherwise function normally, being fully capable of fighting pathogens and/or stopping the progression of tumor cells. Although it is not necessary to understand the mechanism of an invention, it is believed that infants up to fourteen (14) months old innately have tissue tolerance due to the lack of soluble and/or surface rejection factors which mediate immediate rejection of the transplant. As the infant's immune system matures, however, this innate tissue tolerance is lost. Fan et al., *Nat Med* 10, 1227-1233 (2004).

B. Implant Tolerance

Numerous polymeric biomaterials and metal materials are implanted each year in human bodies. Among them, drug delivery devices provide local therapeutic effect for diseases which lack efficient treatments. Controlled release systems are in direct and sustained contact with the tissues, and some of them degrade in situ. Thus, both the material itself and its degradation products must be devoid of toxicity. The knowledge and understanding of the criteria and mechanisms determining the biocompatibility of biomaterials are therefore of great importance.

The classical tissue response to a foreign material leads to the encapsulation of the implant, which may impair the drug diffusion in the surrounding tissue and/or cause implant failure. This tissue response depends on different factors, especially on the implantation site. Indeed, several organs possess a particular immunological status, which may reduce the inflammatory and immune reactions. Among them, the central nervous system is of particular interest, since many pathologies still need curative treatments.

In one embodiment, the present invention contemplates a method of inducing implant tolerance by the administration of artificial antigen presenting cells as described herein.

C. Tissue Healing

In one embodiment, the present invention contemplates using artificial microparticles comprising soluble and surface bound factors to induce tissue healing states including, but not limited to bone healing, wound healing, and disease-induced injury tissue restoration.

1. Bone Healing

Over the past several decades, those having ordinary skill in the art have been attempting to understand the interactions between the cells that mediate the process of bone remodeling and healing. It is believed that the cells that mediate bone formation (i.e., for example, osteoblasts) may be capable of stimulating osteoclast cells. Osteoclast cells have been reported to resorb and remodel bone. Mundy G. R., *Bone* 24(5 Suppl):35S-38S (1999). Osteoclasts, derived from a hemopoietic monocyte cell lineage (e.g. in the same cell lineage as dendritic cells and macrophages), resorb bone using proton and enzymatic secretion. Teitelbaum S. L., *Science* 289; 1504-1508. It is generally believed that approximately 10-15% of human bone is perpetually undergoing remodeling in order for our mineralized tissue to grow and adapt to stress. However, the current evidence suggests that when the osteoblast-osteoclast communication pathway breaks down, osteosclerotic symptoms may occur including, but not limited to, fractures, severe infections, blindness, deafness, deformities, or stroke.

Figures 13A, 13B:
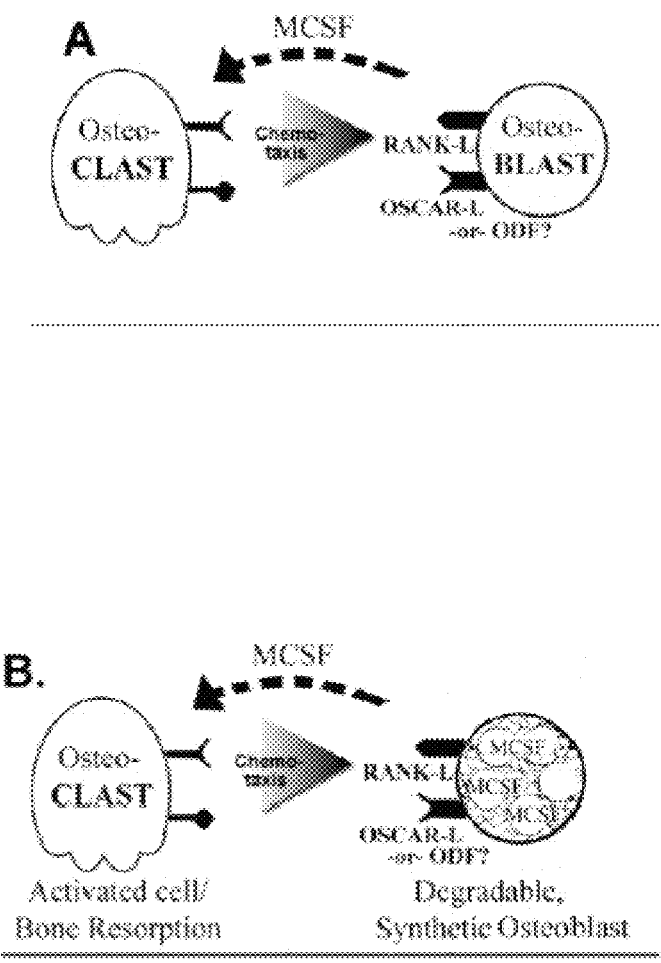
FIG. 13A presents an illustration representing a hypothesized coupling interaction for osteoclast stimulation. For example, osteoclasts may be recruited by MCSF and activated by surface-bound RANK-L and/or OSCAR-L.
FIG. 13B presents an illustration of an artificial osteoblast cell that mimics the coupling interactions shown in FIG. 13A.

Signaling factors (i.e., for example, soluble signaling factors and surface-bound signaling factors) have been consistently implicated as intermediaries between osteoblasts and osteoclasts. Mundy G. R., *Bone* 24(5 Suppl):35S-38S (1999). See, FIG. 13A. In one embodiment, the present invention contemplates a composition comprising an antibody-ligated OSCAR, wherein the antibody/OSCAR composition serves as a co-stimulus with the signaling factors. Merck et al., *Journal of Immunology* 176(5):3149-3156 (2006). Although it is not necessary to understand the mechanism of an invention, it is believed that the antibody/OSCAR composition may be necessary but not sufficient for osteoclast activation alongside other surface-bound signals (i.e., for example, RANK-L) and soluble signaling factor MCSF27.

Conversely, it is commonly known that secretion of osteoprotegrin (OPN) (a molecule that inhibits RANK-L signaling) can diminish osteoclastic activity. Udagawa et al., *Endocrinology* 141:3478-3484 (2000); and Itoh et al., *Endocrinology* 142:3656-3662 (2001). As dendritic cells may undergo suppression via apoptosis/anergy (supra), a similar mechanism downregulating the osteoblast-osteoclast interaction could be application to diseases where the degree of osteoclast resorption exceeds that of osteoblast healing including, but not limited to, osteoporosis or osteopenia.

Finally, has been reported that a balance between bone resorption and healing may be mediated not only by communication of osteoblasts to osteoclasts, but also by communication of osteoclasts to osteoblasts. Martin et al., *Trends in Molecular Medicine* 11: 76-81 (2005). This crosstalk is commonly referred to as "osteo-coupling". Although bone resorption processes are believed to release soluble factors embedded in bone matrix that can recruit and differentiate osteoblastic precursors, some studies suggest that osteoclasts still strongly stimulate osteoblasts in the absence of resorption. Although it is not necessary to understand the mechanism of an invention, it is believed that several soluble signaling factors and several surface-bound signaling factors are likely to be involved.

In one embodiment, the present invention contemplates an artificial biodegradable osteoblast cell that directly and indirectly interacts with an osteoclast cell. In one embodiment, the artificial osteoblast cell mimics osteo-coupling signaling that results in the modulation of bone healing. In one embodiment, the artificial osteoblast cell acts as a biomimetic compound by providing surface bound RANK-L signaling factors, anti-OSCAR antibodies, and a soluble signaling factor (i.e., for example, MIM-1 and/or MCSF-27). Although it is not necessary to understand the mechanism of an invention, it is believed that the artificial osteoblast cell is capable of stimulating osteoclast cells to a greater degree than the "unorganized" forms because of a patterned organization of the signaling factors. In other embodiments, a surface-bound signaling factor comprises osteoclastic differentiation factor (ODF). ODF has been reported to act as a co-stimulator with RANK-L. Suda et al., *Endocrinology Rev.* 13:66-80 (1992). In other embodiments, OPN is used to suppress osteoclasts. Udagawa et al., *Endocrinology* 141:3478-3484 (2000).

Figures 14A, 14B:
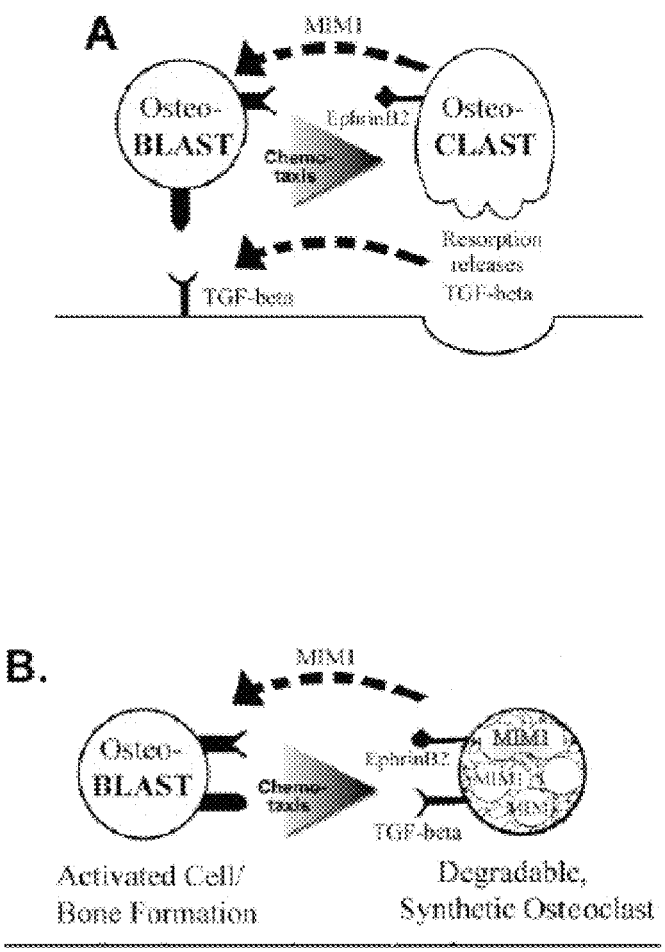
FIG. 14A presents an illustration representing a hypothesized coupling interaction for osteoblast stimulation. For example, osteoblasts may be recruited by MIM1 and activated by surface-bound TGF-beta and EphrinB2 (BMP2).
FIG. 14B presents an illustration of an artificial osteoclast cell that mimics the coupling interactions shown in FIG. 14A.

In some embodiments, osteo coupling may involve a variety of signaling factors. In one embodiment, a soluble signaling factor comprises MIM1, a chemokine specific to osteoblast precursors. Falany et al., *Biochemical and Biophysical Research Communications* 281(1):180-1805 (2001). In one embodiment, a surface-bound signaling factor comprises EphrinB2, that appears to stimulate osteogeneic differentiation. Zhao, et al., *Cell Metabolism* 4:111-121 (2006). In one embodiment, a surface-bound signaling factor comprises TGF-β, believed to stimulate osteoblasts. Pfeilschifter et al., *Proceedings of the National Academy of Sciences* 84:2024-2028 (1987). Although it is not necessary to understand the mechanism of an invention, it is believed that cell-sized biodegradable artificial osteoblast cells displaying surface bound signaling factors (i.e., for example, RANK-L, ODF, EphrinB2 and/or TGF-β) on a polymer surface and controllably releasing a soluble signaling factor (i.e., for example, MIM1 and/or MSCF-27) might act, in combination, as "a synthetic bone surface/synthetic osteoclast" thereby stimulating osteoblasts and/or osteoprecursors to a greater degree than the "unorganized" forms of these factors (i.e., for example, by independent local and/or systemic administration). See, FIGS. 14A and 14B.

Figure 15:
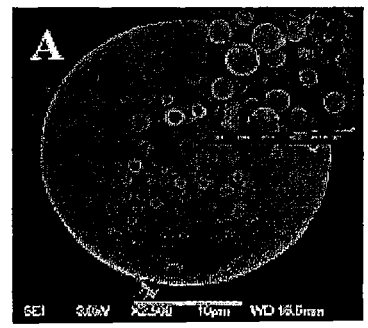
FIG. 15 presents representative scanning micrographs of CCL22-containing microparticles.
Figure 15:
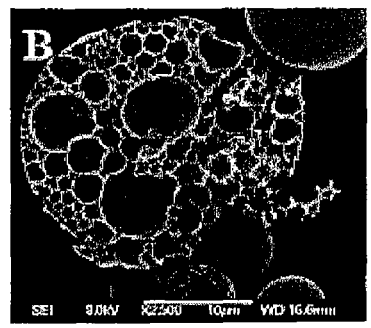

In one embodiment, the present invention contemplates a method of making a functional artificial osteoblast. In one embodiment, the present invention contemplates a method of making a function artificial osteoclast. In one embodiment, the method comprises emulsifying a polymer with a soluble signaling factor to produce a controlled release microparticle. In one embodiment, the controlled release microparticle comprises surface bound signaling factors. In one embodiment, an artificial osteoblast microparticle comprises a soluble MSCF and surface bound factors comprising RANK-L, αOSCAR, and/or EPF. See, FIGS. 14A and 14B. In one embodiment, an artificial osteoclast microparticle comprises a soluble MIM1 and surface bound factors EphB4 and/or TGF-β. See, FIGS. 15A and 15B. Although it is not necessary to understand the mechanism of an invention, it is believed that the encapsulation and release of these agents, and even the ability to precisely pre-program the profile of release maybe measured and/or predicted using mathematical modeling of controlled delivery and variation of the microstructure and chemical structure of the particles.

In one embodiment, the present invention contemplates a method for examining combinations of soluble factors (i.e., for example secreted) and surface-bound factors (i.e., for example, immobilized) in vitro using known differentiation markers and functional assays for osteoblast and osteoclast stimulation. In one embodiment, the method measures the cellular effects via standard co-culture assays. Takahashi et al., *Endocrinology* 123: 2600-2601 (1988); and Suda et al., *Endocrinology* 128:1792-1796 (1991). In one embodiment, the method uses assays for osteoblast activity and osteoprecursor differentiation including staining for alkaline phosphatase, Von-Kossa, and flow cytometric analysis. In one embodiment, the method uses assays for calcium phosphate pit-formation and TRAP staining.

In one embodiment, the present invention contemplates a method for in vivo osteo-coupling using artificial osteoblast and/or osteoclast cells. In one embodiment, the method utilizes a subcutaneous, mouse craniofacial model. In one embodiment, the model determines the effects of combinations of multiple soluble and surface-bound factors by intradermal and/or subcutaneous injections of artificial osteoblast and/or osteoclast cells can be made right under the skin, wherein the cells result in contacting a bone surface. Although it is not necessary to understand the mechanism of an invention, it is believed that these artificial cells can be made large enough as to not move from the site of injection. In one embodiment, the effect of these various artificial cell formulations in vivo are determined using software capable of quantifying bone density and lacunae (resorption) formation in histological sections of the craniofacial bone tissue (BioQuant, Osteoimage).

2. Tissue Healing

Periodontal disease, or periodontitis, is characterized by destructive inflammation of the periodontium (i.e., for example, gum tissue, supporting bone, and/or ligaments) and is considered the most pressing oral health concern today. Importantly, this disease affects not only tooth loss, but also the incidence of cardiovascular disease, kidney disease, respiratory diseases, diabetes, and even premature childbirth. Seymour, G. J., Ford, P. J., Cullinan, M. P., Leishman, S. & Yamazaki, K. Relationship between periodontal infections and systemic disease. Clin Microbiol Infect 13 Suppl 4, 3-10 (2007); Fisher, M. A. et al. Periodontal disease and other nontraditional risk factors for CKD. Am J Kidney Dis 51, 45-52 (2008); Boggess, K. A., Beck, J. D., Murtha, A. P., Moss, K. & Offenbacher, S. Maternal periodontal disease in early pregnancy and risk for a small-for-gestational-age infant. Am J Obstet Gynecol 194, 1316-1322 (2006); Backes, J. M., Howard, P. A. & Moriarty, P. M. Role of C-reactive protein in cardiovascular disease. Ann Pharmacother 38, 110-118 (2004); and Offenbacher, S. & Beck, J. D. A perspective on the potential cardioprotective benefits of periodontal therapy. Am Heart J 149, 950-954 (2005). Periodontal disease is strikingly prevalent in the United States, affecting 34% of individuals over the age of 30, or an estimated 78 million Americans. Garlet, G. P. et al. Regulatory T cells attenuate experimental periodontitis progression in mice. Journal of Clinical Periodontology 37, 591-600. It is the number-one cause of tooth loss according to the American Dental Association. Beyond the US, periodontal disease is estimated to affect up to 20% of the adult population worldwide. Furthermore, the periodontal biofilm hosts a wide variety of potentially hazardous bacterial species that can lead to systemic infections and inflammatory immune diseases. The most predominant periodontal pathogens, *Actinobacillus actinomycetemcomitans, Porphyromonas gingivalis, Tannerella forsythia* and *Fusobacterium nucleatum*, present virulence factors that have been associated with: 1) systemic infections and complications; 2) a 4-fold increase in premature births, 3) anorexia-cachexia syndrome, 4) atherosclerosis, and 5) mycordial infarction and ischemic stroke. As the correlations between periodontitis and the incidence of these other conditions continue to be elucidated, reducing the prevalence of periodontal disease is a significant current medical problem and must be solved. The continuing prevalence of periodontal disease is likely perpetuated by a misunderstanding of the disease etiology consonant with current therapies that are aimed at removal of these remarkably common bacterial species. The current standard of care involves the debridement of calculus and plaque, often accompanied by local delivery of an antibiotic such as minocycline (Arestin®). These conventional treatments temporarily kill pathogens, but do not protect against inevitable future infections nor address the sensitivity that is observed in patients that are disposed to immune dysfunction. Although invasive bacterial species are protagonists of the disease, tissue destruction is mediated by an adverse host inflammatory immune response. Baker, P. J. The role of immune responses in bone loss during periodontal disease. Microbes and Infection 2, 1181-1192 (2000); Graves, D. T., Fine, D., Teng, Y. T., Van Dyke, T. E. & Hajishengallis, G. The use of rodent models to investigate host-bacteria interactions related to periodontal diseases. J Clin Periodontol 35, 89-105 (2008).

In some embodiments, the present invention contemplates a method for treating inflammation caused by periodontal disease. Although it is not necessary to understand the mechanism of an invention, it is believed that as the disease progresses, several populations of lymphocytes are recruited to the periodontium, guided by local gradients of specific lymphocyte-attracting chemokines. It is further believed that the overall cytokine milieu produced by these specific populations of lymphocytes that ultimately directs the expression of factors that promote hard and soft tissue destruction.

For example, in some embodiments an artificial antigen presenting cell provides a therapy for inflammation resulting from periodontal gum disease. Periodontal disease is strikingly prevalent in the United States (34% of individuals over age 30 or an estimated 78 million Americans). Eke et al., "CDC Periodontal Disease Surveillance Project: background, objectives, and progress report" *J Periodontol* 78:1366-1371 (2007). Periodontal disease is a cause of tooth loss according to the American Dental Association and is a current oral health concern. It is believed that periodontal disease not only affects tooth loss but also contributes to the incidence of cardiovascular disease, diabetes, and respiratory disease such as pneumonial. Furthermore, women who have periodontal disease are over 4 times more likely to give birth to a child prematurely. Boggess et al., "Maternal periodontal disease in early pregnancy and risk for a small-for-gestational-age infant" *Am J Obstet Gynecol* 194:1316-1322 (2006). Clearly, finding a solution to the problem of periodontal disease is needed in the art. In: Pennsylvania Department of Health report: "Status of Oral health in Pennsylvania" (2002).

Figure 11:
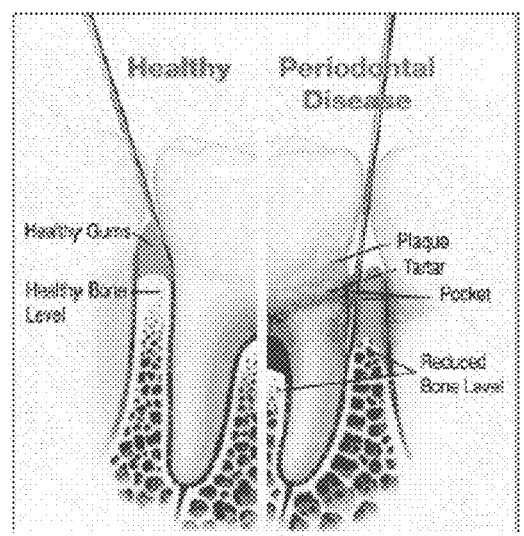
FIG. 11 presents an illustration of one embodiment comparing healthily gum tissue (left side) with gum tissue affected by periodontal disease (right side).

The physiological events associated with periodontal disease are well characterized but the pathologic mechanisms of this disease are unknown. It is believed that periodontal disease affects the composition and integrity of periodontal structures at the dento-gingival junction, alveolar bone, cementum and periodontal ligament. Further it is believed that periodontal disease causes the destruction of connective tissue matrix and cells, loss of fibrous attachment, and resorption of alveolar bone. FIG. 11. Although it is not necessary to understand the mechanism of an invention, it is believed that tissue destruction in periodontal patients is thought to be a result of a complex inflammatory and immune response initiated and perpetuated by gram-negative anaerobic rods and spirochetes. Previous work has suggested that B cells and T cells accumulate in large numbers in the periodontal tissues although much about their functions in the disease process is not clearly understood.

Current therapies for periodontal disease focus upon reducing or controlling bacterial infection in the gums. Traditional, mechanical debridement techniques temporarily remove the accumulated bacterial plaque responsible for inflammation. One treatment strategy provides a controlled release of the antibiotic minicycline from PLGA microspheres that are placed in the periodontal pocket (Arestin®, OraPharma). Although both of these techniques may temporarily reduce inflammation associated with bacteria, they do not intend to treat the susceptibility of the area to inflammation and the reformation of pockets that cultivate further infection leading to re-establishment of disease. Since periodontal tissue destruction is initiated and exacerbated by inflammatory host response, there has been an increased focus toward understanding the cellular immune responses in the periodontal space in order to treat the source of the physiological response.

Recently, several groups have discovered evidence that the cause of periodontal disease may related to the regulation of inflammation in the local tissues. Cardoso et al., "Characterization of CD4+CD25+ natural regulatory T cells in the inflammatory infiltrate of human chronic periodontitis" *J Leukoc Biol* (2008); and Ernst et al., "Diminished forkhead box P3/CD25 double-positive T regulatory cells are associated with the increased nuclear factor-kappaB ligand (RANK-L+) T cells in bone resorption lesion of periodontal disease" *Clin Exp Immunol* 148:271-280 (2007). It was reported that cytokines which may inhibit and/or regulate inflammation (i.e., for example, IL10) are substantially diminished in tissues with periodontal disease. Although it is not necessary to understand the mechanism of an invention, it is believed that the absence of these anti-inflammatory cytokines not only result in increased inflammation, but also produces a cascade leading to the production of RANK-L. Although it is not necessary to understand the mechanism of an invention, it is believed that RANK-L comprises a factor that differentiates monocyte precursors (i.e., for example, osteoblasts) into bone-resorbing cells called osteoclasts.

The regulation of anti-inflammatory cytokines and more generally, the regulation of the resultant harmful autoimmune responses, may be mediated by immunosuppressive T-cells (i.e., for example, $T_{reg}$ cells). Tang et al., "The Foxp3+ regulatory T cell: a jack of all trades, master of regulation" *Nat Immunol* 9:239-244 (2008). For example, it has been reported that while markers for $T_{reg}$ cells were present in healthy tissues, they were absent in diseased periodontal tissues. Further, it has been reported that patients with rheumatoid arthritis (predisposition for autoimmune regulation breakdown) have 8-fold increased odds of developing periodontal disease. Pischon et al., "Association among rheumatoid arthritis, oral hygiene, and periodontitis" *J Periodontol* 79:979-986 (2008).

As discussed above, periodontal disease is currently treated with strategies focused only on the removal of invasive bacterial species. Specifically, the clinical procedure called scaling and root planing involves the mechanical removal of plaque and bacteria from beneath the gingiva (i.e., for example, debridement), and is typically preformed by a periodontal specialist. In severe cases, antibiotic treatments in the form of controlled release microparticles may be injected into the periodontal pocket (i.e., for example, Arrestin®, PLGA microparticles encapsulating and controllably releasing the antibiotic minocycline for 21 days). Williams, R. C. et al. Treatment of periodontitis by local administration of minocycline microspheres: A controlled trial. Journal of Periodontology 72, 1535-1544 (2001). This treatment approach is insufficient because, antibiotic treatments only temporarily removes the bacterial species and recurrent infections are common, requiring patients to repetitively undergo these expensive procedures. While such antibiotic treatments temporarily remove the bacterial insult, they do not address the sensitivity seen in patients that are susceptible to such immune-mediated tissue destruction. Furthermore, antibiotic treatment and/or scaling is completely ineffective in approximately 20% of the population and may induce antibiotic resistance, thereby limiting patient options for future treatment.

Recent periodontal disease research has investigated the inflammatory immune reaction itself. For example, one recent experimental treatment aimed at reducing the host inflammatory response involves the administration of the drug Resolvin®. Resolvin® blocks neutrophil-mediated inflammation and the associated pro-inflammatory cytokine milieu. Hasturk, H. et al. Resolvin E1 regulates inflammation at the cellular and tissue level and restores tissue homeostasis in vivo. J Immunol 179, 7021-7029 (2007). However, it has been shown that direct, long-term, inhibition of inflammatory cytokines by traditional blocking strategies (i.e., for example, anti-inflammatory compounds) can compromise periodontal tissue healing. Gurgel, B. C. et al. Selective COX-2 inhibitor reduces bone healing in bone defects. Brazilian oral research 19, 312-316 (2005); Ribeiro, F. V. et al. Selective cyclooxygenase-2 inhibitor may impair bone healing around titanium implants in rats. Journal of Periodontology 77, 1731-1735 (2006); Simon, A. M., Manigrasso, M. B. & O'Connor, J. P. Cyclo-oxygenase 2 function is essential for bone fracture healing. Journal of Bone and Mineral Research 17, 963-976 (2002); Vuolteenaho, K., Moilanen, T. & Moilanen, E. Non-steroidal anti-inflammatory drugs, cyclooxygenase-2 and the bone healing process. Basic and Clinical Pharmacology and Toxicology 102, 10-14 (2008); Zhang, X., Kohli, M., Zhou, Q., Graves, D. T. & Amar, S. Short- and long-term effects of IL-1 and TNF antagonists on periodontal wound healing. Journal of Immunology 173, 3514-3523 (2004). Further, it has also been shown that traditional blocking of the protective immune responses actually results in increased bacterial burden and acute systemic reactions. Garlet, G. P. et al. The essential role of IFN-gamma in the control of lethal *Aggregatibacter actinomycetemcomitans* infection in mice. Microbes Infect 10, 489-496 (2008); and Garlet, G. P. et al. The dual role of p55 tumour necrosis factor-α receptor in *Actinobacillus* actinomycetemcomitans-induced experimental periodontitis: Host protection and tissue destruction. Clinical and Experimental Immunology 147, 128-138 (2007). Consequently, an untested strategy toward disease resolution may not require complete blocking of the protective immune responses and would clearly be a more desirable approach.

Notably, harmful inflammatory responses are not regulated by blocking leukocyte infiltration, but rather by balancing inflammatory leukocyte recruitment with regulatory lymphocyte recruitment. Vignali, D. A. A., Collison, L. W. & Workman, C. J. How regulatory T cells work. Nature Reviews Immunology 8, 523-532 (2008); and Campanelli, A. P. et al. CD4+CD25+ T cells in skin lesions of patients with cutaneous leishmaniasis exhibit phenotypic and functional characteristics of natural regulatory T cells. J Infect Dis 193, 1313-1322 (2006). Regulatory T-cells (Treg) may exert their control over other lymphocytes both by several mechanisms including but not limited to secreting factors and through direct cell-cell interactions, ultimately leading to targeted inflammatory-immune cell arrest. However, progress has been made toward utilizing Treg therapeutically for a wide variety of autoimmune and inflammatory diseases. Adoptive (Treg) cell transfer (i.e. cell infusion therapies) have seen the most pre-clinical success. Yet clinical translation of the complicated ex vivo cellular expansion protocols has proven difficult. Riley, J. L., June, C. H. & Blazar, B. R. Human T Regulatory Cell Therapy: Take a Billion or So and Call Me in the Morning. Immunity 30, 656-665 (2009). One may spectulate that periodontal disease treatment would have the best clinical impact with an off-the-shelf therapeutic that improves the body's natural mechanisms for immune regulation (recruitment/activation of endogenous Treg) in attempt to restore local immune homeostasis and balance.

Naturally, immune cells are recruited to peripheral sites via chemokines secreted by tissue resident cells. Specifically, biological gradients of chemokines direct immune cells toward the origin of secretion (i.e., for example, at an infection site). For example, one way in which tumors appear to avoid immune surveillance and clearance is through the recruitment of regulatory T cells. Specifically, tumors produce and sustain a biological gradient of CCL22 (a Treg-associated chemokine) that directs Treg migration. Dutzan, N., Gamonal, J., Silva, A., Sanz, M. & Vernal, R. Over-expression of forkhead box P3 and its association with receptor activator of nuclear factor-κ B ligand, interleukin (IL)-17, IL-10 and transforming growth factor-β during the progression of chronic periodontitis. Journal of Clinical Periodontology 36, 396-403 (2009); Sather, B. D. et al. Altering the distribution of Foxp3+ regulatory T cells results in tissue-specific inflammatory disease. Journal of Experimental Medicine 204, 1335-1347 (2007); Garlet, G. P., Avila-Campos, M. J., Milanezi, C. M., Ferreira, B. R. & Silva, J. S. *Actinobacillus actinomycetemcomitans*-induced periodontal disease in mice: patterns of cytokine, chemokine, and chemokine receptor expression and leukocyte migration. Microbes Infect 7, 738-747 (2005). Once co-localized, Treg suppress effector immune cells by secreting factors such as IL-10 and TGF-β, thereby establishing immunological homeostasis in an milieu that would otherwise present itself as highly inflammatory. Rabinovich, G. A., Gabrilovich, D. & Sotomayor, E. M. in Annual Review of Immunology, Vol. 25 267-296 (2007).

Although it is not necessary to understand the mechanism of an invention, it is believed that engineering principles may result in the production of controlled release systems that can produce a stable biological gradient of certain chemokines (i.e., for example, CCL22). These microparticles can be fabricated using an FDA-approved polyester and will degrade in a well characterized manner in vivo. Rothstein, S. N., Federspiel, W. J., Little, S. R. A unified mathematical model for the prediction of controlled release from surface and bulk eroding polymer matrices. Biomaterials (2009); Garlet, G. P. et al. The dual role of p55 tumour necrosis factor-alpha receptor in *Actinobacillus* actinomycetemcomitans-induced experimental periodontitis: host protection and tissue destruction. Clin Exp Immunol 147, 128-138 (2007). Theoretically, by mimicking the natural immune-evasion mechanisms of tumors using rationally-designed, CCL22-releasing, polymeric microparticles, Tregs may be recruited to a site of destructive inflammation (i.e., for example, a diseased periodontium).

In one embodiment, the present invention contemplates a method comprising a controlled delivery of Treg chemoattractants (i.e., for example, CCL22 and/or vasoactive intestinal peptide, VIP) in the periodontium that can abrogate periodontal disease symptoms. In one embodiment, the method is clinically viable, biocompatible, and non-inflammatory. Rothstein, S. N., Federspiel, W. J., and Little, S. R. A simple model framework for the prediction of controlled release from bulk eroding polymer matrices. Journal of Materials Chemistry 18, 1873-1880 (2008); Rothstein, S. N., Federspiel, W. J., Little, S. R. A unified mathematical model for the prediction of controlled release from surface and bulk eroding polymer matrices. Biomaterials (2009); Delgado, M., Gonzalez-Rey, E. & Ganea, D. VIP/PACAP preferentially attract Th2 effectors through differential regulation of chemokine production by dendritic cells. FASEB Journal 18, 1453-1455 (2004); Little, S. R. et al. Poly-beta amino ester-containing microparticles enhance the activity of non-viral genetic vaccines. Proc Natl Acad Sci USA 101, 9534-9539 (2004). In one embodiment, the method comprises a controlled release formulation that is tunable and provides a long-lasting delivery of a drug. Although it is not necessary to understand the mechanism of an invention, it is believed that these embodiments provide a potential solution for immune imbalance and dysfunction associated with periodontal disease, while avoiding immune-blocking strategies. It is further believed that these embodiments are supported by preliminary data showing: 1) Tregs are attracted toward a preliminary formulation of CCL22 microparticles, in vitro and in vivo; 2) administration of CCL22 microparticles results in resolution of periodontal disease symptoms in in vivo animal models; 3) transformation/proliferation of CD4+ lymphocyte populations into FoxP3+ regulatory lymphocytes is possible using factors including, but not limited to, TGF-β, IL2, and/or rapamyacin.

Inflammatory imbalances may cause periodontal tissue destruction wherein the inflammatory cascade is primarily initiated by bacterial recognition through innate immune cells bearing toll like receptors (TLRs). Garlet, G. P., Avila-Campos, M. J., Milanezi, C. M., Ferreira, B. R. & Silva, J. S. *Actinobacillus actinomycetemcomitans*-induced periodontal disease in mice: Patterns of cytokine, chemokine, and chemokine receptor expression and leukocyte migration. Microbes and Infection 7, 738-747 (2005); McGinity, J. W. & O'Donnell, P. B. Preparation of microspheres by the solvent evaporation technique. Adv Drug Deliv Rev 28, 25-42 (1997); Burns, E., Bachrach, G., Shapira, L. & Nussbaum, G. Cutting edge: TLR2 is required for the innate response to *Porphyromonas gingivalis*: Activation leads to bacterial persistence and TLR2 deficiency attenuates induced alveolar bone resorption. Journal of Immunology 177, 8296-8300 (2006); Kajita, K. et al. Quantitative messenger RNA expression of Toll-like receptors and interferon-alpha1 in gingivitis and periodontitis. Oral Microbiol Immunol 22, 398-402 (2007); Nakamura, H. et al. Lack of Toll-like receptor 4 decreases lipopolysaccharide-induced bone resorption in C3H/HeJ mice in vivo. Oral Microbiology and Immunology 23, 190-195 (2008). Triggering of these pathogen receptors may lead to the induction of pro-inflammatory mediators including, but not limited to, TNF-α, IL-1β and IFN-Y. Garlet, G. P., Martins Jr, W., Ferreira, B. R., Milanezi, C. M. & Silva, J. S. Patterns of chemokines and chemokine receptors expression in different forms of human periodontal disease. Journal of Periodontal research 38, 210-217 (2003); Garlet, G. P. et al. Cytokine pattern determines the progression of experimental periodontal disease induced by *Actinobacillus* actinomycetemcomitans through the modulation of MMPs, RANKL, and their physiological inhibitors. Oral Microbiology and Immunology 21, 12-20 (2006). This skewed, pro-inflammatory environment may upregulate soft tissue destroying matrix metalloproteinases (MMPs) and/or RANKL a receptor activator of nuclear factor κB ligand and a potent activator of bone resorbing osteoclasts. Garlet, G. P. et al. The essential role of IFN-gamma in the control of lethal *Aggregatibacter actinomycetemcomitans* infection in mice. Microbes Infect 10, 489-496 (2008); Garlet, G. P. et al. The dual role of p55 tumour necrosis factor-α receptor in *Actinobacillus* actinomycetemcomitans-induced experimental periodontitis: Host protection and tissue destruction. Clinical and Experimental Immunology 147, 128-138 (2007); Tang, Q. & Bluestone, J. A. The Foxp3+ regulatory T cell: A jack of all trades, master of regulation. Nature Immunology 9, 239-244 (2008); Normenmacher, C. et al. DNA from periodontopathogenic bacteria is immunostimulatory for mouse and human immune cells. Infection and Immunity 71, 850-856 (2003); Graves, D. T. & Cochran, D. The contribution of interleukin-1 and tumor necrosis factor to periodontal tissue destruction. J Periodontol 74, 391-401 (2003). Inflammatory mediators may result in tissue destruction in the periodontium and inhibit the production of anti-inflammatory factors conducive for disease amelioration and healing. Consequently, the present invention contemplates a method for solving the periodontal disease problem by controlling the inflammatory response associated with the known immunological imbalance associated with periodontitis.

Tregs have been shown to reestablish immune homeostasis through a wide variety of mechanisms, both at the site of inflammation (i.e., for example, the periodontium) and/or at the draining lymph nodes (i.e., for example, the cervical lymph nodes). Taubman, M. A., Valverde, P., Han, X. & Kawai, T. Immune response: the key to bone resorption in periodontal disease. J Periodontol 76, 2033-2041 (2005) Specifically, Tregs act to balance these pro-inflammatory mediators by secreting anti-inflammatory factors including, but not limited to, IL-10 and/or TGF-β. Vignali, D. A. A., Collison, L. W. & Workman, C. J. How regulatory T cells work. Nature Reviews Immunology 8, 523-532 (2008); Cardoso, C. R. et al. Characterization of CD4+CD25+ natural regulatory T cells in the inflammatory infiltrate of human chronic periodontitis. Journal of Leukocyte Biology 84, 311-318 (2008). Indeed, recent reports have shown that IL-10 levels are substantially diminished in patients with severe periodontitis. Zhang, N. et al. Regulatory T Cells Sequentially Migrate from Inflamed Tissues to Draining Lymph Nodes to Suppress the Alloimmune Response. Immunity 30, 458-469 (2009). IL-10 has been shown to play a major role in attenuation of periodontal disease by upregulating an extracellular RANKL inhibitor osteoprotegerin (OPG) and promoting increased levels of intra-inflammatory-cell 'suppressors of cytokine signaling' (SOCS). Claudino, M. et al. The broad effects of the functional IL-10 promoter-592 polymorphism: Modulation of IL-10, TIMP-3, and OPG expression and their association with periodontal disease outcome. Journal of Leukocyte Biology 84, 1565-1573 (2008); Garlet, G. P., Cardoso, C. R., Campanelli, A. P., Martins Jr, W. & Silva, J. S. Expression of suppressors of cytokine signaling in diseased periodontal tissues: A stop signal for disease progression? Journal of Periodontal Research 41, 580-584 (2006). Furthermore, IL-10 not only regulates the inflammatory immune response, but also plays a key role in bone anabolism, leading to maturation of bone forming osteoblasts. Abe, T. et al. Osteoblast differentiation is impaired in SOCS-1-deficient mice. J Bone Miner Metab 24, 283-290 (2006); Lorentzon, M., Greenhalgh, C. J., Mohan, S., Alexander, W. S. & Ohlsson, C. Reduced bone mineral density in SOCS-2-deficient mice. Pediatr Res 57, 223-226 (2005); Ouyang, X. et al. SOCS-2 interferes with myotube formation and potentiates osteoblast differentiation through upregulation of JunB in C2C12 cells. J Cell Physiol 207, 428-436 (2006). Finally, TGF-β has been shown to play an important role in immune regulation and tissue healing, specifically through the recruitment and guidance of periodontal ligament cells. Ernst, C. W. O. et al. Diminished forkhead box P3/CD25 double-positive T regulatory cells are associated with the increased nuclear factor-κB ligand (RANKL+) T cells in bone resorption lesion of periodontal disease. Clinical and Experimental Immunology 148, 271-280 (2007).

In one embodiment, the present invention contemplates a method for restoring the immunosupressive regulatory balance in periodontal space, thereby reversing periodontal disease progression. In one embodiment, the population of Treg cells in the periodontal space is increased. In one embodiment, the amount of immunosupressive cytokines (i.e., for example, CCL-22) in the periodontal space is increased. Although it is not necessary to understand the mechanism of an invention, it is believed that immunosupressive cytokines activate $T_{reg}$ cells that actually mediate the immunosuppression.

Figure 9A:
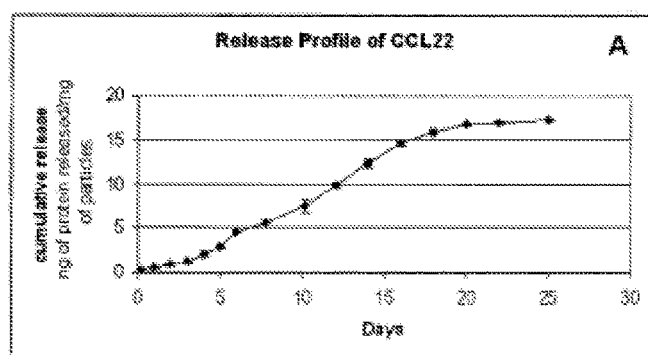
FIG. 9A presents exemplary data showing a release profile of CCL22 from porous particles showing approximately linear release for over twenty (20) days.
Figure 9B:
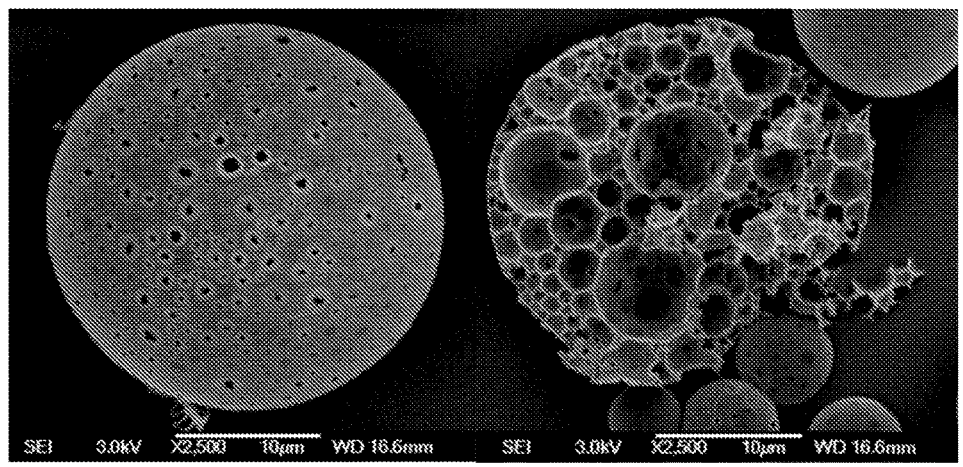
FIG. 9B presents exemplary data showing the successful creation of microparticles encapsulating CCL22 as used in FIG. 9A. The top portion shows a representative image of an intact microparticle, indicating the particle's structural integrity and confirming the size. The bottom portion shows a representative image of a fractured particle confirming the porous nature of the particle created by the double emulsion encapsulation process.
Figure 10:
FIG. 10 presents exemplary data showing CCL22 labeling (red) using the microparticles in accordance with FIG. 9.

Treg populations have been identified in periodontal lesions. In one embodiment, the present invention contemplates a method providing a controlled release of soluble $T_{reg}$ stimulatory factors (i.e., for example, CCL-22) from soluble biodegradable microparticles after injection into a periodontal space. The data presented herein demonstrates a sustained release of CCL-22 over a period of 1 month from microparticles composed of the FDA-approved polymer, PLGA. FIG. 9A. Although it is not necessary to understand the mechanism of an invention, it is believed that the released cytokine recruits $T_{reg}$ cells back into the periodontal space, thereby restoring immune regulation and abrogating periodontal disease progression. See, Example XII.

In one embodiment, the present invention contemplates a method for the controlled delivery of Treg chemoattractants in the periodontium thereby promoting localization of endogenous Treg and abrogating periodontal disease symptoms. In one embodiment, the method further comprises recruiting endogenous Treg to the periodontium. In one embodiment, the periodontal disease symptoms are abrogated by reducing inflammation. Although it is not necessary to understand the mechanism of an invention, it is believed that the this method is supported by preliminary data demonstrating that: 1) controlled release of CCL22 leads to the recruitment of endogenous, Foxp3+ regulatory T-cells to the periodontium; 2) administration of CCL22 controlled release formulations leads to both higher numbers of Treg in draining lymph nodes and resolution of periodontal disease symptoms in in vivo animal models; and 3) beyond recruitment of Treg, a combination of specific factors have been identified that could induce the proliferation and/or transformation of local CD4+ lymphocytes toward enriched Treg populations.

In one embodiment, the present invention contemplates formulations capable of a long-lasting release of Treg-inducing factors. In one embodiment, the formulation is used for the treatment of periodontitis. In one embodiment, microparticles comprising CCL22 and/or vasoactive intestinal peptide (VIP), are constructed of biodegradable poly (lactic-co-glycolic acid) (PLGA) polymer. Rothstein, S. N., Federspiel, W. J., and Little, S. R. A simple model framework for the prediction of controlled release from bulk eroding polymer matrices. Journal of Materials Chemistry 18, 1873-1880 (2008). In one embodiment, the PLGA microparticles facilitate Treg recruitment to the periodontium. In one embodiment, the microparticle is a controlled release microparticle.

In one embodiment, the present invention contemplates a method comprising a microparticle formulation for treating periodontal disease, wherein the formulation promotes Treg recruitment, thereby reducing alveolar bone loss. Although it is not necessary to understand the mechanism of an invention, it is believed that local lymphocytes may expand toward an enriched population of Tregs through controlled release of a combination of several key molecules. Although it is not necessary to understand the mechanism of an invention, it is believed that recruited Tregs may play a role in periodontal disease abrogation and host response. For example, CCL22 microparticle formulation and systemic VIP effectively induce Treg migration to periodontal tissues and may abrogate disease symptoms. In one embodiment, the present invention contemplates formulations that induce Treg chemotaxis and therapeutic function in the periodontium by monitoring Treg residence and disease symptoms. For example, normal mice may be compared to mice deficient in receptors thought to play a role in chemotactic migration and immunological function. Further, gene expression levels of Treg markers, inflammatory mediators, soft and hard tissue destroying factors and biomolecules involved in bone growth to elucidate the mechanisms of Treg-mediated periodontal disease abrogation may also be assessed.

VII. Antibodies

The present invention provides for the use of antibodies (i.e., for example, polyclonal or monoclonal). In one embodiment, the present invention provides monoclonal antibodies that specifically bind to a polypeptide residing on a $T_{reg}$ cell.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% CO2 gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a protein expressed resulting from a virus infection (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

VIII. Kits

In another embodiment, the present invention contemplates kits for the practice of the methods of this invention. The kits preferably include one or more containers containing an artificial antigen presenting cell of this invention. The kit can optionally include a soluble $T_{reg}$ stimulation protein. The kit can optionally include a surface $T_{reg}$ stimulation protein. The kit can optionally include nucleic acids such as FoxP3. The kit can optionally include chemicals capable of functionalizing the polymer ends of an artificial antigen presenting cell. The kit can optionally include a pharmaceutically acceptable excipient and/or a delivery vehicle (e.g., a liposome). The reagents may be provided suspended in the excipient and/or delivery vehicle or may be provided as a separate component which can be later combined with the excipient and/or delivery vehicle. The kit may optionally contain additional therapeutics to be co-administered with an artificial antigen presenting cell.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in the induction and maintenance of tissue tolerance. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

IX. Pharmaceutical Compositions

The present invention further provides pharmaceutical compositions (e.g., comprising the artificial antigen presenting cells described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on type and amount of tissue that is transplanted. The course of treatment lasting from several days to several months, or in some cases, for the lifetime of the recipient. Optimal dosing schedules can be calculated from measurements of compound accumulation in the body of the patient. The administering physician can easily determine optimum dosages, dosing methodologies and repetition rates. Optimum dosages may vary depending on the relative potency of individual oligonucleotides, and can generally be estimated based on $EC_{50s}$ found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues.

EXPERIMENTAL

Example I

Emulsification of Regulatory T-Cell Modulating Agents

Figure 5A:
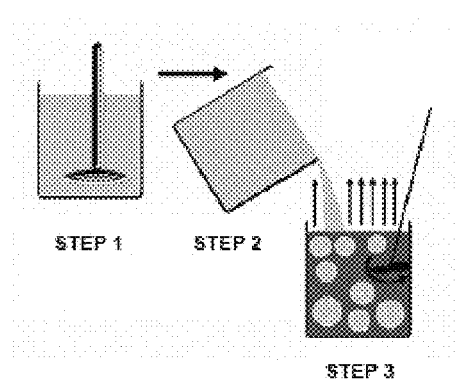
FIG. 5A presents an illustration of one embodiment for the fabrication of polymer microparticles via a double-emulsion/solvent evaporation technique. Step 1: Sonication of a drug in an aqueous solution and polymer in organic solution to form a primary emulsion; Step 2: The primary emulsion is poured into stirring detergent solution to form a secondary emulsion; and Step 3: The secondary emulsion is stirred and solvent evaporates to form solid particles.
Figure 5B:
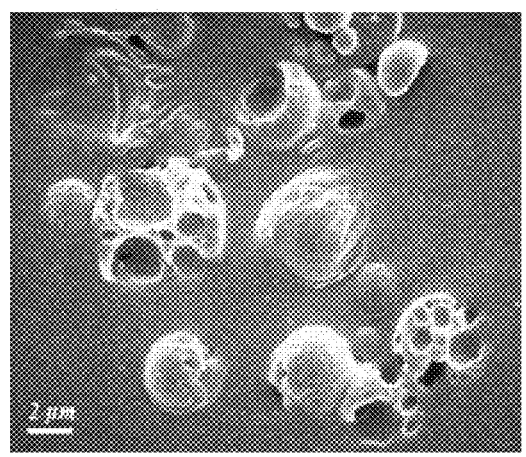
FIG. 5B presents exemplary data of the technique shown in FIG. 5A using a freeze fracture scanning electron micrograph of microparticles demonstrating the interior, aqueous protein factor containing compartments.

Preparing emulsions of water soluble factors using biodegradable polymers is a commonly used strategy to deliver materials over extended periods of time and can make administration of factors with short half lives in vivo a reality. The use of the double-emulsion/solvent-evaporation technique is a commonly used strategy. Odonnell et al., *Advanced Drug Delivery Reviews* 28: 25-42 (1997), See, FIG. 5. A frequently used polymer in these formulations is poly-lactic-co-glycolic acid (PLGA), which is both biocompatible and FDA approved. PLGA is also attractive because its degradation rates can be controlled by the ratio of its monomers (lactide which is more hydrophobic, and glycolide which is more hydrophilic). This control over degradation behavior provides the ability to release factors over periods from days to months. Hanes et al., *Pharm Biotechnol* 6:389-412 (1995). Microparticles prepared in this manner can carry large payloads and encapsulate multiple agents including, but not limited to: i) cytokines (Thomas et al., *J Pharm Sci* 93: 1100-1109 (2004)); ii) small peptides (Haining et al., *J Immunol* 173:2578-2585 (2004)); iii) small molecule drugs; and iv) nucleic acids (Little et al., *Proc Natl Acad Sci USA* 101: 9534-9539 (2004)). The size can be controlled by parameters such as the concentration of the polymer solution, agitation speeds during fabrication, and amount of surfactant used in the outer aqueous phase during the emulsification procedure. These formulations can be administered in a variety of ways, including injection through a needle and syringe.

Any number of compounds may be emulsified using the above methodology. However, of most interest to the embodiments discussed herein, factors which are thought to influence the anti-inflammatory environment during tolerance induction are completely compatible with the system described here (i.e., for example, IL2, TGF-β, and CCL22). Further, the emulsification and release of IL2 in PLGA microparticles using a double and single emulsion systems has recently been reported. Thomas et al., *J Pharm Sci* 93: 1100-1109 (2004). Specifically, IL2 was encapsulated and released in an active state for periods of up to 4 months. Similarly, TGF-β has been encapsulated in microparticles using PLGA polymer blends with release demonstrated for a period of over 1 month. Kempen et al., *J Biomed Mater*

Res A 70:293-302 (2004); and Lu et al., *J Biomed Mater Res* 50:440-51 (2000). CCL20, but not CCL22, has been encapsulated in PLGA microparticles which have been shown stimulate significant amounts of in vitro dendritic cell chemotaxis (i.e., for example, over 0.5 mm from their original position to the point of contact with the particle). Zhao et al., *Biomaterials* 26:5048-5063 (2005). Importantly, this chemotaxis was greater than that following bolus administration of the chemokine. CCL22 has been reported to induce regulatory T-cell chemotactic migration both in vitro and in vivo. Curiel et al., Nat Med 10:942-949 (2004).

Example II

Labeling Artificial Presenting Cell Surface Polymer Functionalization

This example provides a simple, rapid detection method to detect particle surface polymer modifications capable of attaching to soluble and membrane $T_{reg}$ stimulation factors.

Figure 6:
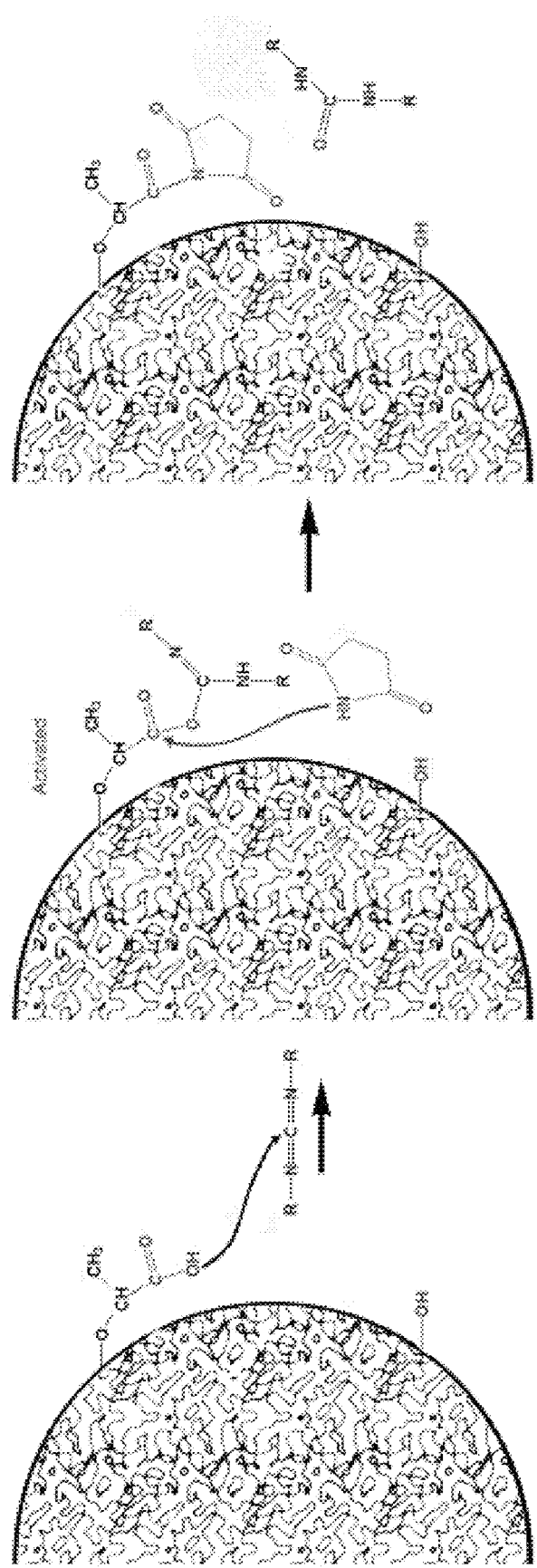
FIG. 6 illustrates standard carbodiimide chemistry to create an amine reactive site on the surface of PLGA microparticles starting with a carboxylic acid generated from the degradation of ester bonds.

Particle surface labeling of biodegradable polymers has been accomplished using several established techniques. The most common strategy for PLGA is to utilize carboxylic acid groups, which are present at the end groups and are generated upon degradation of the ester bonds in its backbone. This can be accomplished using carbodiimide chemistry and can be facilitated using NHS esters. See, FIG. 6.

Another approach has been to create more of these carboxylic acid groups on the surface using a surfactant which is rich in these chemical groups during fabrication of the particle. Keegan et al., *Macromolecules* 37:9779-9784 (2004). Also, short treatments with 0.1M NaOH can generate an abundance of these groups on the particle surface.

Figure 7:
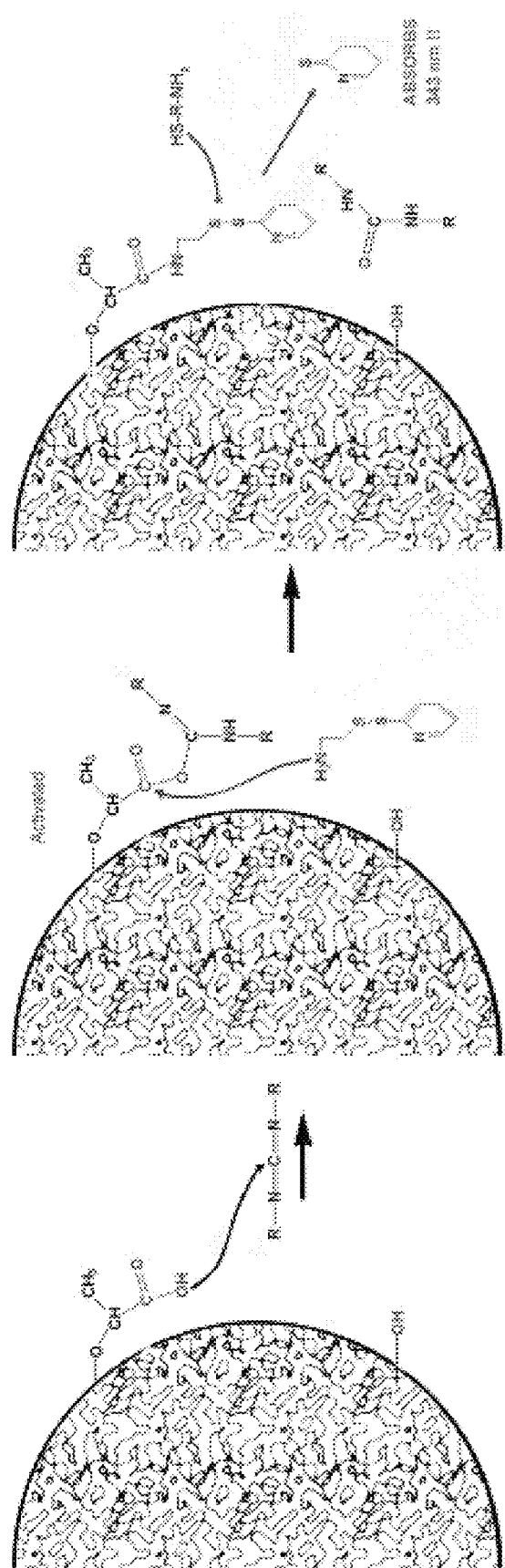
FIG. 7 presents one embodiment to label functionalized PLGA polymers using a novel compound (i.e., for example, 2-pyridyldithioethylamine) to convert a carboxylic acid group into a thiol reactive group (See, middle panel). A subsequent cleavage reaction liberates a detectable product upon conjugation which can be used to determine the extent of surface labeling (see, right panel).

A new technique is presented in this example that quantifies surface labeling using a modification of the carbodiimide chemistry approach. In this technique, 2-pyridyldithioethylamine, reacts with activated esters and also contains a disulfide bond which is, in turn, readily reacted with thiol compounds. See, FIG. 7 middle panel. This reaction liberates a new chemical entity which absorbs light at 342 nm. See, FIG. 7 right panel.

Light absorption can be readily detected using any standard absorbance plate reader. The absorbance data, along with the total amount of particles and their average surface area, can determine an estimate of the number of labeling events per unit area on the particle surface. This technique has successfully labeled the surface of 10 micrometer PLGA microparticles wherein dithiothreitol was used to liberate the absorbent product (data not shown).

Alternatively, streptavidin may be used to facilitate the binding of commercially available biotin-labeled antibodies. For example, EDC/carbodiimide and NHS chemistry can take place in MES buffer in which microparticles are suspended. The reaction tube will need to be constantly rotated to keep particles evenly suspended for approximately 2 hours. Particles will then be washed and 2-pyridyldithioethylamine (PDA) will be added to the activated ester by 4 hour incubation under agitation.

After washing, these particles are labeled with thiolated streptavidin in excess. Particles will be spun down and supernatants removed for analysis at 343 nm.

Values obtained will be compared to a standard curve to determine the number of moles reacted/weight of particles. The average total available surface area for reaction can be determined by preparing an aqueous suspension of particles with a known concentration. This suspension will be analyzed by Coulter Counter to determine the number of particles per unit weight. The value, along with the average diameter of the particles and the number of moles of streptavidin reacted/weight particles leads to the number of streptavidin linkages per unit area on the microparticle surface. This value can be checked with the use of commercially available biotin conjugated to a fluorescent linker. Particles could be labeled with this material, washed, dissolved using NaOH/SDS, and this solution's fluorescence could be measured. This intensity, as compared to a standard curve, would indicate the amount of labeling/weight of particles. A pH insensitive fluorescent probe would need to be used in these experiments. These fluorescently labeled particles will also be incubated (n=3) in a similar fashion as described above for the controlled release assay. Stability of the surface linkage will be determined by the amount of fluorescence in the supernatant after centrifugation (label that has been liberated from the particle surface)

Example III

Emulsification of Soluble $T_{reg}$ Cell Factors in PLGA Microparticles

This example describes the emulsification (i.e., for example, encapsulation) of soluble factors within PLGA microparticles using a modified double emulsion procedure. Odonnell et al., *Advanced Drug Delivery Reviews* 28:25-42 (1997).

Briefly, 20 μg of protein factor and 20 mg of bovine serum albumen will be dissolved in 200 μL of sterile PBS and added to a solution of 100 mg of 10, 18-30, or 40-78 kDa PLGA with a lactide:glycolide monomer ratio of 50:50 in 2 ml of dichloromethane. This two phase system will be sonicated for 10 seconds using a probe sonicator to form the primary emulsion. The emulsion will immediately be transferred to 50 mL of a homogenizing (5000 rpm), aqueous solution containing 5% by weight poly(vinyl) alcohol (PVA) which serves as a surfactant. After 30 seconds of homogenization, the double emulsion is transferred to a stirring solution of 1% PVA (100 mL) to allow for evaporation of the dichloromethane over a period of 3 hours. The particles will then be centrifuged at <150 rcf in a refrigerated centrifuge and the supernatant containing PVA will be decanted. Particles will be resuspended, washed with cold water, and the process repeated 3×. Washed particles will then be suspended in a minimal amount of water and lyophilized for 3 days to allow sufficient time for removal of residual chloroform. Smaller particles can be prepared using homogenization at 7000 rpm (1 μm). Larger particles can be prepared using a lower concentration of surfactant in the outer aqueous phase of the emulsions (i.e. PVA=1% and 0.5% by weight) which will result in 10-20 μm particles.

Particle size will be determined by a Coulter Counter using volume impedance. Particle loading will be checked by exposing 5 mg of particles to a 0.5 M NaOH, 2% SDS solution to promote total degradation of the particles and dissolution of the protein. Concentrations can be determined using a BCA assay kit via the manufacturer's instructions and loading can be determined (n=3). It should be reasonable to assume that the relative amount of $T_{reg}$ cell factor will remain the same with respect to BSA during encapsulation. However, this assumption can be checked using factor-specific ELISA in place of the BCA assay initially. A typical encapsulation efficiency using the double-emulsion/solvent-evaporation method for proteins is approximately 50%.

Example IV

Controlled Release of Soluble Factors from PLGA Microparticles

This example provides a method to determine the controlled release of soluble factors from microparticles made in accordance with Example III.

Approximately 10 mg of microparticles (n=3) will be weighed out into microcentrifuge tubes and suspended in 500 μL of PBS. Tubes will be sealed and placed on a shaker plate at 37° C. At 12 hour time intervals, tubes will be centrifuged, supernatants removed and stored at −70° C., and new buffer will be added to the particles. At the end of 2 weeks, supernatants will be analyzed for $T_{reg}$ cell stimulating factor using a specific ELISA and release will be plotted over time with standard deviations. Values obtained for all particle formulations in these studies can be used for setting up the appropriate conditions for measuring the activity of these factors and determining their effects on $T_{reg}$ cells in vitro.

Example V

Primary Regulatory T-Cell Isolation

Lymph nodes will be harvested from BALB/c mice and processed to achieve a single cell suspension. Magnetic cell sorting (MACS) will be employed to purify the population via a depletion step which enriches the CD4+ population of cells (mostly CD4+CD25−) and a positive selection step involving CD25 (resulting in mostly CD4+CD25+). Cells will be cultured thereafter in RPMI 1640 media including 10% FCS, glutamine, HEPES, nonessential amino acids, penicillin/streptomycin, and 2-mercaptoethanol.

Example VI

Biological Activity of Encapsulated TGF-β and IL2

For the determination of TGF-β and IL2 activity, the effect of released factors are measured on a population of CD4+ cells prior to positive selection of CD25. This assay is takes advantage of the fact that TGF-β and IL2 can aid in the differentiation of peripheral CD4+ cells to increase their expression of FoxP3 and suppress alloreactive lymphocytes. Fu et al., *Am J Transplant* 4:1614-27 (2004). Both TGF-β and IL2 are present at the same time as TCR engagement thereby facilitating activation.

CD4+CD25− cells are treated for 5 days with experimental groups, mAb specific to CD3 (1 μg/ml), and syngenic, lymphocyte-depleted and irradiated splenocytes. To examine biological activity of encapsulates, the following experimental groups (n=3) are used: 1) fresh, TGF-β and IL2 (1 ng/ml) as a positive control, 2) particles with no encapsulated factors and no external addition of IL2 or TGF-β, 3) IL2 particle incubation with the cells+(1 ng/ml fresh TGF-β), 4) TGF-β particle incubation with the cells+(1 ng/ml fresh IL2).

After treatment, cells will be analyzed by flow cytometry for the increased presence of CD25 and intracellular expression of FoxP3 (via Cytofix/Cytoperm kit and labeled FoxP3 mAb) which would indicate activation of the cells. The amount of particles to be used in these experiments will be based on the results of the controlled release assay (described above) to allow for equivalent amounts of administered growth factor. Groups 3 and 4 will be compared to Group 1 to determine the biological activity of the released IL2 and TGF-β, respectively.

Example VII

Measurement of $T_{reg}$ Cell In Vitro Chemotaxis

Figure 8:
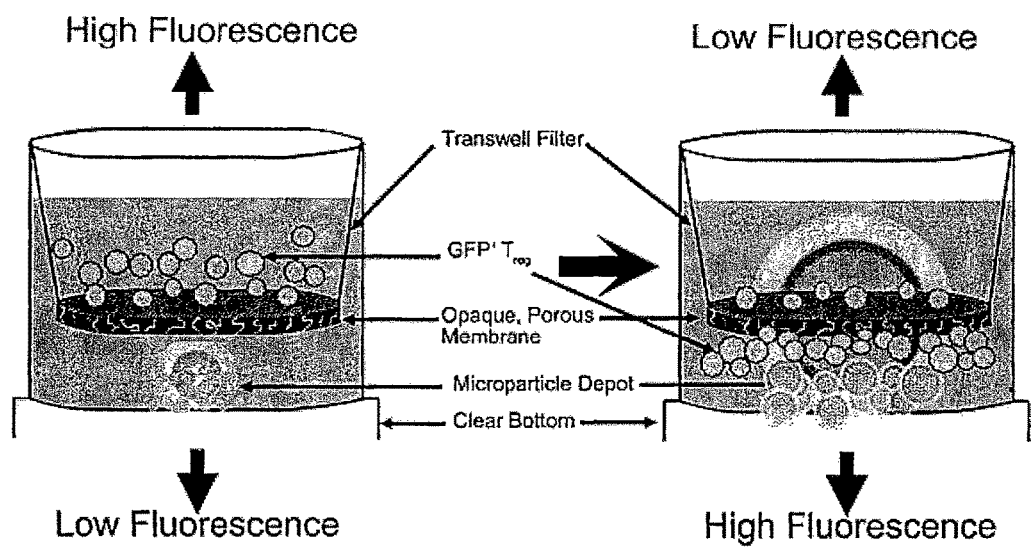
FIG. 8 illustrates one embodiment of an in vitro chemotaxis assay. Microparticles containing chemokines are placed in the bottom of a transwell filter plate with $T_{reg}$ cells isolated from a transgenic B6/GFP+ mouse on top of the opaque filter (left). After time, chemokine is released and $T_{reg}$ cells migrate through the filter and up the concentration gradient of chemokine (right). Fluorescence readings are taken with a top and bottom detector plate reader to determine the extent of chemotaxis.

This example provides one method for measuring the in vitro chemotaxis of $T_{reg}$ cells in response to chemokine release (i.e., for example, CCL22) from particles. See, FIG. 8.

Regulatory T-cells will be isolated as described above using green fluorescent protein transgenic mice (GFP+− C57BL/6 mice). This provides fluorescently labeled cells which have not been treated by any external reagents. Microparticles containing CCL22 (n=3) will be placed below opaque, transwell filters (mean pore size=3 μm and 5 μm). Cells will be seeded on top of this membrane and allowed to incubate for 5 hours before measuring fluorescence. A top and bottom fluorescent reading format is used which allows for the determination of the number of fluorescent cells that have migrated through the membrane at any point. No checkerboard analysis is needed to differentiate between chemotaxis and chemokinesis given that the only factor we are using in our experiments is a well known chemotactic agent.

Alternatively, a carboxyfluorescein diacetate succinimidyl ester, or CSFE (a factor used to track T-cell proliferation), may be used instead of the GFP transgenic mice to label the $T_{reg}$ cells. A manual counting of cells both below and above the transwell filter (using unlabeled cells as a control) should be performed to determine if CSFE has any effect on the chemotaxis of the regulatory T-cells.

Experimental controls include, but are not limited to: 1) wells with blank microparticles (as a negative control); and 2) wells containing soluble CCL22 at 0.5-20 ng/ml (the typical manufacturer's stated ED50 range for this material) as a positive control. The amount of microparticles used in this experiment are derived from the controlled release experiment (described above) to equalize the released CCL22 with the positive controls.

A t-test using two-tailed, unequal variance will be used to determine differences between groups with $p<0.05$ being deemed significant.

Example VIII

In Vitro Measurement of Soluble Released Factors

This example identifies one embodiment for measuring the effect of surface co-stimulatory and soluble released factors on $T^{reg}$ cells in vitro.

Materials

Latex beads with streptavidin can be easily purchased in 1, 5, and 10 μm sizes and can be labeled in one step with biotinylated mAb specific to CD3 and CD28. Optionally, the surface bound moieties can be optimized.

In addition to determining the optimal size for the surface labeled microparticles, label ratios are also varied to optimize the proliferation of primary $T_{reg}$ cells (i.e., for example, 0% CD3/100% CD28; 25% CD3/75% CD28, 50% CD3/50% CD28; 75% CD3/25% CD28:100% CD3/0% CD28).

Furthermore, saturating concentration of the stimulatory factors on the particle surface may or may not be optimal for $T_{reg}$ cell proliferation. For example, stimulation of regulatory T-cells by CD28 requires an optimized dose. Fu et al.,

*Am J Transplant* 4:1614-27 (2004); Salomon et al., *Immunity* 12:431-40 (2000). To determine this dose, the total percentage of streptavidin sites accessible to mAb bound biotin are reduced (i.e., for example, by limiting the addition of free biotin during the labeling procedure). All samples (n=3) will be compared using a two-tailed t-test (unequal variance) with p<0.05 being deemed significant.

Methods

Primary $T_{reg}$ cells will be isolated from C57BL/6 mice and expanded using helper cell-free in vitro conditions including the addition of fresh IL2. The latex bead system will serve as a positive control for comparison with labeled PLGA microparticles of different sizes. Negative controls will include untreated cells and cells treated with particles without surface label.

Soluble IL2 will be replenished, and the cells recounted bi-weekly, while new particles will be administered twice over a two week period. Besides measurement of total regulatory T-cell proliferation, samples will be taken from the culture flasks bi-weekly for flow cytometry analysis. Cells will be stained with fluorescently labeled mAbs which recognize CD25, and CD4. Intracellular staining for FoxP3 is used to determine the activation state of the regulatory T-cells.

Labeling both IL2 and IL2+ TGF-β encapsulated particles are performed under the same conditions which produced the optimal surface labeled formulation. Also, this protocol will allow the determination if an artificial antigen presenting cell is capable of activating and inducing the proliferation of regulatory T-cells without the need for manual addition of soluble factors.

Example IX

In Vivo Injection of Chemokine Encapsulated Particles

This example demonstrates the injection of chemokine encapsulated particles to determine recruitment capacity in vivo.

Particles will be prepared with the full amount of CCL22 (as described in the first experimental section), ⅓ this amount, and 1/10 of this amount. Primary cells ($1\times10^5$) from transgenic GFP+-B6 mice will be adoptively transferred into normal B6 mice for in vivo chemotaxis experiments. At this time mice will be given an injection of the three types of CCL22 encapsulated microparticles in a solution of sterile PBS and 1% carboxymethylcellulose (to avoid particle settling and needle clogging with the high concentrations of particles used). This injection will either be on a shaved and sterilized belly of the animal (i.e., for example, intraperitoneally) (n=3) or in the tibealis anterior muscle (hind leg) (n=3). On the other side of the animal, blank microparticles will be injected S.C. or I.M. as a control. Another experimental group provides an S.C. or I.M. injection to mice using a soluble CCL22 in the same amount as the CCL22 encapsulated particles (full amount encapsulated) (n=3).

At t=1 day and 3 days, mice will be euthanized and skin or muscle at the site of an injection will be resected for histology sections. In these sections, the more GFP expressing cells near the site of the depot, the greater the success of the formulation. For a more quantitative analysis, we will form a single cell suspension with the resected tissue and analyze using flow cytometery (at 488 nm) to determine how many adoptively transferred regulatory T-cells were recruited compared to the blank microparticle-treated, negative control (deemed statistically significant by t-test, p<0.05).

Example X

In Vivo Injection of Artificial Antigen Presenting Cells

This example demonstrates the injection of artificial antigen presenting cells to determine manipulative effect on $T_{reg}$ cells in vivo.

Artificial antigen presenting cells will be prepared by encapsulating an optimized CCL22 formulation plus IL2 and TGF-β followed by an optimized surface labeling strategy. Experimental groups will be designed to explore the necessity of the included factors for stimulation of the recruited regulatory T-cells in vivo (i.e. for example, one formulation with each soluble and surface stimulating component being absent). Mice will be adoptively transferred with transgenic, GFP+ regulatory T-cells as described above and administered injections in the same manner, but this time with the artificial APC formulations instead of encapsulated CCL22 alone (n=3 for each group). Cells from resected skin and muscle will be intracellularly stained for the level of FoxP3 expression (given the strong correlation between its up-regulation and $T_{reg}$ cell stimulatory capacity).

These experiments are repeated with the intent of sorting CD4+ cells instead of intracellular FoxP3 staining. The sorted cells will subsequently be used as suppressor cells (suppressor: responder ratios of 1:1, 2:1 and 5:1) with freshly isolated CD4+CD25− which have been pre-labeled with CSFE (15 μM) and stimulated for 3 days using monoclonal antibodies specific for CD3 (1 μg/ml) and syngenic, irradiated splenocytes (depleted of lymphocytes). Cultures will be monitored using flow cytometry. Efficient suppression would result in a decreased dilution (or higher signal at 488 nm) of CSFE in the cellular population due to the fewer cell divisions of a suppressed lymphocyte. To determine the necessity of each of the individual factors, experimental groups will be compared via two tailed t-test assuming unequal variance with p<0.05 being considered significant.

Example XI

Induction of Allograft Tolerance Using Artificial Antigen Presenting Cells

This example demonstrates therapeutic use of optimized artificial antigen presenting cells for induction of allograft tolerance.

The results of the in vivo suppressor assay (supra) provides optimized formulations and are used for the in vivo allograft tolerance assays. These optimized formulations will be co-administered using either a depot administration of, or by coating the transplant in, artificial antigen presenting cells (n=5). Controls will include mice with no treatment and mice administered (15 mg/kg day) cyclosporine S.C. as a positive control (n=5). Furthermore, an optional experimental group comprising an artificial APC group with an initial cyclosporine dose of 15 mg/kg day, and then reduced to examine the effect of immunosuppressant promotion or inhibition of immune tolerance induction (n=5). The experimental endpoint will be 100 days post operation.

For skin transplantation, mice will be shaven, sterilized, and anesthetized before preparation of two graft beds on the posterior chest wall. Rosenberg A. S. (1991), eds. Coligan, J. E., Kruisbeek, A. M., Margulies, D. H., Shevach, E. M. & Strober, W. (John Wiley and Sons, New York), pp. 4.4.1-4.4.12. These graft beds will engraft full thickness skin grafts from the tail of a donor and syngenic control. After one week of recovery, the transplant will be monitored daily for redness, hair growth, hemorrhaging, and status of graft borders. The percentage of viable skin will be recorded daily until only 10% remains, at which time the animal will be euthanized.

Heterotopic heart transplants will be performed as previously described. Zhang et al., *Transplantation* 62:1267-1272 (1996). Rejection will be monitored via direct abdominal palpitation using the following ranking system: A). Strongly beating, B) Noticeable decline from A, or C) Termination of pulsation at which time the animal will be euthanized.

Following termination of the animals in both transplant models, the allografts will be fixed in 10% formaldehyde and sent for embedding, staining, and evaluation of rejection. Percentage of surviving grafts in each group will be plotted against time for comparison.

A log rank test will be used to compare groups with transplantation rejection data as analyzed by any one of many available software packages.

Example XII

Restoring Immunological Regulation in Periodontal Diseased Tissues

Results Overview

Figure 12:
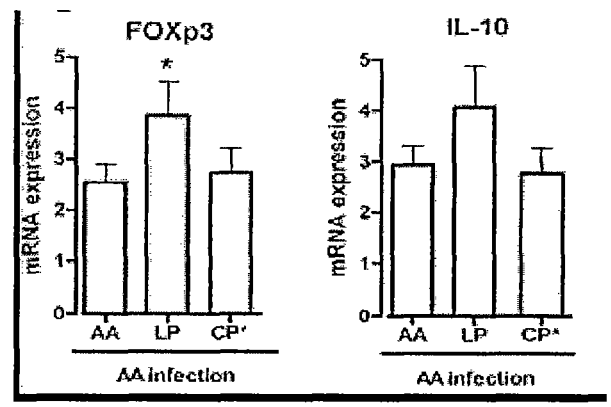
FIGS. 12A and 12B present exemplary data showing the effect of artificial antigen presenting cells encapsulating CCL-22 on periodontal disease in a mouse model. AA: infected, untreated mice. LP: infected, aAPC-CCL22 treated mice; CP: infected, aAPC-only mice.
Figure 12:
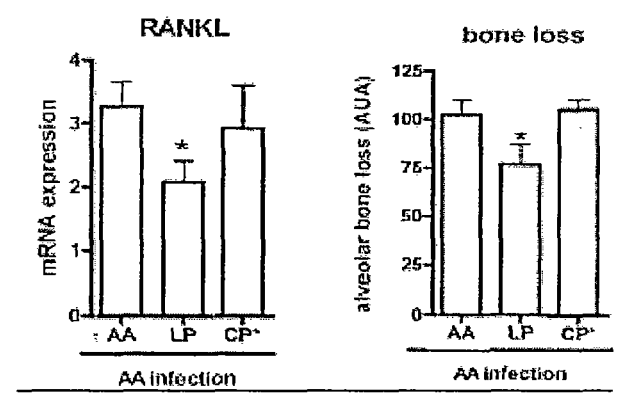

In this experiment, artifical antigen presenting cells providing a CCL-22 controlled release formulation were injected into palatal gingival tissue of right molars of mice (n=3) at the times of −1, 10 and 20 days of periodontal infection. At 30 days, total RNA was extracted from periodontal tissues as previously described and analyzed for regulatory T-cell and periodontal disease factor. Garlet et al., "The essential role of IFN-gamma in the control of lethal *Aggregatibacter actinomycetemcomitans* infection in mice. In: *Microbes and infection/Institut Pasteur* (2008). Infected, untreated mice (AA) and non-loaded particle treated (CP) groups had low levels of FoxP3 (a regulatory T-cell marker) and IL10 (a suppressive cytokine secreted by $T_{reg}$ cells), but elevated levels of RANK-L (an osteoclast differentiation factor). See, FIGS. 12A & 12B. Conversely, CCL-22 particle treatment groups (LP) had significantly higher levels of FoxP3 and IL10, and significantly lower levels of RANK-L. To determine if the particles had therapeutic effect, mice were given the aforementioned treatments and alveolar bone loss was measured at 30 days as described. Garlet et al., "*Actinobacillus l actinomycetemcomitans*-induced periodontal disease in mice: patterns of cytokine, chemokine, and chemokine receptor expression and leukocyte migration". *Microbes and infection/Institut Pasteur* 7, 738-747 (2005). Mice treated with CCL-22 loaded particles (LP) exhibited significantly reduced bone loss compared to neg. controls. See, FIG. 12B.

Methods

Fabrication and Characterization of Controlled Release Formulations: Encapsulation of recombinant murine CCL-22 into PLGA microparticles was performed using a double emulsion procedure to generate particles in the 10 µm range (supra). Loading was verified by dissolution (NaOH, DMSO) followed by protein detection assays such as ELISA to detect total protein encapsulated. Particle sizing and SEM analysis were performed for quality control purposes.

Example XIII

Therapeutic CCL-22 aAPCs in a Murine Mouse Model for Periodontal Disease

To induce periodontal disease in a mouse, we delivered $1 \times 10^9$ CFU of a diluted culture of *Aggregatibacter* (*Actinobacillus*) *actinomycetemcomitans* JP2 (anaerobically grown in supplemented agar medium, TSBV) in 100 µl of PBS with 2% carboxymethylcellulose, placed in the oral cavity of mice with a micropipette in accordance with Example XII. This procedure will be repeated at 48 and 96 hours later to fully establish periodontal disease.

Experimental groups will comprise of eight-week-old C57Bl/6 mice. CCL22 loaded particles will be injected in the palatal gingival tissue of right molars from the mesial of first molar until the distal face of the third molar, at the times of −1, 10 and 20 days of infection. Negative controls will include non-infected and sham-infected mice, which receive heat-killed bacteria in 2% carboxymethylcellulose solution, mice that receive PBS injection in left maxilla of the same LP group, and mice that receive the injection of control non-loaded particles. For a positive control, we will utilize mice that receive regular IP injections of VIP (vasoactive intestinal peptide) as this material induces systemic proliferation of regulatory T-cells. Chorny et al., "Vasoactive intestinal peptide induces regulatory dendritic cells that prevent acute graft-versus-host disease while maintaining the graft versus-tumor response" Blood 107:3787-3794 (2006). After 30 days of infection, mice will be euthanized and the samples collected for the following experimental analyses:

Alveolar Bone Loss/Healing Analysis. Evaluation of the extent of alveolar bone loss will be performed in accordance with Example XII and FIG. 12 above. Further, quantitative histological methodology will be used to characterize bone healing. Briefly, the maxillae will be hemisected, exposed overnight in 3% hydrogen peroxide and mechanically defleshed. The palatal faces of the molars will be photographed at 20× magnification using a dissecting microscope (Leica, Wetzlar, Germany), and the images will be analyzed using ImageTool 2.0 software (University of Texas Health Science Center, San Antonio). Quantitative analysis will be used for the measurement of the area between the cement-enamel junction (CEJ) and the alveolar bone crest (ABC) in the 3 posterior teeth, in arbitrary units of area (AUA). In total, 5 animals will be analyzed, and for each animal, the alveolar bone loss will be defined as the average of CEJ-ABC between the right and left arches.

Histological Assessment for Bone Healing. At the specified times, animals will be euthanized and block sections removed for immunohistochemistry analyses. Tissue sections will be divided into 2 groups (every other section), one for histological/histomorphometry analysis and the other for immunohistochemistry to assess new bone formation by staining for the Dentin Matrix Protein 1 and Bone Sialoprotein.

Real-Time PCR Analysis. Extraction of total RNA from periodontal tissues (upper molars with whole surrounding buccal and palatal periodontal tissues) will be performed with Trizol reagent (Invitrogen, Rockville, Md.) and cDNA synthesis. RealTime-PCR quantitative mRNA analyses will be done in a MiniOpticon system (BioRad, Hercules, Calif.), using SybrGreenMasterMix (Invitrogen), 100 nM specific primers, and 2.5 ng of cDNA in each reaction. We will analyze tissues for the presence of CCL-22, FoxP3, IL-10, RANK-L, and TGF-b. For mRNA analysis, the relative level of gene expression is calculated in reference to beta-actin using the cycle threshold (Ct) method.

Quantification and Visualization of Regulatory T-cells. Tissue will be resected and either: 1) sectioned for staining specific for regulatory T-cells using reported methods (Raimondi et al J Immunol 176, 2808-16 (2006) or 2) digested and separated using Ficoll in order to isolate white blood cells for flow cytometric analysis. The latter will allow us to determine the degree of FoxP3 expression specifically in regulatory T-cells (directly correlating to suppressive activity and also the percentage total regulatory T-cells in the periodontal space in comparison to other lyphocyte populations, CD4+CD25−, CD8+.

Statistical analysis. Preliminary data (n=3 mice per group with an internal control) obtained statistical significance which was slightly less than the p=0.05 cutoff. Power analysis based upon standard deviations and response magnitudes in pilot data (assuming power=0.8) indicates that we require n=5 to obtain desired confidence in our experimental results. Statistical significance between the infected and control mice of both strains will be analyzed by ANOVA, followed by Bonferroni post test. Values of P<0.05 will be considered statistically significant. We will also test both 1 month and 2 month time-points to examine whether or not therapeutic efficacy can be maintained and whether or not healing occurs at these time-points. PCR and AUA based measurements of bone loss/healing can be performed on the same set of mice (n=5×2 timepoints×4 groups) and histological analysis and flow cytometry can be performed on another set of mice (n=5×2 time-points×4 groups) leading to a total of 80 mice. Experimental groups include: 1) sham control, 2) blank particle control, 3) VIP positive control, and 4) CCL-22 particle experimental group.

Example XIV

Making Anisotropic Microspheres with Soft Protein Islets

Commercially available carboxylated phosphatydlserine (PS) microspheres (mean diameter 6.37 μm) were purchased from Bangs Laboratories Inc, USA. In preparation for the procedure, microspheres were washed twice in deionised water, then washed once in ethanol, centrifuged at 3500 rpm for 5 min, and re-suspended in water. Microbiology-grade glass cover slips were washed in soap solution, distilled water, and then ethanol (70%) under bath sonication for 15 min each. "Microwells" were developed by spotting 3 μl of microsphere suspension (10% w/v in water) onto a cover slip and dried sequentially at 25° C. for 1 hr 40° C. for 30 min and 60° C. for 10 min (Tg of PS bulk is 100° C. and reduces to 70° C. as the thickness reduces) 27 to avoid surface melting. The wells were further filled 4 times with concentrated microsphere suspension (30% w/v) in water with intermittent drying at 4-8° C. between additions. The colloidal crystals were further dried at room temperature for 3 hours. Prior to the addition of PDMS, cover slips with colloidal crystals were preheated to 60° C. for 5 min on a leveled hot plate (The PDMS ((PDMS/catalyst) (10:1) (w/w)) (Sylgard 184 silicone elastomer kit, Dowcorning Corp, MI, USA) solution was added and allowed to saturate and stabilize the interstitial spaces for a minute. This mixture was then immediately heated to 90° C. for 15 min. After setting of the PDMS scaffold (16 hrs at 40° C.), the cover slip was carefully removed to prepare the PDMS scaffold/colloidal crystal for protein patterning.

For protein labeling, scaffolds were first immersed in 0.1% Tween solution, to reduce the non-specific adsorption of proteins. Biotin-PEO (EZ Link®, Pierce, USA) was immobilized onto the microspheres in the PDMS scaffold. Carboxylate groups on the surface of microspheres (except the region at PDMS mask) were activated with 0.1M 1-ethyl-3-(3-dimethylaminopropyl)carbodiimide (EDC) (Acros, N.J., USA), and 0.2M N-hydroxysulfosuccinimide (Sulfo-NHS) (Thermo scientific, IL, USA) in 200 μl in 0.2M MES (pH5.5) buffer for 2 hours. Following the reaction, microspheres were washed two times with MES buffer prior to addition of 50 mM biotin-PEO (Fisher scientific, USA) in 200 μl MES buffer. After 2 hrs, the solution was removed and microspheres were washed two times with MES buffer in the scaffold. For etching, Tetra Butyl Ammonium Flouride (TBAF) (1M solution in Tetrahydrofuran, sigma-Aldrich Inc) in 1-Methyl, 2-Pyrrolidininone (NMP) (Sigma-Aldrich Inc)/Deionised Water (1:6)(v/v) in 0.1% Tween 80 solution was used. After 1 hour incubation of microspheres in etchant solution, the scaffolds were washed two times with the MES buffer. The second protein was then immobilized to the newly exposed area using EDC-NHS chemistry. For that the succinimide derivatized particles 200 μl of 0.2 mM albumin rhodamine (Albumin from bovine serum, tetramethyl rhodamine conjugate, Invitrogen) in 0.1% Tween 80/MES buffer (pH 5.5) was added to label the patches. The reaction proceeded for 2 hrs in the dark followed by washing with 1% (w/v) Bovine Serum albumin (BSA) (Sigma-Aldrich Inc) in 200 μl MES (pH 5.5) buffer. For labeling of the remaining surface of the particle, 200 μl MES buffer (pH 5.5) with 0.1% Tween and 1% BSA containing 0.2 mM avidin flourescein (Immunopure®, Pierce, USA) was added to the washed microspheres in the scaffolds. After 2 hours, the scaffolds were washed two times with MES buffer (pH5.5), and further washed one time in deionised water prior to storage at 4-8° C. The microspheres were scrapped out of the scaffold with a steel spatula. Optical microscopy images were taken with an Optical microscope (Caltex systems 3D Digital Video Inspection measurement system+signatone 1160 Probe Station). SEM studies were done with JSM 6330F. CLSM studies were performed using an Olympus FluoroView 1000 confocal microscope.

Example XV

Microparticle Fabrication

Figure 16:
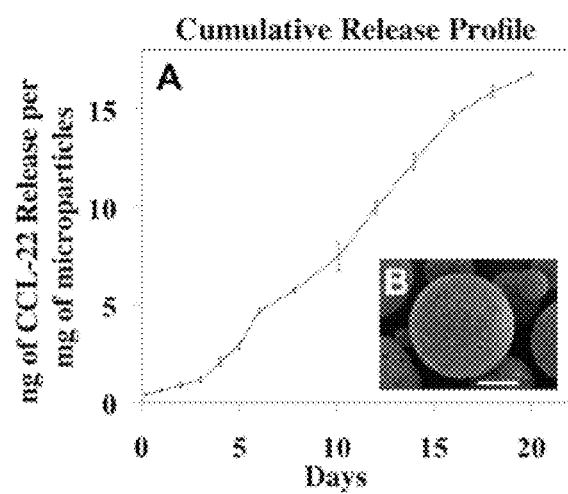
FIG. 16 presents exemplary data showing release kinetics of CCL22 from microparticles as measured in physiological buffered saline (PBS). Error Bars=Standard Deviations; n=3.
Figure 21:
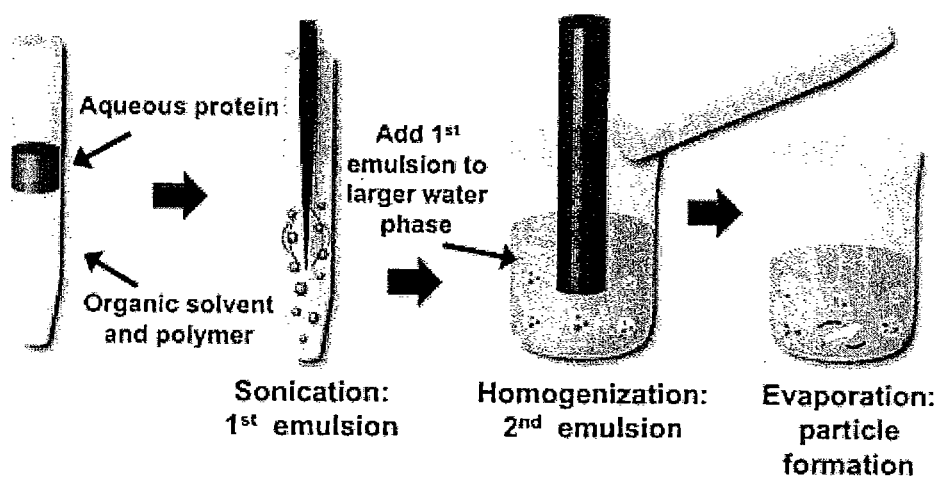
FIG. 21 presents one method of preparing microparticles.

Rationally design of controlled release microparticles may be created using a predictive mathematical model. S. R. Little, S. N. Rothstein, W. J. Federspiel, Journal of Materials Chemistry 18, 1873 (2008); S. N. Rothstein, Federspiel, W. J., Little, S. R., Biomaterials, (2009). The model allows computationally design formulations with specific release profiles based on drug/polymer characteristics and the desired release kinetics. Computer generated fabrication parameters are then used to inform the production process. Specifically, emulsion technique can encapsulate drugs in microparticles. FIG. 21. This model specifies that formulations should have the following characteristics to produce a 20 day linear release profile: Particle Size=20 μm; Internal Drug Pocket Size=500 nm; Average Polymer Molecular Weight=15 kDa; Polydispersity=1.5. FIG. 16.

Furthermore, a VIP (vasoactive intestinal peptide) microparticle formulation will be designed to provide a constant supply of the peptide over 20 days using the following characteristics: Particle Size=20 μm; Internal Drug Pocket Size=300 nm; Average Polymer Molecular Weight=15 kDa; Polydispersity=1.5. If VIP release behavior deviates from the designed profile, we are able to easily reformulate the microparticles to appropriately address the deviant characteristic. Release of VIP from microparitcles are expected to provide data similar to FIG. 16.

I claim:

1. A synthetic microparticle comprising at least one polymer and an internal structure, said internal structure comprising a plurality of compartments, wherein a soluble CCL22 chemokine is encapsulated within said plurality of compartments.

2. The synthetic microparticle of claim 1, wherein said microparticle is biodegradable.

3. The synthetic microparticle of claim 2, wherein said biodegradable microparticle undergoes a controlled chemokine release.

4. The synthetic microparticle of claim 3, wherein said controlled chemokine release is a short term release comprising between ten-twenty four hours.

5. The synthetic microparticle of claim 3, wherein said controlled chemokine release is a long term release comprising between twenty four hours and one year.

6. The synthetic microparticle of claim 3, wherein said controlled chemokine release is maintained for at least twenty days.

7. The synthetic microparticle of claim 1, wherein said at least one polymer comprises a polylactide-co-glycolide polymer.

8. The synthetic microparticle of claim 1, wherein said at least one polymer comprises a lactic acid monomer.

9. The synthetic microparticle of claim 8, wherein said at least one polymer further comprises a glycolic acid monomer.

10. The synthetic microparticle of claim 9, wherein said at least one polymer comprises said lactic acid monomer and said glycolic acid monomer in a predetermined ratio.

11. The synthetic microparticle of claim 10, wherein said predetermined ratio is 50:50.

12. The synthetic microparticle of claim 10, wherein said predetermined ratio is determined by a mathematical model.

13. The synthetic microparticle of claim 1, wherein the molecular weight of said at least one polymer is selected from the group consisting of approximately 10 kDa, a range of approximately 18-30 kDa and a range of approximately 40-78 kDa.

14. The synthetic microparticle of claim 1, wherein the average molecular weight of said at least one polymer is approximately 15 kilodaltons.

15. The synthetic microparticle of claim 1, wherein said microparticle is approximately ten to twenty microns in diameter.

16. The synthetic microparticle of claim 1, wherein said compartments range between approximately 300-500 nanometers in diameter.

17. The synthetic microparticle of claim 1, further comprising a pharmaceutical formulation.

* * * * *

UNITED STATES PATENT AND TRADEMARK OFFICE
CERTIFICATE OF CORRECTION

PATENT NO. : 9,757,339 B2            Page 1 of 1
APPLICATION NO. : 14/333000
DATED : September 12, 2017
INVENTOR(S) : Steven R. Little and Siddharth Jhunjhunwawa It is certified that error appears in the above-identified patent and that said Letters Patent is hereby corrected as shown below:

On the Title Page

Column 1 Item (72) Inventors should read as follows:
Steven R. Little, Allison Park, PA (US)
Siddharth Jhunjhunwawa, Bengaluru, KA (IN)

Signed and Sealed this
Twenty-ninth Day of May, 2018

Andrei Iancu
*Director of the United States Patent and Trademark Office*